US008183201B2

(12) United States Patent
Chuang et al.

(10) Patent No.: US 8,183,201 B2
(45) **Date of Patent: *May 22, 2012**

(54) METHODS OF TREATING αVβ3 INTEGRIN-ASSOCIATED DISEASES BY ADMINISTERING POLYPEPTIDES SELECTIVE FOR αVβ3 INTEGRIN

(75) Inventors: Woei-Jer Chuang, Tainan (TW); Wen-Mei Fu, Taipei (TW); Mannching Sherry Ku, Thiells, NY (US); Yen-Lun Huang, Taoyuan County (TW)

(73) Assignees: National Cheng Kung University, Tainan (TW); National Taiwan University, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/035,579

(22) Filed: Feb. 25, 2011

(65) Prior Publication Data

US 2011/0166072 A1 Jul. 7, 2011

Related U.S. Application Data

(63) Continuation-in-part of application No. 12/004,045, filed on Dec. 20, 2007, now Pat. No. 7,943,728.

(60) Provisional application No. 60/871,854, filed on Dec. 26, 2006.

(51) Int. Cl.

| | |
|---|---|
| ***A61K 38/00*** | (2006.01) |
| ***A61K 38/16*** | (2006.01) |
| ***A61K 38/08*** | (2006.01) |
| ***A61P 19/02*** | (2006.01) |
| ***A61P 29/00*** | (2006.01) |
| ***A61P 19/08*** | (2006.01) |

(52) U.S. Cl. ...... 514/1.1; 514/16.6; 514/16.7; 514/16.8; 514/16.9; 514/21.3; 514/21.8

(58) Field of Classification Search ........................ None
See application file for complete search history.

(56) References Cited

U.S. PATENT DOCUMENTS

| | | | |
|---|---|---|---|
| 4,179,337 | A | 12/1979 | Davis et al. |
| 4,301,144 | A | 11/1981 | Iwashita et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 5,380,646 | A | 1/1995 | Knight et al. |
| 6,710,030 | B1 | 3/2004 | Markland et al. |
| 6,974,884 | B2 | 12/2005 | Raines et al. |

FOREIGN PATENT DOCUMENTS

WO WO 95/34326 A1 12/1995

OTHER PUBLICATIONS

International Search Report and Written Opinion, dated Aug. 8, 2008.
Yang R., et al., "Rhodostomin inhibits thrombin-enhanced adhesion of ROS 17/2.8 cells through the blockade of αvβ3 integrin," Toxicon., Jul. 2005, vol. 46, No. 4, pp. 387-393.
Chang, H.H., et al., "Rhodostomin, an RGD-containing peptide expressed from a synthetic gene in *Escherichia coli*, facilitates the attachment of human hepatoma cells," Biochem Biophys Res Commun., Jan. 1993, vol. 190, No. 1, pp. 242-249.
Crippes, B.A., et al., "Antibody to β3 integrin inhibits osteoclast-mediated bone resorption in the thyroparathyroidectomized rat," Endocrinology, Mar. 1996, vol. 137, No. 3, pp. 918-924.
Dejana E., et al., "Bleeding time in rats: a comparison of different experimental conditions," Thromb Haemost., Aug. 1982, vol. 48, No. 1., pp. 108-111.
Engleman, V.W., et al., "A peptidomimetic antagonist of the alpha(v)beta3 integrin inhibits bone resorption in vitro and prevents osteoporosis in vivo," J Clin Invest, May 1997, vol. 99, No. 9, pp. 2284-2292.
Goltzman, D. "Discoveries, drugs and skeletal disorders," Nat Rev Drug Discov, Oct. 2002, vol. 1, No. 10, pp. 784-796.
Gould, R.J., et al., "Disintegrins: a family of integrin inhibitory proteins from viper venoms," Proc Soc Exp Biol Med, Nov. 1990, vol. 195, No. 2, pp. 168-171.
Horton, M.A., et al., "Arg-gly-asp (RGD) peptides and the anti-vitronectin receptor antibody 23C6 inhibit dentine resorption and cell spreading by osteoclasts," Exp Cell Res, Aug. 1991, vol. 195, No. 2. pp. 368-375.
Huang, T.F., "What have snakes taught us about integrins?," Cell Mol Life Sci, Jun. 1998, vol. 54, No. 6, pp. 527-540.
Huang, T.F., et al., "Rhodostomin, a snake venom peptide and its fragment inhibit platelet aggregation by acting as fibrinogen receptor antagonist," 11th International Congress on Thrombosis; Ljubljana, Yugoslavia, Jun. 1990, Abstract 141.
Hunkapiller M., et al., "A microchemical facility for the analysis and synthesis of genes and proteins," Nature, Jul. 1984, vol. 310, No. 5973, pp. 105-111.
Inoue, M., et al., "GM-CSF regulates expression of the functional integrins αvβ3 and αvβ5 in a reciprocal manner during osteoclastogenesis," J Bone Miner Res, 1995, vol. 10, p. S163a. (Abstr.).
Lin, Y.T., et al., "Inhibition of adipogenesis by RGD-dependent disintegrin," Biochemical Pharmacology, Nov. 2005, vol. 70, No. 10, pp. 1469-1478.
Mimura, H., et al., "1,25(OH)2D3 vitamin D3 transcriptionally activates the β3-integrin subunit gene in avian osteoclast precursors," Endocrinology, Mar. 1994, vol. 134, No. 3, pp. 1061-1066.
Miyauchi, A.J., et al., "Recognition of osteopontin and related peptides by an αvβ3 integrin stimulates immediate cell signals in osteoclasts," J Biol Chem, Oct. 1991, vol. 266, No. 30, pp. 20369-20374.
Monfardini, C., et al., "A branched monomethoxypoly(ethylene glycol) for protein modification," Bioconjugate Chem., Jan.-Feb. 1995, vol. 6, No. 1, pp. 62-69.

(Continued)

*Primary Examiner* — Robert Landsman
(74) *Attorney, Agent, or Firm* — Wood, Phillips, Katz, Clark & Mortimer

(57) ABSTRACT

The invention provides disintegrin variants, and more specifically to disintegrin variants which are selective αvβ3 integrin antagonists for treatment and prevention of αvβ3 integrin-associated diseases. The present invention also relates to pegylated proteins, including proteins comprising a disintegrin variant having an RGD motif variant $^{48}$ARLDDL$^{53}$. The invention also relates to the use of the polypeptides of the invention for the treatment and prevention of αvβ3 integrin-associated diseases.

21 Claims, 37 Drawing Sheets

OTHER PUBLICATIONS

Mundy, G.R. "Mechanisms of osteolytic bone destruction," Bone, 1991, Supplement, pp. S1-S6.

Mundy, G.R., "Metastasis to bone: causes, consequences and therapeutic opportunities," Nat Rev Cancer, Aug. 2002, vol. 2, No. 8, pp. 584-593.

Nakamura, I., et al., "Echistatin inhibits the migration of murine prefusion osteoclasts and the formation of multinucleated osteoclast-like cells," Endocrinology, Dec. 1998, vol. 139, No. 12, pp. 5182-5193.

Passaniti A., et al., "A simple, quantitative method for assessing angiogenesis and antiangiogenic agents using reconstituted basement membrane, heparin, and fibroblast growth factor," Lab. Invest., Oct. 1992, vol. 67, No. 4, pp. 519-528.

Ross, F.P., et al., "Interactions between the bone matrix proteins osteopontin and bone sialoprotein and the osteoclast integrin $\alpha v\beta 3$ potentiate bone resorption," J Biol Chem, May 1993, vol. 268, No. 13, pp. 9901-9907.

Sato K., Takayanagi H. "Osteoclasts, rheumatoid arthritis and osteoimmunology," Curr. Opin. Rheumatol., Jul. 2006, vol. 18, No. 4, pp. 419-426.

Stefano et al., "A conjugate of doxorubicin with lactosaminated albumin enhances the drug concentrations in all the forms of rat hepatocellular carcinomas independently of their differentiation grade," Liver Int., Aug. 2006, vol. 26, No. 6, pp. 726-733.

Tanaka, S., "Signaling axis in osteoclast biology and therapeutic targeting in the RANKL/RANK/OPG System," Am. J. Nephrol, 2007, vol. 27, No. 5, pp. 466-478.

Tang C.H., et al., "Enhancement of fibronectin fibrillogenesis and bone formation by basic fibroblast growth factor via protein kinase C-dependent pathway in rat osteoblasts," Mol Pharmacol., Sep. 2004, vol. 66, No. 3, pp. 440-449.

Turner C.H., Burr D.B., "Basic biomechanical measurements of bone: a tutorial," Bone, Jul.-Aug. 1993, vol. 14, No. 4, pp. 595-608.

Turner C.H., et al., "The effects of fluoridated water on bone strength," Orthop Res, Jul. 1992, vol. 10, No. 4, pp. 581-587.

Van Der Heijde D.M., et al., "Radiographic progression on radiographs of hands and feet during the first 3 years of rheumatoid arthritis measured according to sharp's method (van der Heijde modification)," J. Rheumatol., Sep. 1995; vol. 22, No. 9, pp. 1792-1796.

Van't Hof, R.J.; Ralston, S.H., "Nitric oxide and bone," Immunology, Jul. 2001, vol. 103., No. 3, pp. 255-261.

Weinreb M., et al., "Depression of osteoblastic activity in immobilized limbs of suckling rats," J Bone Miner Res., Jul. 1991, vol. 6, No. 7, pp. 725-731.

Wilkinson-Berka, J.L., et al., "COX-2 inhibition and retinal angiogenesis in a mouse model of retinopathy of prematurity," Invest Ophthalmol Vis Sci., Mar. 2003, vol. 44, No. 3, pp. 974-979.

Yang R., et al., "Differential effects of bone mineral content and bone area on vertebral strength in a swine model," Calcif Tissue Int., Jul. 1998, vol. 63, No. 1, pp. 86-90.

Yang, R.S., et al., "Inhibition of tumor formation by snake venom disintegrin," Toxicon., Apr. 2005, vol. 45, No. 5, pp. 661-669.

Yeh, C.H., et al., "Rhodostomin, a snake venom disintegrin, inhibits angiogenesis elicited by basic fibroblast growth factor and suppresses tumor growth by a selective $\alpha v\beta 3$ blockade of endothelial cells," Mol Pharmacol., May 2001, vol. 59, No. 5, pp. 1333-1342.

Yoneda, T., et al., "Bone-seeking clone exhibits different biological properties from the MDA-MB-231 parental human breast cancer cells and a brain-seeking clone in vivo and in vitro," J Bone Miner Res, Aug. 2001, vol. 16, No. 8, pp. 1486-1495.

Zallipsky, S., "Functionalized poly(ethylene glycol) for the preparation of biologically relevant conjugates," Bioconjugate Chem., Mar.-Apr. 1995, vol. 6, No. 2, pp. 150-165.

Zhang, X.P., et al., "Specific interaction of the recombinant disintegrin-like domain of MDC-15 (metargidin, ADAM-15) with integrin alphavbeta3," J Biol Chem, Mar. 1998, vol. 273, No. 13, pp. 7345-7350.

Chang Chih-Pei et al., "Positional importance of Pro53 adjacent to the Arg49-Gly50-Asp51 sequence of rhodostomin in binding to integrin alphaIIbbeta3", Biochemical Journal, vol. 357, No. 1, Jul. 2001, pp. 57-64.

SEQ ID NO: 1:

Gly Lys Glu Cys Asp Cys Ser Ser Pro Glu Asn Pro Cys Cys Asp Ala

Ala Thr Cys Lys Leu Arg Pro Gly Ala Gln Cys Gly Glu Gly Leu Cys

Cys Glu Gln Cys Lys Phe Ser Arg Ala Gly Lys Ile Cys Arg Ile Pro

Arg Gly Asp Met Pro Asp Asp Arg Cys Thr Gly Gln Ser Ala Asp Cys

Pro Arg Tyr His

SEQ ID NO: 57

Gly Lys Glu Cys Asp Cys Ser Ser Pro Glu Asn Pro Cys Cys Asp Ala

Ala Thr Cys Lys Leu Arg Pro Gly Ala Gln Cys Gly Glu Gly Leu Cys

Cys Glu Gln Cys Lys Phe Ser Arg Ala Gly Lys Ile Cys Arg Ile Ala

Arg Gly Asp Asp Pro Asp Asp Arg Cys Thr Gly Gln Ser Ala Asp Cys

Pro Arg Tyr His

SEQ ID NO: 58

Gly Lys Glu Cys Asp Cys Ser Ser Pro Glu Asn Pro Cys Cys Asp Ala

Ala Thr Cys Lys Leu Arg Pro Gly Ala Gln Cys Gly Glu Gly Leu Cys

Cys Glu Gln Cys Lys Phe Ser Arg Ala Gly Lys Ile Cys Arg Ile Ala

Arg Gly Asp Asp Val Asp Asp Arg Cys Thr Gly Gln Ser Ala Asp Cys

Pro Arg Tyr His

SEQ ID NO: 59

Gly Lys Glu Cys Asp Cys Ser Ser Pro Glu Asn Pro Cys Cys Asp Ala

Ala Thr Cys Lys Leu Arg Pro Gly Ala Gln Cys Gly Glu Gly Leu Cys

Cys Glu Gln Cys Lys Phe Ser Arg Ala Gly Lys Ile Cys Arg Ile Ala

Arg Gly Asp Asp Leu Asp Asp Arg Cys Thr Gly Gln Ser Ala Asp Cys

Pro Arg Tyr His

FIG. 14A

SEQ ID NO: 60

Gly Lys Glu Cys Asp Cys Ser Ser Pro Glu Asn Pro Cys Cys Asp Ala

Ala Thr Cys Lys Leu Arg Pro Gly Ala Gln Cys Gly Glu Gly Leu Cys

Cys Glu Gln Cys Lys Phe Ser Arg Ala Gly Lys Ile Cys Arg Ile Pro

Arg Gly Asp Asp Leu Asp Asp Arg Cys Thr Gly Gln Ser Ala Asp Cys

Pro Arg Tyr His

SEQ ID NO: 61

Gly Lys Glu Cys Asp Cys Ser Ser Pro Glu Asn Pro Cys Cys Asp Ala

Ala Thr Cys Lys Leu Arg Pro Gly Ala Gln Cys Gly Glu Gly Leu Cys

Cys Glu Gln Cys Lys Phe Ser Arg Ala Gly Lys Ile Cys Arg Ile Ala

Arg Gly Asp Asp Met Asp Asp Arg Cys Thr Gly Gln Ser Ala Asp Cys

Pro Arg Tyr His

SEQ ID NO: 62

Gly Lys Glu Cys Asp Cys Ser Ser Pro Glu Asn Pro Cys Cys Asp Ala

Ala Thr Cys Lys Leu Arg Pro Gly Ala Gln Cys Gly Glu Gly Leu Cys

Cys Glu Gln Cys Lys Phe Ser Arg Ala Gly Lys Ile Cys Arg Ile Pro

Arg Gly Asp Asp Met Asp Asp Arg Cys Thr Gly Gln Ser Ala Asp Cys

Pro Arg Tyr His

SEQ ID NO: 63

Gly Lys Glu Cys Asp Cys Ser Ser Pro Glu Asn Pro Cys Cys Asp Ala

Ala Thr Cys Lys Leu Arg Pro Gly Ala Gln Cys Gly Glu Gly Leu Cys

Cys Glu Gln Cys Lys Phe Ser Arg Ala Gly Lys Ile Cys Arg Ile Pro

Arg Leu Asp Met Pro Asp Asp Arg Cys Thr Gly Gln Ser Ala Asp Cys

Pro Arg Tyr His

FIG. 14B

SEQ ID NO: 64

Gly Lys Glu Cys Asp Cys Ser Ser Pro Glu Asn Pro Cys Cys Asp Ala
Ala Thr Cys Lys Leu Arg Pro Gly Ala Gln Cys Gly Glu Gly Leu Cys
Cys Glu Gln Cys Lys Phe Ser Arg Ala Gly Lys Ile Cys Arg Ile Pro
Arg Leu Asp Asp Leu Asp Asp Arg Cys Thr Gly Gln Ser Ala Asp Cys
Pro Arg Tyr His

SEQ ID NO: 65

Gly Lys Glu Cys Asp Cys Ser Ser Pro Glu Asn Pro Cys Cys Asp Ala
Ala Thr Cys Lys Leu Arg Pro Gly Ala Gln Cys Gly Glu Gly Leu Cys
Cys Glu Gln Cys Lys Phe Ser Arg Ala Gly Lys Ile Cys Arg Ile Ala
Arg Leu Asp Asp Leu Asp Asp Arg Cys Thr Gly Gln Ser Ala Asp Cys
Pro Arg Tyr His

SEQ ID NO: 66

Gly Lys Glu Cys Asp Cys Ser Ser Pro Glu Asn Pro Cys Cys Asp Ala
Ala Thr Cys Lys Leu Arg Pro Gly Ala Gln Cys Gly Glu Gly Leu Cys
Cys Glu Gln Cys Lys Phe Ser Arg Ala Gly Lys Ile Cys Arg Ile Pro
Arg Ile Asp Met Pro Asp Asp Arg Cys Thr Gly Gln Ser Ala Asp Cys
Pro Arg Tyr His

SEQ ID NO: 67

Gly Lys Glu Cys Asp Cys Ser Ser Pro Glu Asn Pro Cys Cys Asp Ala
Ala Thr Cys Lys Leu Arg Pro Gly Ala Gln Cys Gly Glu Gly Leu Cys
Cys Glu Gln Cys Lys Phe Ser Arg Ala Gly Lys Ile Cys Arg Ile Pro
Arg His Asp Met Pro Asp Asp Arg Cys Thr Gly Gln Ser Ala Asp Cys
Pro Arg Tyr His

FIG. 14C

SEQ ID NO: 68

Gly Lys Glu Cys Asp Cys Ser Ser Pro Glu Asn Pro Cys Cys Asp Ala
Ala Thr Cys Lys Leu Arg Pro Gly Ala Gln Cys Gly Glu Gly Leu Cys
Cys Glu Gln Cys Lys Phe Ser Arg Ala Gly Lys Ile Cys Arg Ile Pro
Arg Gly Asp Asn Pro Asp Asp Arg Cys Thr Gly Gln Ser Ala Asp Cys
Pro Arg Tyr His

SEQ ID NO: 69

Gly Lys Glu Cys Asp Cys Ser Ser Pro Glu Asn Pro Cys Cys Asp Ala
Ala Thr Cys Lys Leu Arg Pro Gly Ala Gln Cys Gly Glu Gly Leu Cys
Cys Glu Gln Cys Lys Phe Ser Arg Ala Gly Lys Ile Cys Arg Ile Pro
Arg Gly Asp Gly Pro Asp Asp Arg Cys Thr Gly Gln Ser Ala Asp Cys
Pro Arg Tyr His

FIG. 14D

SEQ ID NO: 43

GGTAAGGAAT GTGACTGTTC TTCTCCAGAA AACCCATGTT GTGACGCTGC TACTTGTAAG . . .60
TTGAGACCAG GTGCTCAATG TGGTGAAGGT TTGTGTTGTG AACAATGTAA GTTCTCTAGA . .120
GCTGGTAAGA TCTGTAGAAT CCCAAGAGGT GACATGCCAG ACGACAGATG TACTGGTCAA .180
TCTGCTGACT GTCCAAGATA CCAC . 204

SEQ ID NO: 44

GGTAAGGAAT GTGACTGTTC TTCTCCAGAA AACCCATGTT GTGACGCTGC TACTTGTAAG . . . 60
TTGAGACCAG GTGCTCAATG TGGTGAAGGT TTGTGTTGTG AACAATGTAA GTTCTCTAGA . . 120
GCTGGTAAGA TCTGTAGAAT CGCAAGAGGT GACGACCCAG ACGACAGATG TACTGGTCAA .180
TCTGCTGACT GTCCAAGATA CCAC . 204

SEQ ID NO: 45

GGGTAAGGAAT GTGACTGTTC TTCTCCAGAA AACCCATGTT GTGACGCTGC TACTTGTAAG . .60
TTGAGACCAG GTGCTCAATG TGGTGAAGGT TTGTGTTGTG AACAATGTAA GTTCTCTAGA . . 120
GCTGGTAAGA TCTGTAGAAT CGCAAGAGGT GACGACGTAG ACGACAGATG TACTGGTCAA .180
TCTGCTGACT GTCCAAGATA CCAC . 204

SEQ ID NO: 46

GGTAAGGAAT GTGACTGTTC TTCTCCAGAA AACCCATGTT GTGACGCTGC TACTTGTAAG . . .60
TTGAGACCAG GTGCTCAATG TGGTGAAGGT TTGTGTTGTG AACAATGTAA GTTCTCTAGA . . 120
GCTGGTAAGA TCTGTAGAAT CGCAAGAGGT GACGACCTAG ACGACAGATG TACTGGTCAA .180
TCTGCTGACT GTCCAAGATA CCAC . 204

SEQ ID NO: 47

GGTAAGGAAT GTGACTGTTC TTCTCCAGAA AACCCATGTT GTGACGCTGC TACTTGTAAG . . . 60
TTGAGACCAG GTGCTCAATG TGGTGAAGGT TTGTGTTGTG AACAATGTAA GTTCTCTAGA . . 120
GCTGGTAAGA TCTGTAGAAT CCCAAGAGGT GACGACCTAG ACGACAGATG TACTGGTCAA . 180
TCTGCTGACT GTCCAAGATA CCAC . 204

SEQ ID NO: 48

GGTAAGGAAT GTGACTGTTC TTCTCCAGAA AACCCATGTT GTGACGCTGC TACTTGTAAG . . . 60
TTGAGACCAG GTGCTCAATG TGGTGAAGGT TTGTGTTGTG AACAATGTAA GTTCTCTAGA . . 120
GCTGGTAAGA TCTGTAGAAT CGCAAGAGGT GACGACATGG ACGACAGATG TACTGGTCAA 180
TCTGCTGACT GTCCAAGATA CCAC . 204

FIG. 15A

SEQ ID NO: 49

GGTAAGGAAT GTGACTGTTC TTCTCCAGAA AACCCATGTT GTGACGCTGC TACTTGTAAG . . . 60
TTGAGACCAG GTGCTCAATG TGGTGAAGGT TTGTGTTGTG AACAATGTAA GTTCTCTAGA . . 120
GCTGGTAAGA TCTGTAGAAT CCCAAGAGGT GACGACATGG ACGACAGATG TACTGGTCAA . 180
TCTGCTGACT GTCCAAGATA CCAC . 204

SEQ ID NO: 50

GGTAAGGAAT GTGACTGTTC TTCTCCAGAA AACCCATGTT GTGACGCTGC TACTTGTAAG . . .60
TTGAGACCAG GTGCTCAATG TGGTGAAGGT TTGTGTTGTG AACAATGTAA GTTCTCTAGA . .120
GCTGGTAAGA TCTGTAGAAT CCCAAGACTT GACATGCCAG ACGACAGATG TACTGGTCAA . 180
TCTGCTGACT GTCCAAGATA CCAC . 204

SEQ ID NO: 51

GGTAAGGAAT GTGACTGTTC TTCTCCAGAA AACCCATGTT GTGACGCTGC TACTTGTAAG . . .60
TTGAGACCAG GTGCTCAATG TGGTGAAGGT TTGTGTTGTG AACAATGTAA GTTCTCTAGA . .120
GCTGGTAAGA TCTGTAGAAT CCCAAGACTT GACGACCTAG ACGACAGATG TACTGGTCAA . 180
TCTGCTGACT GTCCAAGATA CCAC . 204

SEQ ID NO: 52

GGTAAGGAAT GTGACTGTTC TTCTCCAGAA AACCCATGTT GTGACGCTGC TACTTGTAAG . . .60
TTGAGACCAG GTGCTCAATG TGGTGAAGGT TTGTGTTGTG AACAATGTAA GTTCTCTAGA . .120
GCTGGTAAGA TCTGTAGAAT CGCAAGACTT GACGACCTAG ACGACAGATG TACTGGTCAA .180
TCTGCTGACT GTCCAAGATA CCAC . 204

SEQ ID NO: 53

GGTAAGGAAT GTGACTGTTC TTCTCCAGAA AACCCATGTT GTGACGCTGC TACTTGTAAG . . 60
TTGAGACCAG GTGCTCAATG TGGTGAAGGT TTGTGTTGTG AACAATGTAA GTTCTCTAGA . .120
GCTGGTAAGA TCTGTAGAAT CCCAAGAATC GACATGCCAG ACGACAGATG TACTGGTCAA .180
TCTGCTGACT GTCCAAGATA CCAC . 204

SEQ ID NO: 54

GGTAAGGAAT GTGACTGTTC TTCTCCAGAA AACCCATGTT GTGACGCTGC TACTTGTAAG . . 60
TTGAGACCAG GTGCTCAATG TGGTGAAGGT TTGTGTTGTG AACAATGTAA GTTCTCTAGA . .120
GCTGGTAAGA TCTGTAGAAT CCCAAGACAC GACATGCCAG ACGACAGATG TACTGGTCAA .180
TCTGCTGACT GTCCAAGATA CCAC . 204

FIG. 15B

SEQ ID NO: 55

GGTAAGGAAT GTGACTGTTC TTCTCCAGAA AACCCATGTT GTGACGCTGC TACTTGTAAG . . 60
TTGAGACCAG GTGCTCAATG TGGTGAAGGT TTGTGTTGTG AACAATGTAA GTTCTCTAGA . .120
GCTGGTAAGA TCTGTAGAAT CCCAAGAGGT GACAACCCAG ACGACAGATG TACTGGTCAA .180
TCTGCTGACT GTCCAAGATA CCAC . 204

SEQ ID NO: 56

GGTAAGGAAT GTGACTGTTC TTCTCCAGAA AACCCATGTT GTGACGCTGC TACTTGTAAG . . 60
TTGAGACCAG GTGCTCAATG TGGTGAAGGT TTGTGTTGTG AACAATGTAA GTTCTCTAGA . .120
GCTGGTAAGA TCTGTAGAAT CCCAAGAGGT GACGGTCCAG ACGACAGATG TACTGGTCAA .180
TCTGCTGACT GTCCAAGATA CCAC . 204

FIG. 15C albolabrin SEQ ID NO: 78

EAGEDCDCGSPANPCCDAATCKLLPGAQCGEGLCCDQCSFMKKGTICRRARGDDLD
DYCNGISAGCPRNPLHA albolabrin DNA SEQ ID NO: 79

GAAGCGGGCGAAGATTGCGATTGCGGCAGCCCGGCGAACCCGTGCTGCGATGCGG
CGACCTGCAAACTGCTGCCGGGCGCGCAGTGCGGCGAAGGCCTGTGCTGCGATCA
GTGCAGCTTTatgAAAAAAGGCACCATTTGCCGTCGTGCGCGTGGCGATGATCTGGA
TGATTATTGCAACGGCATTAGCGCGGGCTGCCCGCGTAACCCGCTGCATGCG applagin SEQ ID NO: 80

EAGEECDCGSPENPCCDAATCKLRPGAQCAEGLCCDQCKFMKEGTVCRARGDDVND
YCNGISAGCPRNPFH applagin DNA SEQ ID NO: 81

GAAGCGGGCGAAGAATGCGATTGCGGCAGCCCGGAAAACCCGTGCTGCGATGCG
GCGACCTGCAAACTGCGTCCGGGCGCGCAGTGCGCGGAAGGCCTGTGCTGCGATC
AGTGCAAATTTatgAAAGAAGGCACCGTGTGCCGTGCGCGTGGCGATGATGTGAAC
GATTATTGCAACGGCATTAGCGCGGGCTGCCCGCGTAACCCGTTTCAT basilicin SEQ ID NO: 82

AGEECDCGSPANPCCDAATCKLRPGAQCAEGLCCDQCRFIKKGKICRRARGDNPDDR
CTGQSADCPRNHFHA basilicin DNA SEQ ID NO: 83

GCGGGCGAAGAATGCGATTGCGGCAGCCCGGCGAACCCGTGCTGCGATGCGGCGA
CCTGCAAACTGCGTCCGGGCGCGCAGTGCGCGGAAGGCCTGTGCTGCGATCAGTG
CCGTTTTATTAAAAAAGGCAAAATTTGCCGTCGTGCGCGTGGCGATAACCCGGATG
ATCGTTGCACCGGCCAGAGCGCGGATTGCCCGCGTAACCATTTTCATGCG batroxostatin SEQ ID NO: 84

EAGEECDCGTPENPCCDAATCKLRPGAQCAEGLCCDQCRFKGAGKICRRARGDNPD
DRCTGQSADCPRNRF batroxostatin DNA SEQ ID NO: 85

GAAGCGGGCGAAGAATGCGATTGCGGCACCCCGGAAAACCCGTGCTGCGATGCGG
CGACCTGCAAACTGCGTCCGGGCGCGCAGTGCGCGGAAGGCCTGTGCTGCGATCA
GTGCCGTTTTAAAGGCGCGGGCAAAATTTGCCGTCGTGCGCGTGGCGATAACCCG
GATGATCGTTGCACCGGCCAGAGCGCGGATTGCCCGCGTAACCGTTTT

FIG. 16A bitan (Bitistatin) (Venom protein CM-2) (Arietin) SEQ ID NO: 86

SPPVCGNKILEQGEDCDCGSPANCQDRCCNAATCKLTPGSQCNYGECCDQCRFKKAG
TVCRIARGDWNDDYCTGKSSDCPWNH bitistatin DNA SEQ ID NO: 87

AGCCCGCCGGTGTGCGGCAACAAAATTCTGGAACAGGGCGAAGATTGCGATTGCG
GCAGCCCGGCGAACTGCCAGGATCGTTGCTGCAACGCGGCGACCTGCAAACTGAC
CCCGGGCAGCCAGTGCAACTATGGCGAATGCTGCGATCAGTGCCGTTTTAAAAAA
GCGGGCACCGTGTGCCGTATTGCGCGTGGCGATTGGAACGATGATTATTGCACCGG
CAAAAGCAGCGATTGCCCGTGGAACCAT cereberin SEQ ID NO: 88

EAGEECDCGSPANPCCDAATCKLRPGAQCAEGLCCDQCRFIKKGKICRRARGDNPDD
RCTGQSADCPRNRFH cereberin DNA SEQ ID NO: 89

GAAGCGGGCGAAGAATGCGATTGCGGCAGCCCGGCGAACCCGTGCTGCGATGCGG
CGACCTGCAAACTGCGTCCGGGCGCGCAGTGCGCGGAAGGCCTGTGCTGCGATCA
GTGCCGTTTTATTAAAAAAGGCAAAATTTGCCGTCGTGCGCGTGGCGATAACCCGG
ATGATCGTTGCACCGGCCAGAGCGCGGATTGCCCGCGTAACCGTTTTCAT cerastin SEQ ID NO: 90

EAGEECDCGTPENPCCDAATCKLRPGAQCADGLCCDQCRFMKKGTVCRVARGDWN
DDTCTGQSADCPRNGLYG cerastin DNA SEQ ID NO: 91

GAAGCGGGCGAAGAATGCGATTGCGGCACCCCGGAAAACCCGTGCTGCGATGCGG
CGACCTGCAAACTGCGTCCGGGCGCGCAGTGCGCGGATGGCCTGTGCTGCGATCA
GTGCCGTTTTATGAAAAAAGGCACCGTGTGCCGTGTGGCGCGTGGCGATTGGAAC
GATGATACCTGCACCGGCCAGAGCGCGGATTGCCCGCGTAACGGCCTGTATGGC crotatroxin SEQ ID NO: 92

AGEECDCGSPANPCCDAATCKLRPGAQCADGLCCDQCRFIKKGTVCRPARGDWNDD
TCTGQSADCPRNGLYG

FIG. 16B crotatroxin DNA SEQ ID NO: 93

GCGGGCGAAGAATGCGATTGCGGCAGCCCGGCGAACCCGTGCTGCGATGCGGCGA
CCTGCAAACTGCGTCCGGGCGCGCAGTGCGCGGATGGCCTGTGCTGCGATCAGTG
CCGTTTTATTAAAAAAGGCACCGTGTGCCGTCCGGCGCGTGGCGATTGGAACGATG
ATACCTGCACCGGCCAGAGCGCGGATTGCCCGCGTAACGGCCTGTATGGC durissin SEQ ID NO: 94

AGEECDCGSPANPCCDAATCKLRPGAQCADGLCCDQCRFIKKGTVCRPARGDWNDD
TCTGQSADCPRNGLYG durissin DNA SEQ ID NO: 95

GCGGGCGAAGAATGCGATTGCGGCAGCCCGGCGAACCCGTGCTGCGATGCGGCGA
CCTGCAAACTGCGTCCGGGCGCGCAGTGCGCGGATGGCCTGTGCTGCGATCAGTG
CCGTTTTATTAAAAAAGGCACCGTGTGCCGTCCGGCGCGTGGCGATTGGAACGATG
ATACCTGCACCGGCCAGAGCGCGGATTGCCCGCGTAACGGCCTGTATGGC elegantin SEQ ID NO: 96

EAGEECDCGSPENPCCDAATCKLRPGAQCADGLCCDQCRFIEEGIICRRARGDDLDDY
CNGISGDCPRNPFHA

Elegantin DNA SEQ ID NO: 97

GAAGCGGGCGAAGAATGCGATTGCGGCAGCCCGGAAAACCCGTGCTGCGATGCG
GCGACCTGCAAACTGCGTCCGGGCGCGCAGTGCGCGGATGGCCTGTGCTGCGATC
AGTGCCGTTTTATTGAAGAAGGCATTATTTGCCGTCGTGCGCGTGGCGATGATCTGG
ATGATTATTGCAACGGCATTAGCGGCGATTGCCCGCGTAACCCGTTTCATGCG flavoridin SEQ ID NO: 98

GEECDCGSPSNPCCDAATCKLRPGAQCADGLCCDQCRFKKKRTICRIARGDFPDDRCT
GLSNDCPRWNDL flavoridin DNA SEQ ID NO: 99

GGCGAAGAATGCGATTGCGGCAGCCCGAGCAACCCGTGCTGCGATGCGGCGACCT
GCAAACTGCGTCCGGGCGCGCAGTGCGCGGATGGCCTGTGCTGCGATCAGTGCCG
TTTTAAAAAAAAACGTACCATTTGCCGTATTGCGCGTGGCGATTTTCCGGATGATCG
TTGCACCGGCCTGAGCAACGATTGCCCGCGTTGGAACGATCTG flavostatin SEQ ID NO: 100

GEECDCGSPSNPCCDAATCKLRPGAQCADGLCCDQCRFKKKRTICRRARGDNPDDRC
TGQSADCPRNS

FIG. 16C flavostatin DNA SEQ ID NO: 101

GGCGAAGAATGCGATTGCGGCAGCCCGAGCAACCCGTGCTGCGATGCGGCGACCT
GCAAACTGCGTCCGGGCGCGCAGTGCGCGGATGGCCTGTGCTGCGATCAGTGCCG
TTTTAAAAAAAAACGTACCATTTGCCGTCGTGCGCGTGGCGATAACCCGGATGATC
GTTGCACCGGCCAGAGCGCGGATTGCCCGCGTAACAGC halysin SEQ ID NO: 102

EAGEECDCGSPGNPCCDAATCKLRQGAQCAEGLCCDQCRFMKKGTVCRIARGDDM
DDYCNGISAGCPRNPF halysin DNA SEQ ID NO: 103

GAAGCGGGCGAAGAATGCGATTGCGGCAGCCCGGGCAACCCGTGCTGCGATGCGG
CGACCTGCAAACTGCGTCAGGGCGCGCAGTGCGCGGAAGGCCTGTGCTGCGATCA
GTGCCGTTTTatgAAAAAAGGCACCGTGTGCCGTATTGCGCGTGGCGATGATatgGAT
GATTATTGCAACGGCATTAGCGCGGGCTGCCCGCGTAACCCGTTT halystatin SEQ ID NO: 104

EAGEDCDCGAPANPCCDAATCKLRPGAQCAEGLCCDQCRFMKEGTICRMARGDDM
DDYCNGISAGCPRNPFHA halystatin DNA SEQ ID NO: 105

GAAGCGGGCGAAGATTGCGATTGCGGCGCGCCGGCGAACCCGTGCTGCGATGCGG
CGACCTGCAAACTGCGTCCGGGCGCGCAGTGCGCGGAAGGCCTGTGCTGCGATCA
GTGCCGTTTTatgAAAGAAGGCACCATTTGCCGTatgGCGCGTGGCGATGATatgGATGA
TTATTGCAACGGCATTAGCGCGGGCTGCCCGCGTAACCCGTTTCATGCG jararacin SEQ ID NO: 106

EAGEECDCGTPGNPCCDAATCKLRPGAQCAEGLCCDQCRFKGAGKICRRARGDNPD
DRCTGQSADCPRNRFHA jararacin DNA SEQ ID NO: 107

GAAGCGGGCGAAGAATGCGATTGCGGCACCCCGGGCAACCCGTGCTGCGATGCGG
CGACCTGCAAACTGCGTCCGGGCGCGCAGTGCGCGGAAGGCCTGTGCTGCGATCA
GTGCCGTTTTAAAGGCGCGGGCAAAATTTGCCGTCGTGCGCGTGGCGATAACCCG
GATGATCGTTGCACCGGCCAGAGCGCGGATTGCCCGCGTAACCGTTTTCATGCG jarastatin SEQ ID NO: 108

EAGEECDCGTPGNPCCDAATCKLRPGAQCAEGLCCDQCRFMKEGTVCRRARGDDM
DDYCNGISAGCPRNPFHA

FIG. 16D jarastatin DNA SEQ ID NO: 109

GAAGCGGGCGAAGAATGCGATTGCGGCACCCCGGGCAACCCGTGCTGCGATGCGG
CGACCTGCAAACTGCGTCCGGGCGCGCAGTGCGCGGAAGGCCTGTGCTGCGATCA
GTGCCGTTTTatgAAAGAAGGCACCGTGTGCCGTCGTGCGCGTGGCGATGATatgGAT
GATTATTGCAACGGCATTAGCGCGGGCTGCCCGCGTAACCCGTTTCATGCG kistrin SEQ ID NO: 110

GKECDCSSPENPCCDAATCKLRPGAQCGEGLCCEQCKFSRAGKICRIPRGDMPDDRCT
GQSADCPRYH kistrin DNA SEQ ID NO: 111

GGCAAAGAATGCGATTGCAGCAGCCCGGAAAACCCGTGCTGCGATGCGGCGACCT
GCAAACTGCGTCCGGGCGCGCAGTGCGGCGAAGGCCTGTGCTGCGAACAGTGCA
AATTTAGCCGTGCGGGCAAAATTTGCCGTATTCCGCGTGGCGATatgCCGGATGATCG
TTGCACCGGCCAGAGCGCGGATTGCCCGCGTTATCAT lachesin SEQ ID NO: 112

EAGEECDCGAPANPCCDAATCKLRPGAQCAEGLCCDQCRFIKKGKICRRARGDNPD
DRCTGQSADCPRNGYYG lachesin DNA SEQ ID NO: 113

GAAGCGGGCGAAGAATGCGATTGCGGCGCGCCGGCGAACCCGTGCTGCGATGCG
GCGACCTGCAAACTGCGTCCGGGCGCGCAGTGCGCGGAAGGCCTGTGCTGCGATC
AGTGCCGTTTTATTAAAAAAGGCAAAATTTGCCGTCGTGCGCGTGGCGATAACCC
GGATGATCGTTGCACCGGCCAGAGCGCGGATTGCCCGCGTAACGGCTATTATGGC lutosin SEQ ID NO: 114

EAGEECDCGSPANPCCDAATCKLRPGAQCADGLCCDQCRFIKKGTVCRVARGDWND
DTCTGQSADCPRNGLYG lutosin DNA SEQ ID NO: 115

GAAGCGGGCGAAGAATGCGATTGCGGCAGCCCGGCGAACCCGTGCTGCGATGCG
GCGACCTGCAAACTGCGTCCGGGCGCGCAGTGCGCGGATGGCCTGTGCTGCGATC
AGTGCCGTTTTATTAAAAAAGGCACCGTGTGCCGTGTGGCGCGTGGCGATTGGAA
CGATGATACCTGCACCGGCCAGAGCGCGGATTGCCCGCGTAACGGCCTGTATGGC molossin SEQ ID NO: 116

EAGIECDCGSPENPCCDAATCKLRPGAQCADGLCCDQCRFIKKGKICRRARGDNPDD
RCTGQSADCPRNRFHA

FIG. 16E molossin DNA SEQ ID NO: 117

GAAGCGGGCATTGAATGCGATTGCGGCAGCCCGGAAAACCCGTGCTGCGATGCG
GCGACCTGCAAACTGCGTCCGGGCGCGCAGTGCGCGGATGGCCTGTGCTGCGATC
AGTGCCGTTTTATTAAAAAAGGCAAAATTTGCCGTCGTGCGCGTGGCGATAACCC
GGATGATCGTTGCACCGGCCAGAGCGCGGATTGCCCGCGTAACCGTTTTCATGCG

Salmosin SEQ ID NO: 118

EAGEECDCGSPGNPCCDAATCKLRQGAQCAEGLCCDQCRFMKEGTICRRARGDDLD
DYCNGISAGCPRNPFHA

Salmosin DNA SEQ ID NO: 119

GAAGCGGGCGAAGAATGCGATTGCGGCAGCCCGGGCAACCCGTGCTGCGATGCG
GCGACCTGCAAACTGCGTCAGGGCGCGCAGTGCGCGGAAGGCCTGTGCTGCGATC
AGTGCCGTTTTatgAAAGAAGGCACCATTTGCCGTCGTGCGCGTGGCGATGATCTG
GATGATTATTGCAACGGCATTAGCGCGGGCTGCCCGCGTAACCCGTTTCATGCG saxatilin SEQ ID NO: 120

EAGEECDCGAPANPCCDAATCKLRPGAQCAEGLCCDQCRFMKEGTICRMARGDDM
DDYCNGISAGCPRNPFHA saxatilin DNA SEQ ID NO: 121

GAAGCGGGCGAAGAATGCGATTGCGGCGCGCCGGCGAACCCGTGCTGCGATGCG
GCGACCTGCAAACTGCGTCCGGGCGCGCAGTGCGCGGAAGGCCTGTGCTGCGATC
AGTGCCGTTTTatgAAAGAAGGCACCATTTGCCGTatgGCGCGTGGCGATGATatgGAT
GATTATTGCAACGGCATTAGCGCGGGCTGCCCGCGTAACCCGTTTCATGCG tergeminin SEQ ID NO: 122

EAGEECDCGSPANPCCDAATCKLRPGAQCADGLCCDQCRFMKKGTVCRVARGDWN
DDTCTGQSADCPRNGLYG tergeminin DNA SEQ ID NO: 123

GAAGCGGGCGAAGAATGCGATTGCGGCAGCCCGGCGAACCCGTGCTGCGATGCG
GCGACCTGCAAACTGCGTCCGGGCGCGCAGTGCGCGGATGGCCTGTGCTGCGATC
AGTGCCGTTTTatgAAAAAAGGCACCGTGTGCCGTGTGGCGCGTGGCGATTGGAAC
GATGATACCTGCACCGGCCAGAGCGCGGATTGCCCGCGTAACGGCCTGTATGGC

Triflavin SEQ ID NO: 124

GEECDCGSPSNPCCDAATCKLRPGAQCADGLCCDQCRFKKKRTICRIARGDFPDDRC
TGQSADCPRWNGL

FIG. 16F triflavin DNA SEQ ID NO: 125

GGCGAAGAATGCGATTGCGGCAGCCCGAGCAACCCGTGCTGCGATGCGGCGACC
TGCAAACTGCGTCCGGGCGCGCAGTGCGCGGATGGCCTGTGCTGCGATCAGTGCC
GTTTTAAAAAAAAACGTACCATTTGCCGTATTGCGCGTGGCGATTTTCCGGATGAT
CGTTGCACCGGCCAGAGCGCGGATTGCCCGCGTTGGAACGGCCTG trimucrin SEQ ID NO: 126

EAGEECDCGSPENPCCDAATCKLRPGAQCAEGLCCDQCRFKKKRTICRRARGDNPDD
RCTGQSADCPRNGLYG trimucrin DNA SEQ ID NO: 127

GAAGCGGGCGAAGAATGCGATTGCGGCAGCCCGGAAAACCCGTGCTGCGATGCG
GCGACCTGCAAACTGCGTCCGGGCGCGCAGTGCGCGGAAGGCCTGTGCTGCGATC
AGTGCCGTTTTAAAAAAAAACGTACCATTTGCCGTCGTGCGCGTGGCGATAACCC
GGATGATCGTTGCACCGGCCAGAGCGCGGATTGCCCGCGTAACGGCCTGTATGGC trimutase SEQ ID NO: 128

EAGEECDCGSPENPCCDAATCKLRPGAQCAEGLCCDQCRFKKKRTICRRARGDNPDD
RCTGQSADCPRNGLYG trimutase DNA SEQ ID NO: 129

GAAGCGGGCGAAGAATGCGATTGCGGCAGCCCGGAAAACCCGTGCTGCGATGCG
GCGACCTGCAAACTGCGTCCGGGCGCGCAGTGCGCGGAAGGCCTGTGCTGCGATC
AGTGCCGTTTTAAAAAAAAACGTACCATTTGCCGTCGTGCGCGTGGCGATAACCC
GGATGATCGTTGCACCGGCCAGAGCGCGGATTGCCCGCGTAACGGCCTGTATGGC ussuristatin-1 (US-1) SEQ ID NO: 130

GEECDCGSPGNPCCDAATCKLRPGAQCAEGLCCEQCRFIKAGTVCRVARGDWNDDK
CTGQSADCPRNGFYG ussuristatin-1 DNA SEQ ID NO: 131

GGCGAAGAATGCGATTGCGGCAGCCCGGGCAACCCGTGCTGCGATGCGGCGACC
TGCAAACTGCGTCCGGGCGCGCAGTGCGCGGAAGGCCTGTGCTGCGAACAGTGCC
GTTTTATTAAAGCGGGCACCGTGTGCCGTGTGGCGCGTGGCGATTGGAACGATGA
TAAATGCACCGGCCAGAGCGCGGATTGCCCGCGTAACGGCTTTTATGGC ussuristatin-2 (US-2) SEQ ID NO: 132

EAGEECDCGAPANPCCDAATCKLRPGAQCAEGDCCEQCRFVKEGTVCREAKGDWN
DDSCTGQSADCPRNGF

FIG. 16G ussuristatin-2 DNA SEQ ID NO: 133

GAAGCGGGCGAAGAATGCGATTGCGGCGCGCCGGCGAACCCGTGCTGCGATGCG
GCGACCTGCAAACTGCGTCCGGGCGCGCAGTGCGCGGAAGGCGATTGCTGCGAA
CAGTGCCGTTTTGTGAAAGAAGGCACCGTGTGCCGTGAAGCGAAAGGCGATTGG
AACGATGATAGCTGCACCGGCCAGAGCGCGGATTGCCCGCGTAACGGCTTT viridin SEQ ID NO: 134

AGEECDCGSPANPCCDAATCKLRPGAQCADGLCCDQCRFIKKGKICRRARGDNPDD
RCTGQSADCPRNRFH viridin DNA SEQ ID NO: 135

GCGGGCGAAGAATGCGATTGCGGCAGCCCGGCGAACCCGTGCTGCGATGCGGCG
ACCTGCAAACTGCGTCCGGGCGCGCAGTGCGCGGATGGCCTGTGCTGCGATCAGT
GCCGTTTTATTAAAAAAGGCAAAATTTGCCGTCGTGCGCGTGGCGATAACCCGGA
TGATCGTTGCACCGGCCAGAGCGCGGATTGCCCGCGTAACCGTTTTCAT

FIG. 16H

FIG 17A
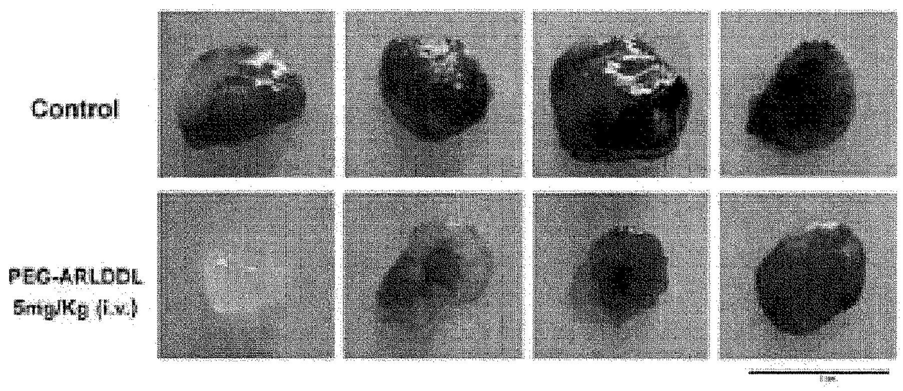
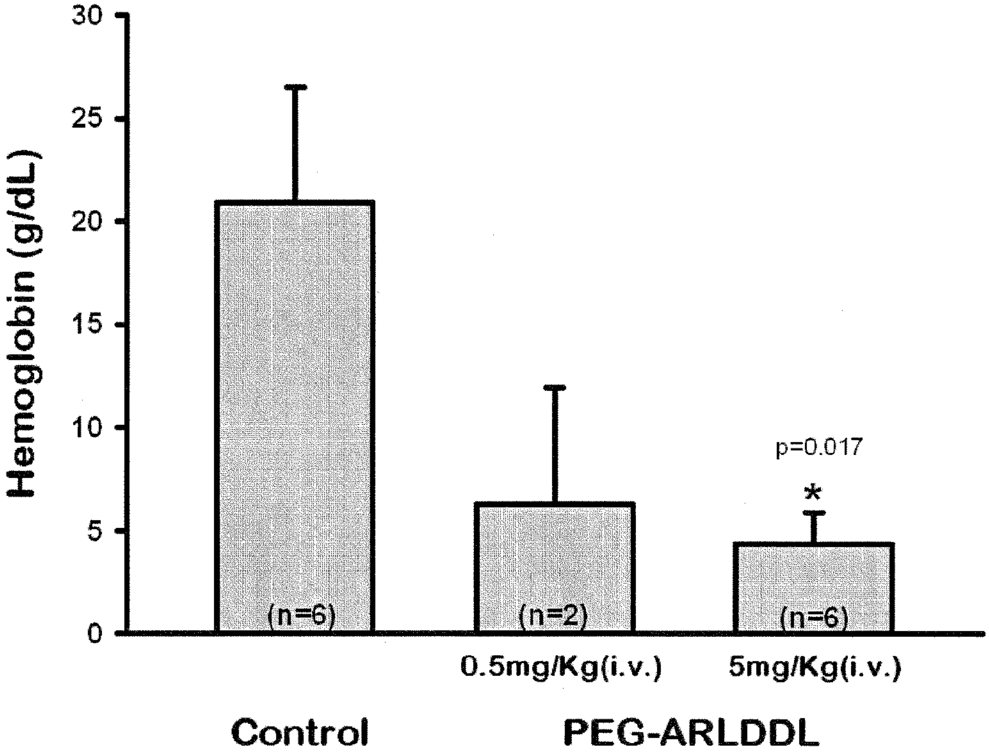
FIG 17B

FIG. 18
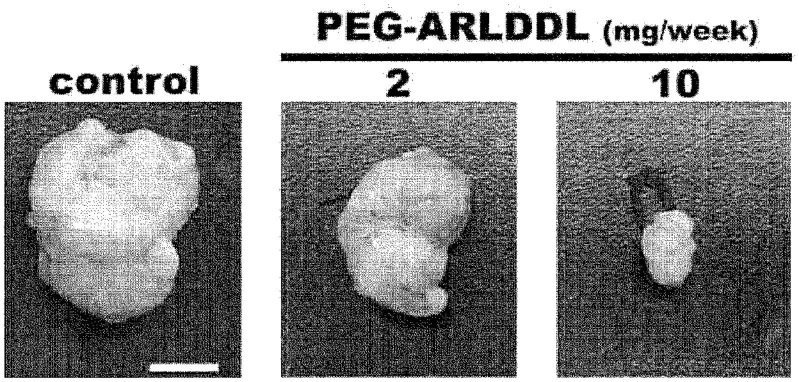
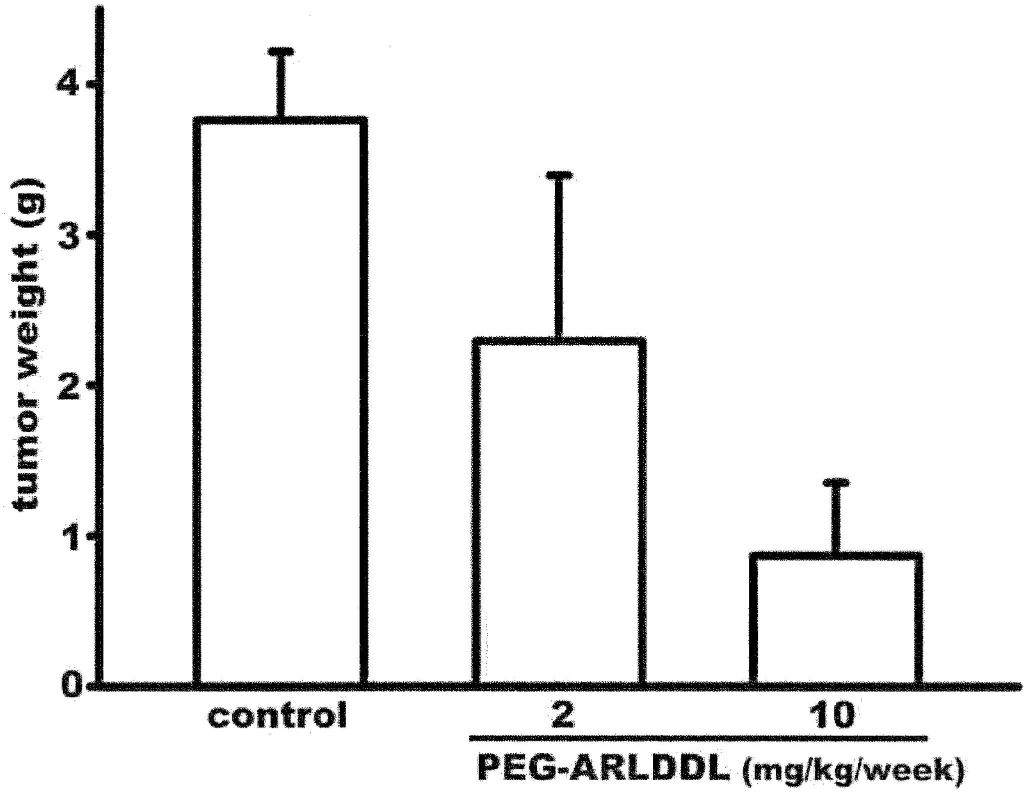
FIG. 19

FIG. 20
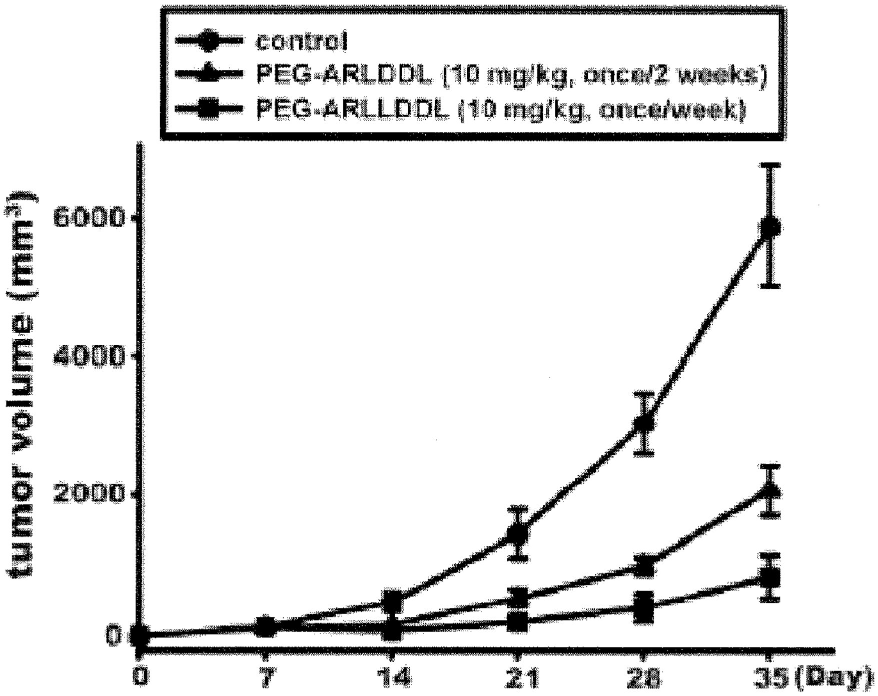
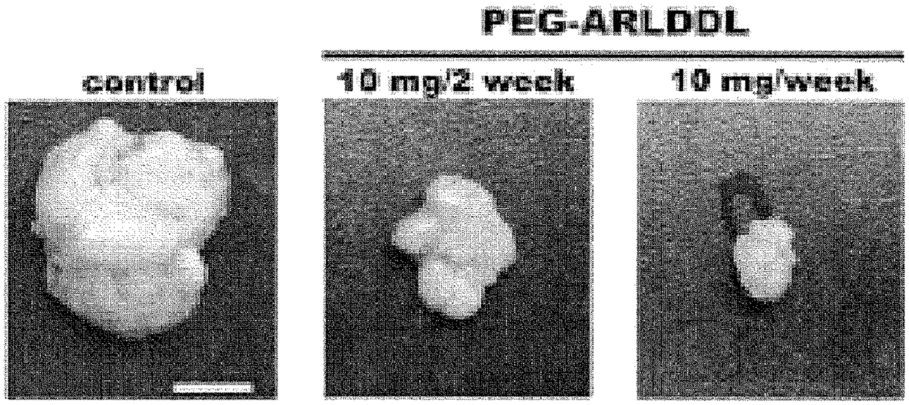
FIG. 21

FIG. 23
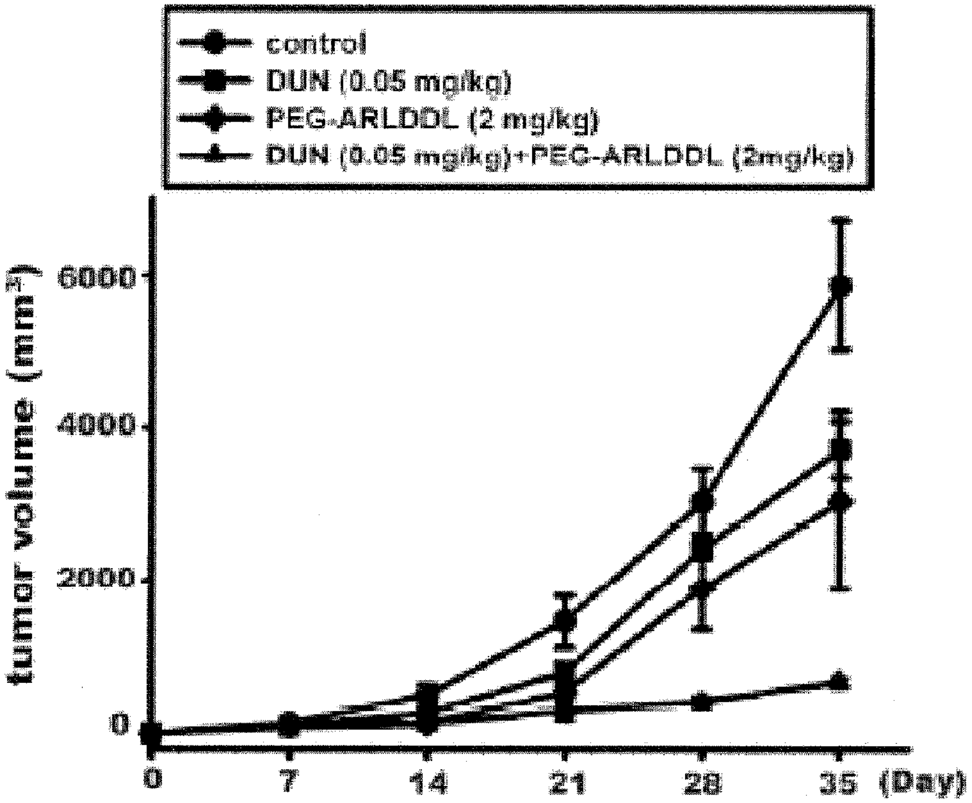
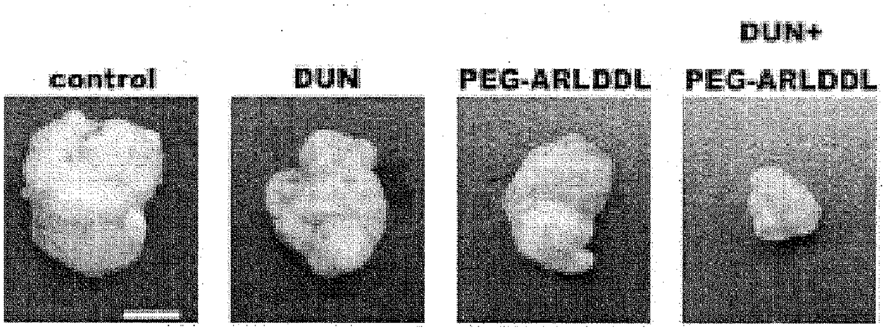
FIG. 24

FIG. 25
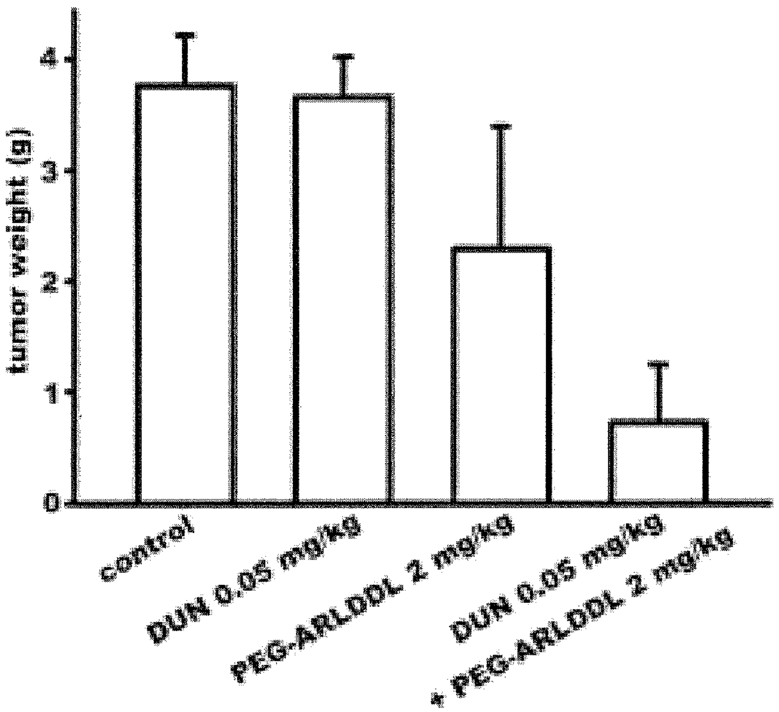
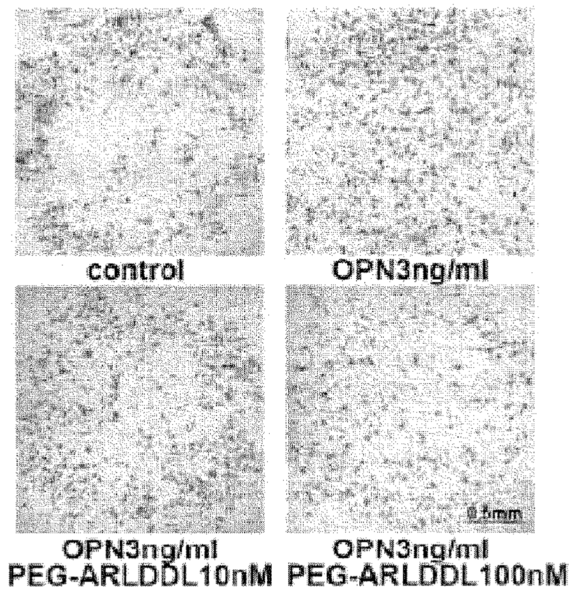
FIG. 26

```
                         SEQUENCE LISTING


<160> NUMBER OF SEQ ID NOS: 140

<210> SEQ ID NO 1
<211> LENGTH: 68
<212> TYPE: PRT
<213> ORGANISM: Colloselasma rhodostoma

<400> SEQUENCE: 1

Gly Lys Glu Cys Asp Cys Ser Ser Pro Glu Asn Pro Cys Cys Asp Ala
  1               5                  10                  15

Ala Thr Cys Lys Leu Arg Pro Gly Ala Gln Cys Gly Glu Gly Leu Cys
             20                  25                  30

Cys Glu Gln Cys Lys Phe Ser Arg Ala Gly Lys Ile Cys Arg Ile Pro
         35                  40                  45

Arg Gly Asp Met Pro Asp Asp Arg Cys Thr Gly Gln Ser Ala Asp Cys
     50                  55                  60

Pro Arg Tyr His
 65


<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide motif
```

<400> SEQUENCE: 2

Arg Gly Asp
1

<210> SEQ ID NO 3
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
gaattcgaat tccatcatca tcatcatcat catggtaagg aatgtgactg ttctt 55

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
ccgcggccgc ggttagtggt atcttggaca gtcagc 36

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
gaatcccaag acttgacatg ccag 24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
ctggcatgtc aagtcttggg attc 24

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
agaatcccaa gacacgacat gccagac 27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic primer -continued

<400> SEQUENCE: 8
gtctggcatg tcgtgtcttg ggattct 27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
agaatcccaa gaatcgacat gccagac 27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10
gtctggcatg tcgattcttg ggattct 27

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 11
tgtagaatcg ctagaggtga catg 24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 12
catgtcacct ctagcgattc taca 24

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 13
gtcacctctt gcgattctac ag 22

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 14
caagaggtga caacccagac gacag 25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ctgtcgtctg ggttgtcacc tcttg 25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
caagaggtga cgacccagac gacag 25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ctgtcgtctg ggtcgtcacc tcttg 25

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
caagaggtga cggtccagac gacagatg 28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
catctgtcgt ctggaccgtc acctcttg 28

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
caagaggtga cgacctagac gacagatg 28

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
catctgtcgt ctaggtcgtc acctcttg 28

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
caagaggtga cgacatggac gacagatg 28

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
catctgtcgt ccatgtcgtc acctcttg 28

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
caagaggtga cgacgtagac gacagatg 28

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
catctgtcgt ctacgtcgtc acctcttg 28

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
tattgccagc attgctgc 18

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
gactggttcc aattgacaag c 21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 28
gcaaatggca ttctgacatc c 21

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
rhodostomin peptide

<400> SEQUENCE: 29

Pro Arg Gly Asp Met Pro
1 5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
rhodostomin variant

<400> SEQUENCE: 30

Ala Arg Gly Asp Asp Pro
1 5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
rhodostomin variant

<400> SEQUENCE: 31

Ala Arg Gly Asp Asp Val
1 5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
rhodostomin variant

<400> SEQUENCE: 32

Ala Arg Gly Asp Asp Leu
1 5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic rhodostomin variant

<400> SEQUENCE: 33

Pro Arg Gly Asp Asp Leu
1 5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic rhodostomin variant

<400> SEQUENCE: 34

Ala Arg Gly Asp Asp Met
1 5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic rhodostomin variant

<400> SEQUENCE: 35

Pro Arg Gly Asp Asp Met
1 5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic rhodostomin variant
<220> FEATURE:
<223> OTHER INFORMATION: optional c-term pegylation

<400> SEQUENCE: 36

Pro Arg Leu Asp Met Pro
1 5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic rhodostomin variant

<400> SEQUENCE: 37

Pro Arg Leu Asp Asp Leu
1 5

<210> SEQ ID NO 38

<211> LENGTH: 6
<212> TYPE: PRT
<213> ORGANISM: Artificial Sequence
<220> FEATURE:
<223> OTHER INFORMATION: Description of Artificial Sequence: Synthetic
rhodostomin variant

<400> SEQUENCE: 38

Ala Arg Leu Asp Asp Leu
1 5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
rhodostomin variant

<400> SEQUENCE: 39

Pro Arg Ile Asp Met Pro
1 5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
rhodostomin variant

<400> SEQUENCE: 40

Pro Arg His Asp Met Pro
1 5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
rhodostomin variant

<400> SEQUENCE: 41

Pro Arg Gly Asp Asn Pro
1 5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
rhodostomin variant

<400> SEQUENCE: 42

Pro Arg Gly Asp Gly Pro
1 5

<210> SEQ ID NO 43
<211> LENGTH: 204
<212> TYPE: DNA
<213> ORGANISM: Artificial Sequence
<220> FEATURE:
<223> OTHER INFORMATION: Description of Artificial Sequence: Synthetic
rhodostomin variant

<400> SEQUENCE: 43
ggtaaggaat gtgactgttc ttctccagaa aacccatgtt gtgacgctgc tacttgtaag 60
ttgagaccag gtgctcaatg tggtgaaggt ttgtgttgtg aacaatgtaa gttctctaga 120
gctggtaaga tctgtagaat cccaagaggt gacatgccag acgacagatg tactggtcaa 180
tctgctgact gtccaagata ccac 204

<210> SEQ ID NO 44
<211> LENGTH: 204
<212> TYPE: DNA
<213> ORGANISM: Artificial Sequence
<220> FEATURE:
<223> OTHER INFORMATION: Description of Artificial Sequence: Synthetic rhodostomin variant

<400> SEQUENCE: 44
ggtaaggaat gtgactgttc ttctccagaa aacccatgtt gtgacgctgc tacttgtaag 60
ttgagaccag gtgctcaatg tggtgaaggt ttgtgttgtg aacaatgtaa gttctctaga 120
gctggtaaga tctgtagaat cgcaagaggt gacgacccag acgacagatg tactggtcaa 180
tctgctgact gtccaagata ccac 204

<210> SEQ ID NO 45
<211> LENGTH: 205
<212> TYPE: DNA
<213> ORGANISM: Artificial Sequence
<220> FEATURE:
<223> OTHER INFORMATION: Description of Artificial Sequence: Synthetic rhodostomin variant

<400> SEQUENCE: 45
gggtaaggaa tgtgactgtt cttctccaga aaacccatgt tgtgacgctg ctacttgtaa 60
gttgagacca ggtgctcaat gtggtgaagg tttgtgttgt gaacaatgta agttctctag 120
agctggtaag atctgtagaa tcgcaagagg tgacgacgta gacgacagat gtactggtca 180
atctgctgac tgtccaagat accac 205

<210> SEQ ID NO 46
<211> LENGTH: 204
<212> TYPE: DNA
<213> ORGANISM: Artificial Sequence
<220> FEATURE:
<223> OTHER INFORMATION: Description of Artificial Sequence: Synthetic rhodostomin variant

<400> SEQUENCE: 46
ggtaaggaat gtgactgttc ttctccagaa aacccatgtt gtgacgctgc tacttgtaag 60
ttgagaccag gtgctcaatg tggtgaaggt ttgtgttgtg aacaatgtaa gttctctaga 120
gctggtaaga tctgtagaat cgcaagaggt gacgacctag acgacagatg tactggtcaa 180
tctgctgact gtccaagata ccac 204

<210> SEQ ID NO 47
<211> LENGTH: 204
<212> TYPE: DNA
<213> ORGANISM: Artificial Sequence
<220> FEATURE:
<223> OTHER INFORMATION: Description of Artificial Sequence: Synthetic rhodostomin variant

<400> SEQUENCE: 47
ggtaaggaat gtgactgttc ttctccagaa aacccatgtt gtgacgctgc tacttgtaag 60
ttgagaccag gtgctcaatg tggtgaaggt ttgtgttgtg aacaatgtaa gttctctaga 120
gctggtaaga tctgtagaat cccaagaggt gacgacctag acgacagatg tactggtcaa 180
tctgctgact gtccaagata ccac 204

<210> SEQ ID NO 48
<211> LENGTH: 204
<212> TYPE: DNA
<213> ORGANISM: Artificial Sequence
<220> FEATURE:
<223> OTHER INFORMATION: Description of Artificial Sequence: Synthetic rhodostomin variant

<400> SEQUENCE: 48
ggtaaggaat gtgactgttc ttctccagaa aacccatgtt gtgacgctgc tacttgtaag 60
ttgagaccag gtgctcaatg tggtgaaggt ttgtgttgtg aacaatgtaa gttctctaga 120
gctggtaaga tctgtagaat cgcaagaggt gacgacatgg acgacagatg tactggtcaa 180
tctgctgact gtccaagata ccac 204

<210> SEQ ID NO 49
<211> LENGTH: 204
<212> TYPE: DNA
<213> ORGANISM: Artificial Sequence
<220> FEATURE:
<223> OTHER INFORMATION: Description of Artificial Sequence: Synthetic rhodostomin variant

<400> SEQUENCE: 49
ggtaaggaat gtgactgttc ttctccagaa aacccatgtt gtgacgctgc tacttgtaag 60
ttgagaccag gtgctcaatg tggtgaaggt ttgtgttgtg aacaatgtaa gttctctaga 120
gctggtaaga tctgtagaat cccaagaggt gacgacatgg acgacagatg tactggtcaa 180
tctgctgact gtccaagata ccac 204

<210> SEQ ID NO 50
<211> LENGTH: 204
<212> TYPE: DNA
<213> ORGANISM: Artificial Sequence
<220> FEATURE:
<223> OTHER INFORMATION: Description of Artificial Sequence: Synthetic rhodostomin variant

<400> SEQUENCE: 50
ggtaaggaat gtgactgttc ttctccagaa aacccatgtt gtgacgctgc tacttgtaag 60
ttgagaccag gtgctcaatg tggtgaaggt ttgtgttgtg aacaatgtaa gttctctaga 120
gctggtaaga tctgtagaat cccaagactt gacatgccag acgacagatg tactggtcaa 180
tctgctgact gtccaagata ccac 204

<210> SEQ ID NO 51
<211> LENGTH: 204
<212> TYPE: DNA
<213> ORGANISM: Artificial Sequence
<220> FEATURE:
<223> OTHER INFORMATION: Description of Artificial Sequence: Synthetic rhodostomin variant

<400> SEQUENCE: 51
ggtaaggaat gtgactgttc ttctccagaa aacccatgtt gtgacgctgc tacttgtaag 60
ttgagaccag gtgctcaatg tggtgaaggt ttgtgttgtg aacaatgtaa gttctctaga 120
gctggtaaga tctgtagaat cccaagactt gacgacctag acgacagatg tactggtcaa 180
tctgctgact gtccaagata ccac 204

-continued

<210> SEQ ID NO 52
<211> LENGTH: 204
<212> TYPE: DNA
<213> ORGANISM: Artificial Sequence
<220> FEATURE:
<223> OTHER INFORMATION: Description of Artificial Sequence: Synthetic
rhodostomin variant

<400> SEQUENCE: 52
ggtaaggaat gtgactgttc ttctccagaa aacccatgtt gtgacgctgc tacttgtaag 60
ttgagaccag gtgctcaatg tggtgaaggt ttgtgttgtg aacaatgtaa gttctctaga 120
gctggtaaga tctgtagaat cgcaagactt gacgacctag acgacagatg tactggtcaa 180
tctgctgact gtccaagata ccac 204

<210> SEQ ID NO 53
<211> LENGTH: 204
<212> TYPE: DNA
<213> ORGANISM: Artificial Sequence
<220> FEATURE:
<223> OTHER INFORMATION: Description of Artificial Sequence: Synthetic
rhodostomin variant

<400> SEQUENCE: 53
ggtaaggaat gtgactgttc ttctccagaa aacccatgtt gtgacgctgc tacttgtaag 60
ttgagaccag gtgctcaatg tggtgaaggt ttgtgttgtg aacaatgtaa gttctctaga 120
gctggtaaga tctgtagaat cccaagaatc gacatgccag acgacagatg tactggtcaa 180
tctgctgact gtccaagata ccac 204

<210> SEQ ID NO 54
<211> LENGTH: 204
<212> TYPE: DNA
<213> ORGANISM: Artificial Sequence
<220> FEATURE:
<223> OTHER INFORMATION: Description of Artificial Sequence: Synthetic
rhodostomin variant

<400> SEQUENCE: 54
ggtaaggaat gtgactgttc ttctccagaa aacccatgtt gtgacgctgc tacttgtaag 60
ttgagaccag gtgctcaatg tggtgaaggt ttgtgttgtg aacaatgtaa gttctctaga 120
gctggtaaga tctgtagaat cccaagacac gacatgccag acgacagatg tactggtcaa 180
tctgctgact gtccaagata ccac 204

<210> SEQ ID NO 55
<211> LENGTH: 204
<212> TYPE: DNA
<213> ORGANISM: Artificial Sequence
<220> FEATURE:
<223> OTHER INFORMATION: Description of Artificial Sequence: Synthetic
rhodostomin variant

<400> SEQUENCE: 55
ggtaaggaat gtgactgttc ttctccagaa aacccatgtt gtgacgctgc tacttgtaag 60
ttgagaccag gtgctcaatg tggtgaaggt ttgtgttgtg aacaatgtaa gttctctaga 120
gctggtaaga tctgtagaat cccaagaggt gacaacccag acgacagatg tactggtcaa 180
tctgctgact gtccaagata ccac 204

<210> SEQ ID NO 56
<211> LENGTH: 204
<212> TYPE: DNA
<213> ORGANISM: Artificial Sequence -continued
<220> FEATURE:
<223> OTHER INFORMATION: Description of Artificial Sequence: Synthetic
rhodostomin variant

<400> SEQUENCE: 56
ggtaaggaat gtgactgttc ttctccagaa aacccatgtt gtgacgctgc tacttgtaag 60
ttgagaccag gtgctcaatg tggtgaaggt ttgtgttgtg aacaatgtaa gttctctaga 120
gctggtaaga tctgtagaat cccaagaggt gacggtccag acgacagatg tactggtcaa 180
tctgctgact gtccaagata ccac 204

<210> SEQ ID NO 57
<211> LENGTH: 68
<212> TYPE: PRT
<213> ORGANISM: Artificial Sequence
<220> FEATURE:
<223> OTHER INFORMATION: Description of Artificial Sequence: Synthetic
rhodostomin variant

<400> SEQUENCE: 57

Gly Lys Glu Cys Asp Cys Ser Ser Pro Glu Asn Pro Cys Cys Asp Ala
1 5 10 15

Ala Thr Cys Lys Leu Arg Pro Gly Ala Gln Cys Gly Glu Gly Leu Cys
20 25 30

Cys Glu Gln Cys Lys Phe Ser Arg Ala Gly Lys Ile Cys Arg Ile Ala
35 40 45

Arg Gly Asp Asp Pro Asp Asp Arg Cys Thr Gly Gln Ser Ala Asp Cys
50 55 60

Pro Arg Tyr His
65

<210> SEQ ID NO 58
<211> LENGTH: 68
<212> TYPE: PRT
<213> ORGANISM: Artificial Sequence
<220> FEATURE:
<223> OTHER INFORMATION: Description of Artificial Sequence: Synthetic
rhodostomin variant

<400> SEQUENCE: 58

Gly Lys Glu Cys Asp Cys Ser Ser Pro Glu Asn Pro Cys Cys Asp Ala
1 5 10 15

Ala Thr Cys Lys Leu Arg Pro Gly Ala Gln Cys Gly Glu Gly Leu Cys
20 25 30

Cys Glu Gln Cys Lys Phe Ser Arg Ala Gly Lys Ile Cys Arg Ile Ala
35 40 45

Arg Gly Asp Asp Val Asp Asp Arg Cys Thr Gly Gln Ser Ala Asp Cys
50 55 60

Pro Arg Tyr His
65

<210> SEQ ID NO 59
<211> LENGTH: 68
<212> TYPE: PRT
<213> ORGANISM: Artificial Sequence
<220> FEATURE:
<223> OTHER INFORMATION: Description of Artificial Sequence: Synthetic
rhodostomin variant

<400> SEQUENCE: 59

Gly Lys Glu Cys Asp Cys Ser Ser Pro Glu Asn Pro Cys Cys Asp Ala
1 5 10 15

```
Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Asp Leu Asp Asp Arg Cys Thr Gly Gln Ser Ala Asp Cys
    50                  55                  60

Pro Arg Tyr His
65


<210> SEQ ID NO 60
<211> LENGTH: 68
<212> TYPE: PRT
<213> ORGANISM: Artificial Sequence
<220> FEATURE:
<223> OTHER INFORMATION: Description of Artificial Sequence: Synthetic
      rhodostomin variant

<400> SEQUENCE: 60

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Gly Asp Asp Leu Asp Asp Arg Cys Thr Gly Gln Ser Ala Asp Cys
    50                  55                  60

Pro Arg Tyr His
65


<210> SEQ ID NO 61
<211> LENGTH: 68
<212> TYPE: PRT
<213> ORGANISM: Artificial Sequence
<220> FEATURE:
<223> OTHER INFORMATION: Description of Artificial Sequence: Synthetic
      rhodostomin variant

<400> SEQUENCE: 61

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Asp Met Asp Asp Arg Cys Thr Gly Gln Ser Ala Asp Cys
    50                  55                  60

Pro Arg Tyr His
65


<210> SEQ ID NO 62
<211> LENGTH: 68
<212> TYPE: PRT
<213> ORGANISM: Artificial Sequence
<220> FEATURE:
<223> OTHER INFORMATION: Description of Artificial Sequence: Synthetic
      rhodostomin variant

<400> SEQUENCE: 62

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30
```

Cys Glu Gln Cys Lys Phe Ser Arg Ala Gly Lys Ile Cys Arg Ile Pro
35 40 45

Arg Gly Asp Asp Met Asp Asp Arg Cys Thr Gly Gln Ser Ala Asp Cys
50 55 60

Pro Arg Tyr His
65

<210> SEQ ID NO 63
<211> LENGTH: 68
<212> TYPE: PRT
<213> ORGANISM: Artificial Sequence
<220> FEATURE:
<223> OTHER INFORMATION: Description of Artificial Sequence: Synthetic rhodostomin variant

<400> SEQUENCE: 63

Gly Lys Glu Cys Asp Cys Ser Ser Pro Glu Asn Pro Cys Cys Asp Ala
1 5 10 15

Ala Thr Cys Lys Leu Arg Pro Gly Ala Gln Cys Gly Glu Gly Leu Cys
20 25 30

Cys Glu Gln Cys Lys Phe Ser Arg Ala Gly Lys Ile Cys Arg Ile Pro
35 40 45

Arg Leu Asp Met Pro Asp Asp Arg Cys Thr Gly Gln Ser Ala Asp Cys
50 55 60

Pro Arg Tyr His
65

<210> SEQ ID NO 64
<211> LENGTH: 68
<212> TYPE: PRT
<213> ORGANISM: Artificial Sequence
<220> FEATURE:
<223> OTHER INFORMATION: Description of Artificial Sequence: Synthetic rhodostomin variant

<400> SEQUENCE: 64

Gly Lys Glu Cys Asp Cys Ser Ser Pro Glu Asn Pro Cys Cys Asp Ala
1 5 10 15

Ala Thr Cys Lys Leu Arg Pro Gly Ala Gln Cys Gly Glu Gly Leu Cys
20 25 30

Cys Glu Gln Cys Lys Phe Ser Arg Ala Gly Lys Ile Cys Arg Ile Pro
35 40 45

Arg Leu Asp Asp Leu Asp Asp Arg Cys Thr Gly Gln Ser Ala Asp Cys
50 55 60

Pro Arg Tyr His
65

<210> SEQ ID NO 65
<211> LENGTH: 68
<212> TYPE: PRT
<213> ORGANISM: Artificial Sequence
<220> FEATURE:
<223> OTHER INFORMATION: Description of Artificial Sequence: Synthetic rhodostomin variant

<400> SEQUENCE: 65

Gly Lys Glu Cys Asp Cys Ser Ser Pro Glu Asn Pro Cys Cys Asp Ala
1 5 10 15

Ala Thr Cys Lys Leu Arg Pro Gly Ala Gln Cys Gly Glu Gly Leu Cys
20 25 30

Cys Glu Gln Cys Lys Phe Ser Arg Ala Gly Lys Ile Cys Arg Ile Ala

-continued

```
        35                  40                  45

Arg Leu Asp Asp Leu Asp Asp Arg Cys Thr Gly Gln Ser Ala Asp Cys
     50                  55                  60

Pro Arg Tyr His
 65


<210> SEQ ID NO 66
<211> LENGTH: 68
<212> TYPE: PRT
<213> ORGANISM: Artificial Sequence
<220> FEATURE:
<223> OTHER INFORMATION: Description of Artificial Sequence: Synthetic
      rhodostomin variant

<400> SEQUENCE: 66

Gly Lys Glu Cys Asp Cys Ser Ser Pro Glu Asn Pro Cys Cys Asp Ala
  1               5                  10                  15

Ala Thr Cys Lys Leu Arg Pro Gly Ala Gln Cys Gly Glu Gly Leu Cys
             20                  25                  30

Cys Glu Gln Cys Lys Phe Ser Arg Ala Gly Lys Ile Cys Arg Ile Pro
        35                  40                  45

Arg Ile Asp Met Pro Asp Asp Arg Cys Thr Gly Gln Ser Ala Asp Cys
     50                  55                  60

Pro Arg Tyr His
 65


<210> SEQ ID NO 67
<211> LENGTH: 68
<212> TYPE: PRT
<213> ORGANISM: Artificial Sequence
<220> FEATURE:
<223> OTHER INFORMATION: Description of Artificial Sequence: Synthetic
      rhodostomin variant

<400> SEQUENCE: 67

Gly Lys Glu Cys Asp Cys Ser Ser Pro Glu Asn Pro Cys Cys Asp Ala
  1               5                  10                  15

Ala Thr Cys Lys Leu Arg Pro Gly Ala Gln Cys Gly Glu Gly Leu Cys
             20                  25                  30

Cys Glu Gln Cys Lys Phe Ser Arg Ala Gly Lys Ile Cys Arg Ile Pro
        35                  40                  45

Arg His Asp Met Pro Asp Asp Arg Cys Thr Gly Gln Ser Ala Asp Cys
     50                  55                  60

Pro Arg Tyr His
 65


<210> SEQ ID NO 68
<211> LENGTH: 68
<212> TYPE: PRT
<213> ORGANISM: Artificial Sequence
<220> FEATURE:
<223> OTHER INFORMATION: Description of Artificial Sequence: Synthetic
      rhodostomin variant

<400> SEQUENCE: 68

Gly Lys Glu Cys Asp Cys Ser Ser Pro Glu Asn Pro Cys Cys Asp Ala
  1               5                  10                  15

Ala Thr Cys Lys Leu Arg Pro Gly Ala Gln Cys Gly Glu Gly Leu Cys
             20                  25                  30

Cys Glu Gln Cys Lys Phe Ser Arg Ala Gly Lys Ile Cys Arg Ile Pro
        35                  40                  45
```

```
Arg Gly Asp Asn Pro Asp Asp Arg Cys Thr Gly Gln Ser Ala Asp Cys
     50                  55                  60

Pro Arg Tyr His
 65


<210> SEQ ID NO 69
<211> LENGTH: 68
<212> TYPE: PRT
<213> ORGANISM: Artificial Sequence
<220> FEATURE:
<223> OTHER INFORMATION: Description of Artificial Sequence: Synthetic
      rhodostomin variant

<400> SEQUENCE: 69

Gly Lys Glu Cys Asp Cys Ser Ser Pro Glu Asn Pro Cys Cys Asp Ala
  1               5                  10                  15

Ala Thr Cys Lys Leu Arg Pro Gly Ala Gln Cys Gly Glu Gly Leu Cys
             20                  25                  30

Cys Glu Gln Cys Lys Phe Ser Arg Ala Gly Lys Ile Cys Arg Ile Pro
         35                  40                  45

Arg Gly Asp Gly Pro Asp Asp Arg Cys Thr Gly Gln Ser Ala Asp Cys
     50                  55                  60

Pro Arg Tyr His
 65


<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70

caagaggtga cgacctagac gacagatg                                        28


<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71

gtcacctctt gcgattctac ag                                              22


<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72

caagaggtga cgacatggac gacagatg                                        28


<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 73
gtcacctctt gcgattctac ag 22

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
caagacttga cgacctagac 20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
gtcgtcaagt cttgggattc 20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
caagacttga cgacctagac 20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
gtcgtcaagt cttgcgattc 20

<210> SEQ ID NO 78
<211> LENGTH: 73
<212> TYPE: PRT
<213> ORGANISM: Artificial Sequence
<220> FEATURE:
<223> OTHER INFORMATION: Description of Artificial Sequence: Synthetic disintegrin variant

<400> SEQUENCE: 78

```
Glu Ala Gly Glu Asp Cys Asp Cys Gly Ser Pro Ala Asn Pro Cys Cys
  1               5                  10                  15

Asp Ala Ala Thr Cys Lys Leu Leu Pro Gly Ala Gln Cys Gly Glu Gly
             20                  25                  30

Leu Cys Cys Asp Gln Cys Ser Phe Met Lys Lys Gly Thr Ile Cys Arg
         35                  40                  45

Arg Ala Arg Gly Asp Asp Leu Asp Asp Tyr Cys Asn Gly Ile Ser Ala
     50                  55                  60

Gly Cys Pro Arg Asn Pro Leu His Ala
```

65 70

<210> SEQ ID NO 79
<211> LENGTH: 219
<212> TYPE: DNA
<213> ORGANISM: Artificial Sequence
<220> FEATURE:
<223> OTHER INFORMATION: Description of Artificial Sequence: Synthetic disintegrin variant

<400> SEQUENCE: 79
gaagcgggcg aagattgcga ttgcggcagc ccggcgaacc cgtgctgcga tgcggcgacc 60
tgcaaactgc tgccgggcgc gcagtgcggc gaaggcctgt gctgcgatca gtgcagcttt 120
atgaaaaaag gcaccatttg ccgtcgtgcg cgtggcgatg atctggatga ttattgcaac 180
ggcattagcg cgggctgccc gcgtaacccg ctgcatgcg 219

<210> SEQ ID NO 80
<211> LENGTH: 71
<212> TYPE: PRT
<213> ORGANISM: Artificial Sequence
<220> FEATURE:
<223> OTHER INFORMATION: Description of Artificial Sequence: Synthetic disintegrin variant

<400> SEQUENCE: 80

Glu Ala Gly Glu Glu Cys Asp Cys Gly Ser Pro Glu Asn Pro Cys Cys
1 5 10 15

Asp Ala Ala Thr Cys Lys Leu Arg Pro Gly Ala Gln Cys Ala Glu Gly
20 25 30

Leu Cys Cys Asp Gln Cys Lys Phe Met Lys Glu Gly Thr Val Cys Arg
35 40 45

Ala Arg Gly Asp Asp Val Asn Asp Tyr Cys Asn Gly Ile Ser Ala Gly
50 55 60

Cys Pro Arg Asn Pro Phe His
65 70

<210> SEQ ID NO 81
<211> LENGTH: 213
<212> TYPE: DNA
<213> ORGANISM: Artificial Sequence
<220> FEATURE:
<223> OTHER INFORMATION: Description of Artificial Sequence: Synthetic disintegrin variant

<400> SEQUENCE: 81
gaagcgggcg aagaatgcga ttgcggcagc ccggaaaacc cgtgctgcga tgcggcgacc 60
tgcaaactgc gtccgggcgc gcagtgcgcg gaaggcctgt gctgcgatca gtgcaaattt 120
atgaaagaag gcaccgtgtg ccgtgcgcgt ggcgatgatg tgaacgatta ttgcaacggc 180
attagcgcgg gctgcccgcg taacccgttt cat 213

<210> SEQ ID NO 82
<211> LENGTH: 72
<212> TYPE: PRT
<213> ORGANISM: Artificial Sequence
<220> FEATURE:
<223> OTHER INFORMATION: Description of Artificial Sequence: Synthetic disintegrin variant

<400> SEQUENCE: 82

Ala Gly Glu Glu Cys Asp Cys Gly Ser Pro Ala Asn Pro Cys Cys Asp
1 5 10 15

```
Ala Ala Thr Cys Lys Leu Arg Pro Gly Ala Gln Cys Ala Glu Gly Leu
            20                  25                  30

Cys Cys Asp Gln Cys Arg Phe Ile Lys Lys Gly Lys Ile Cys Arg Arg
        35                  40                  45

Ala Arg Gly Asp Asn Pro Asp Asp Arg Cys Thr Gly Gln Ser Ala Asp
    50                  55                  60

Cys Pro Arg Asn His Phe His Ala
65                  70


<210> SEQ ID NO 83
<211> LENGTH: 216
<212> TYPE: DNA
<213> ORGANISM: Artificial Sequence
<220> FEATURE:
<223> OTHER INFORMATION: Description of Artificial Sequence: Synthetic
      disintegrin variant

<400> SEQUENCE: 83

gcgggcgaag aatgcgattg cggcagcccg gcgaacccgt gctgcgatgc ggcgacctgc      60

aaactgcgtc cgggcgcgca gtgcgcggaa ggcctgtgct gcgatcagtg ccgttttatt     120

aaaaaaggca aaatttgccg tcgtgcgcgt ggcgataacc cggatgatcg ttgcaccggc     180

cagagcgcgg attgcccgcg taaccatttt catgcg                               216


<210> SEQ ID NO 84
<211> LENGTH: 71
<212> TYPE: PRT
<213> ORGANISM: Artificial Sequence
<220> FEATURE:
<223> OTHER INFORMATION: Description of Artificial Sequence: Synthetic
      disintegrin variant

<400> SEQUENCE: 84

Glu Ala Gly Glu Glu Cys Asp Cys Gly Thr Pro Glu Asn Pro Cys Cys
1               5                   10                  15

Asp Ala Ala Thr Cys Lys Leu Arg Pro Gly Ala Gln Cys Ala Glu Gly
            20                  25                  30

Leu Cys Cys Asp Gln Cys Arg Phe Lys Gly Ala Gly Lys Ile Cys Arg
        35                  40                  45

Arg Ala Arg Gly Asp Asn Pro Asp Asp Arg Cys Thr Gly Gln Ser Ala
    50                  55                  60

Asp Cys Pro Arg Asn Arg Phe
65                  70


<210> SEQ ID NO 85
<211> LENGTH: 213
<212> TYPE: DNA
<213> ORGANISM: Artificial Sequence
<220> FEATURE:
<223> OTHER INFORMATION: Description of Artificial Sequence: Synthetic
      disintegrin variant

<400> SEQUENCE: 85

gaagcgggcg aagaatgcga ttgcggcacc ccggaaaacc cgtgctgcga tgcggcgacc      60

tgcaaactgc gtccgggcgc gcagtgcgcg gaaggcctgt gctgcgatca gtgccgtttt     120

aaaggcgcgg gcaaaatttg ccgtcgtgcg cgtggcgata acccggatga tcgttgcacc     180

ggccagagcg cggattgccc gcgtaaccgt ttt                                  213


<210> SEQ ID NO 86
<211> LENGTH: 83
<212> TYPE: PRT
```

<213> ORGANISM: Artificial Sequence
<220> FEATURE:
<223> OTHER INFORMATION: Description of Artificial Sequence: Synthetic
disintegrin variant

<400> SEQUENCE: 86

```
Ser Pro Pro Val Cys Gly Asn Lys Ile Leu Glu Gln Gly Glu Asp Cys
  1               5                  10                  15

Asp Cys Gly Ser Pro Ala Asn Cys Gln Asp Arg Cys Cys Asn Ala Ala
             20                  25                  30

Thr Cys Lys Leu Thr Pro Gly Ser Gln Cys Asn Tyr Gly Glu Cys Cys
         35                  40                  45

Asp Gln Cys Arg Phe Lys Lys Ala Gly Thr Val Cys Arg Ile Ala Arg
     50                  55                  60

Gly Asp Trp Asn Asp Asp Tyr Cys Thr Gly Lys Ser Ser Asp Cys Pro
 65                  70                  75                  80

Trp Asn His
```

<210> SEQ ID NO 87
<211> LENGTH: 249
<212> TYPE: DNA
<213> ORGANISM: Artificial Sequence
<220> FEATURE:
<223> OTHER INFORMATION: Description of Artificial Sequence: Synthetic
disintegrin variant

<400> SEQUENCE: 87

```
agcccgccgg tgtgcggcaa caaaattctg gaacagggcg aagattgcga ttgcggcagc     60

ccggcgaact gccaggatcg ttgctgcaac gcggcgacct gcaaactgac cccgggcagc    120

cagtgcaact atggcgaatg ctgcgatcag tgccgtttta aaaaagcggg caccgtgtgc    180

cgtattgcgc gtggcgattg gaacgatgat tattgcaccg gcaaaagcag cgattgcccg    240

tggaaccat                                                            249
```

<210> SEQ ID NO 88
<211> LENGTH: 72
<212> TYPE: PRT
<213> ORGANISM: Artificial Sequence
<220> FEATURE:
<223> OTHER INFORMATION: Description of Artificial Sequence: Synthetic
disintegrin variant

<400> SEQUENCE: 88

```
Glu Ala Gly Glu Glu Cys Asp Cys Gly Ser Pro Ala Asn Pro Cys Cys
  1               5                  10                  15

Asp Ala Ala Thr Cys Lys Leu Arg Pro Gly Ala Gln Cys Ala Glu Gly
             20                  25                  30

Leu Cys Cys Asp Gln Cys Arg Phe Ile Lys Lys Gly Lys Ile Cys Arg
         35                  40                  45

Arg Ala Arg Gly Asp Asn Pro Asp Asp Arg Cys Thr Gly Gln Ser Ala
     50                  55                  60

Asp Cys Pro Arg Asn Arg Phe His
 65                  70
```

<210> SEQ ID NO 89
<211> LENGTH: 216
<212> TYPE: DNA
<213> ORGANISM: Artificial Sequence
<220> FEATURE:
<223> OTHER INFORMATION: Description of Artificial Sequence: Synthetic
disintegrin variant

<400> SEQUENCE: 89
gaagcgggcg aagaatgcga ttgcggcagc ccggcgaacc cgtgctgcga tgcggcgacc 60
tgcaaactgc gtccgggcgc gcagtgcgcg gaaggcctgt gctgcgatca gtgccgtttt 120
attaaaaaag gcaaaatttg ccgtcgtgcg cgtggcgata acccggatga tcgttgcacc 180
ggccagagcg cggattgccc gcgtaaccgt tttcat 216

<210> SEQ ID NO 90
<211> LENGTH: 73
<212> TYPE: PRT
<213> ORGANISM: Artificial Sequence
<220> FEATURE:
<223> OTHER INFORMATION: Description of Artificial Sequence: Synthetic
disintegrin variant

<400> SEQUENCE: 90

Glu Ala Gly Glu Glu Cys Asp Cys Gly Thr Pro Glu Asn Pro Cys Cys
1 5 10 15

Asp Ala Ala Thr Cys Lys Leu Arg Pro Gly Ala Gln Cys Ala Asp Gly
20 25 30

Leu Cys Cys Asp Gln Cys Arg Phe Met Lys Lys Gly Thr Val Cys Arg
35 40 45

Val Ala Arg Gly Asp Trp Asn Asp Asp Thr Cys Thr Gly Gln Ser Ala
50 55 60

Asp Cys Pro Arg Asn Gly Leu Tyr Gly
65 70

<210> SEQ ID NO 91
<211> LENGTH: 219
<212> TYPE: DNA
<213> ORGANISM: Artificial Sequence
<220> FEATURE:
<223> OTHER INFORMATION: Description of Artificial Sequence: Synthetic
disintegrin variant

<400> SEQUENCE: 91
gaagcgggcg aagaatgcga ttgcggcacc ccggaaaacc cgtgctgcga tgcggcgacc 60
tgcaaactgc gtccgggcgc gcagtgcgcg gatggcctgt gctgcgatca gtgccgtttt 120
atgaaaaaag gcaccgtgtg ccgtgtggcg cgtggcgatt ggaacgatga tacctgcacc 180
ggccagagcg cggattgccc gcgtaacggc ctgtatggc 219

<210> SEQ ID NO 92
<211> LENGTH: 72
<212> TYPE: PRT
<213> ORGANISM: Artificial Sequence
<220> FEATURE:
<223> OTHER INFORMATION: Description of Artificial Sequence: Synthetic
disintegrin variant

<400> SEQUENCE: 92

Ala Gly Glu Glu Cys Asp Cys Gly Ser Pro Ala Asn Pro Cys Cys Asp
1 5 10 15

Ala Ala Thr Cys Lys Leu Arg Pro Gly Ala Gln Cys Ala Asp Gly Leu
20 25 30

Cys Cys Asp Gln Cys Arg Phe Ile Lys Lys Gly Thr Val Cys Arg Pro
35 40 45

Ala Arg Gly Asp Trp Asn Asp Asp Thr Cys Thr Gly Gln Ser Ala Asp
50 55 60

Cys Pro Arg Asn Gly Leu Tyr Gly
65 70

<210> SEQ ID NO 93
<211> LENGTH: 216
<212> TYPE: DNA
<213> ORGANISM: Artificial Sequence
<220> FEATURE:
<223> OTHER INFORMATION: Description of Artificial Sequence: Synthetic
disintegrin variant

<400> SEQUENCE: 93
gcgggcgaag aatgcgattg cggcagcccg gcgaacccgt gctgcgatgc ggcgacctgc 60
aaactgcgtc cgggcgcgca gtgcgcggat ggcctgtgct gcgatcagtg ccgttttatt 120
aaaaaaggca ccgtgtgccg tccggcgcgt ggcgattgga acgatgatac ctgcaccggc 180
cagagcgcgg attgcccgcg taacggcctg tatggc 216

<210> SEQ ID NO 94
<211> LENGTH: 72
<212> TYPE: PRT
<213> ORGANISM: Artificial Sequence
<220> FEATURE:
<223> OTHER INFORMATION: Description of Artificial Sequence: Synthetic
disintegrin variant

<400> SEQUENCE: 94

Ala Gly Glu Glu Cys Asp Cys Gly Ser Pro Ala Asn Pro Cys Cys Asp
1 5 10 15

Ala Ala Thr Cys Lys Leu Arg Pro Gly Ala Gln Cys Ala Asp Gly Leu
20 25 30

Cys Cys Asp Gln Cys Arg Phe Ile Lys Lys Gly Thr Val Cys Arg Pro
35 40 45

Ala Arg Gly Asp Trp Asn Asp Asp Thr Cys Thr Gly Gln Ser Ala Asp
50 55 60

Cys Pro Arg Asn Gly Leu Tyr Gly
65 70

<210> SEQ ID NO 95
<211> LENGTH: 216
<212> TYPE: DNA
<213> ORGANISM: Artificial Sequence
<220> FEATURE:
<223> OTHER INFORMATION: Description of Artificial Sequence: Synthetic
disintegrin variant

<400> SEQUENCE: 95
gcgggcgaag aatgcgattg cggcagcccg gcgaacccgt gctgcgatgc ggcgacctgc 60
aaactgcgtc cgggcgcgca gtgcgcggat ggcctgtgct gcgatcagtg ccgttttatt 120
aaaaaaggca ccgtgtgccg tccggcgcgt ggcgattgga acgatgatac ctgcaccggc 180
cagagcgcgg attgcccgcg taacggcctg tatggc 216

<210> SEQ ID NO 96
<211> LENGTH: 73
<212> TYPE: PRT
<213> ORGANISM: Artificial Sequence
<220> FEATURE:
<223> OTHER INFORMATION: Description of Artificial Sequence: Synthetic
disintegrin variant

<400> SEQUENCE: 96

Glu Ala Gly Glu Glu Cys Asp Cys Gly Ser Pro Glu Asn Pro Cys Cys
1 5 10 15

Asp Ala Ala Thr Cys Lys Leu Arg Pro Gly Ala Gln Cys Ala Asp Gly

-continued

```
            20                  25                  30

Leu Cys Cys Asp Gln Cys Arg Phe Ile Glu Glu Gly Ile Ile Cys Arg
        35                  40                  45

Arg Ala Arg Gly Asp Asp Leu Asp Asp Tyr Cys Asn Gly Ile Ser Gly
     50                  55                  60

Asp Cys Pro Arg Asn Pro Phe His Ala
 65                  70
```

<210> SEQ ID NO 97
<211> LENGTH: 219
<212> TYPE: DNA
<213> ORGANISM: Artificial Sequence
<220> FEATURE:
<223> OTHER INFORMATION: Description of Artificial Sequence: Synthetic disintegrin variant

<400> SEQUENCE: 97

```
gaagcgggcg aagaatgcga ttgcggcagc ccggaaaacc cgtgctgcga tgcggcgacc     60

tgcaaactgc gtccgggcgc gcagtgcgcg gatggcctgt gctgcgatca gtgccgtttt    120

attgaagaag gcattatttg ccgtcgtgcg cgtggcgatg atctggatga ttattgcaac    180

ggcattagcg gcgattgccc gcgtaacccg tttcatgcg                           219
```

<210> SEQ ID NO 98
<211> LENGTH: 70
<212> TYPE: PRT
<213> ORGANISM: Artificial Sequence
<220> FEATURE:
<223> OTHER INFORMATION: Description of Artificial Sequence: Synthetic disintegrin variant

<400> SEQUENCE: 98

```
Gly Glu Glu Cys Asp Cys Gly Ser Pro Ser Asn Pro Cys Cys Asp Ala
  1               5                  10                  15

Ala Thr Cys Lys Leu Arg Pro Gly Ala Gln Cys Ala Asp Gly Leu Cys
            20                  25                  30

Cys Asp Gln Cys Arg Phe Lys Lys Lys Arg Thr Ile Cys Arg Ile Ala
        35                  40                  45

Arg Gly Asp Phe Pro Asp Asp Arg Cys Thr Gly Leu Ser Asn Asp Cys
     50                  55                  60

Pro Arg Trp Asn Asp Leu
 65                  70
```

<210> SEQ ID NO 99
<211> LENGTH: 210
<212> TYPE: DNA
<213> ORGANISM: Artificial Sequence
<220> FEATURE:
<223> OTHER INFORMATION: Description of Artificial Sequence: Synthetic disintegrin variant

<400> SEQUENCE: 99

```
ggcgaagaat gcgattgcgg cagcccgagc aacccgtgct gcgatgcggc gacctgcaaa     60

ctgcgtccgg gcgcgcagtg cgcggatggc ctgtgctgcg atcagtgccg ttttaaaaaa    120

aaacgtacca tttgccgtat tgcgcgtggc gattttccgg atgatcgttg caccggcctg    180

agcaacgatt gcccgcgttg gaacgatctg                                     210
```

<210> SEQ ID NO 100
<211> LENGTH: 68
<212> TYPE: PRT
<213> ORGANISM: Artificial Sequence -continued
<220> FEATURE:
<223> OTHER INFORMATION: Description of Artificial Sequence: Synthetic
disintegrin variant

<400> SEQUENCE: 100

```
Gly Glu Glu Cys Asp Cys Gly Ser Pro Ser Asn Pro Cys Cys Asp Ala
  1               5                  10                  15

Ala Thr Cys Lys Leu Arg Pro Gly Ala Gln Cys Ala Asp Gly Leu Cys
             20                  25                  30

Cys Asp Gln Cys Arg Phe Lys Lys Lys Arg Thr Ile Cys Arg Arg Ala
         35                  40                  45

Arg Gly Asp Asn Pro Asp Asp Arg Cys Thr Gly Gln Ser Ala Asp Cys
     50                  55                  60

Pro Arg Asn Ser
 65
```

<210> SEQ ID NO 101
<211> LENGTH: 204
<212> TYPE: DNA
<213> ORGANISM: Artificial Sequence
<220> FEATURE:
<223> OTHER INFORMATION: Description of Artificial Sequence: Synthetic
disintegrin variant

<400> SEQUENCE: 101

```
ggcgaagaat gcgattgcgg cagcccgagc aacccgtgct gcgatgcggc gacctgcaaa     60

ctgcgtccgg gcgcgcagtg cgcggatggc ctgtgctgcg atcagtgccg ttttaaaaaa    120

aaacgtacca tttgccgtcg tgcgcgtggc gataacccgg atgatcgttg caccggccag    180

agcgcggatt gcccgcgtaa cagc                                           204
```

<210> SEQ ID NO 102
<211> LENGTH: 71
<212> TYPE: PRT
<213> ORGANISM: Artificial Sequence
<220> FEATURE:
<223> OTHER INFORMATION: Description of Artificial Sequence: Synthetic
disintegrin variant

<400> SEQUENCE: 102

```
Glu Ala Gly Glu Glu Cys Asp Cys Gly Ser Pro Gly Asn Pro Cys Cys
  1               5                  10                  15

Asp Ala Ala Thr Cys Lys Leu Arg Gln Gly Ala Gln Cys Ala Glu Gly
             20                  25                  30

Leu Cys Cys Asp Gln Cys Arg Phe Met Lys Lys Gly Thr Val Cys Arg
         35                  40                  45

Ile Ala Arg Gly Asp Asp Met Asp Asp Tyr Cys Asn Gly Ile Ser Ala
     50                  55                  60

Gly Cys Pro Arg Asn Pro Phe
 65                  70
```

<210> SEQ ID NO 103
<211> LENGTH: 213
<212> TYPE: DNA
<213> ORGANISM: Artificial Sequence
<220> FEATURE:
<223> OTHER INFORMATION: Description of Artificial Sequence: Synthetic
disintegrin variant

<400> SEQUENCE: 103

```
gaagcgggcg aagaatgcga ttgcggcagc ccgggcaacc cgtgctgcga tgcggcgacc     60

tgcaaactgc gtcagggcgc gcagtgcgcg gaaggcctgt gctgcgatca gtgccgtttt    120
```

```
atgaaaaaag gcaccgtgtg ccgtattgcg cgtggcgatg atatggatga ttattgcaac    180

ggcattagcg cgggctgccc gcgtaacccg ttt                                 213
```

<210> SEQ ID NO 104
<211> LENGTH: 73
<212> TYPE: PRT
<213> ORGANISM: Artificial Sequence
<220> FEATURE:
<223> OTHER INFORMATION: Description of Artificial Sequence: Synthetic disintegrin variant

<400> SEQUENCE: 104

```
Glu Ala Gly Glu Asp Cys Asp Cys Gly Ala Pro Ala Asn Pro Cys Cys
  1               5                  10                  15

Asp Ala Ala Thr Cys Lys Leu Arg Pro Gly Ala Gln Cys Ala Glu Gly
             20                  25                  30

Leu Cys Cys Asp Gln Cys Arg Phe Met Lys Glu Gly Thr Ile Cys Arg
         35                  40                  45

Met Ala Arg Gly Asp Asp Met Asp Asp Tyr Cys Asn Gly Ile Ser Ala
     50                  55                  60

Gly Cys Pro Arg Asn Pro Phe His Ala
 65                  70
```

<210> SEQ ID NO 105
<211> LENGTH: 219
<212> TYPE: DNA
<213> ORGANISM: Artificial Sequence
<220> FEATURE:
<223> OTHER INFORMATION: Description of Artificial Sequence: Synthetic disintegrin variant

<400> SEQUENCE: 105

```
gaagcgggcg aagattgcga ttgcggcgcg ccggcgaacc cgtgctgcga tgcggcgacc     60

tgcaaactgc gtccgggcgc gcagtgcgcg gaaggcctgt gctgcgatca gtgccgtttt    120

atgaaagaag gcaccatttg ccgtatggcg cgtggcgatg atatggatga ttattgcaac    180

ggcattagcg cgggctgccc gcgtaacccg tttcatgcg                           219
```

<210> SEQ ID NO 106
<211> LENGTH: 73
<212> TYPE: PRT
<213> ORGANISM: Artificial Sequence
<220> FEATURE:
<223> OTHER INFORMATION: Description of Artificial Sequence: Synthetic disintegrin variant

<400> SEQUENCE: 106

```
Glu Ala Gly Glu Glu Cys Asp Cys Gly Thr Pro Gly Asn Pro Cys Cys
  1               5                  10                  15

Asp Ala Ala Thr Cys Lys Leu Arg Pro Gly Ala Gln Cys Ala Glu Gly
             20                  25                  30

Leu Cys Cys Asp Gln Cys Arg Phe Lys Gly Ala Gly Lys Ile Cys Arg
         35                  40                  45

Arg Ala Arg Gly Asp Asn Pro Asp Asp Arg Cys Thr Gly Gln Ser Ala
     50                  55                  60

Asp Cys Pro Arg Asn Arg Phe His Ala
 65                  70
```

<210> SEQ ID NO 107
<211> LENGTH: 219
<212> TYPE: DNA

<213> ORGANISM: Artificial Sequence
<220> FEATURE:
<223> OTHER INFORMATION: Description of Artificial Sequence: Synthetic disintegrin variant

<400> SEQUENCE: 107
gaagcgggcg aagaatgcga ttgcggcacc ccgggcaacc cgtgctgcga tgcggcgacc 60
tgcaaactgc gtccgggcgc gcagtgcgcg gaaggcctgt gctgcgatca gtgccgtttt 120
aaaggcgcgg gcaaaatttg ccgtcgtgcg cgtggcgata acccggatga tcgttgcacc 180
ggccagagcg cggattgccc gcgtaaccgt tttcatgcg 219

<210> SEQ ID NO 108
<211> LENGTH: 73
<212> TYPE: PRT
<213> ORGANISM: Artificial Sequence
<220> FEATURE:
<223> OTHER INFORMATION: Description of Artificial Sequence: Synthetic disintegrin variant

<400> SEQUENCE: 108

Glu Ala Gly Glu Glu Cys Asp Cys Gly Thr Pro Gly Asn Pro Cys Cys
1 5 10 15

Asp Ala Ala Thr Cys Lys Leu Arg Pro Gly Ala Gln Cys Ala Glu Gly
20 25 30

Leu Cys Cys Asp Gln Cys Arg Phe Met Lys Glu Gly Thr Val Cys Arg
35 40 45

Arg Ala Arg Gly Asp Asp Met Asp Asp Tyr Cys Asn Gly Ile Ser Ala
50 55 60

Gly Cys Pro Arg Asn Pro Phe His Ala
65 70

<210> SEQ ID NO 109
<211> LENGTH: 219
<212> TYPE: DNA
<213> ORGANISM: Artificial Sequence
<220> FEATURE:
<223> OTHER INFORMATION: Description of Artificial Sequence: Synthetic disintegrin variant

<400> SEQUENCE: 109
gaagcgggcg aagaatgcga ttgcggcacc ccgggcaacc cgtgctgcga tgcggcgacc 60
tgcaaactgc gtccgggcgc gcagtgcgcg gaaggcctgt gctgcgatca gtgccgtttt 120
atgaaagaag gcaccgtgtg ccgtcgtgcg cgtggcgatg atatggatga ttattgcaac 180
ggcattagcg cgggctgccc gcgtaacccg tttcatgcg 219

<210> SEQ ID NO 110
<211> LENGTH: 68
<212> TYPE: PRT
<213> ORGANISM: Artificial Sequence
<220> FEATURE:
<223> OTHER INFORMATION: Description of Artificial Sequence: Synthetic disintegrin variant

<400> SEQUENCE: 110

Gly Lys Glu Cys Asp Cys Ser Ser Pro Glu Asn Pro Cys Cys Asp Ala
1 5 10 15

Ala Thr Cys Lys Leu Arg Pro Gly Ala Gln Cys Gly Glu Gly Leu Cys
20 25 30

Cys Glu Gln Cys Lys Phe Ser Arg Ala Gly Lys Ile Cys Arg Ile Pro
35 40 45

```
Arg Gly Asp Met Pro Asp Asp Arg Cys Thr Gly Gln Ser Ala Asp Cys
     50                  55                  60

Pro Arg Tyr His
 65


<210> SEQ ID NO 111
<211> LENGTH: 204
<212> TYPE: DNA
<213> ORGANISM: Artificial Sequence
<220> FEATURE:
<223> OTHER INFORMATION: Description of Artificial Sequence: Synthetic
      disintegrin variant

<400> SEQUENCE: 111

ggcaaagaat gcgattgcag cagcccggaa aacccgtgct gcgatgcggc gacctgcaaa     60

ctgcgtccgg gcgcgcagtg cggcgaaggc ctgtgctgcg aacagtgcaa atttagccgt    120

gcgggcaaaa tttgccgtat tccgcgtggc gatatgccgg atgatcgttg caccggccag    180

agcgcggatt gcccgcgtta tcat                                            204


<210> SEQ ID NO 112
<211> LENGTH: 73
<212> TYPE: PRT
<213> ORGANISM: Artificial Sequence
<220> FEATURE:
<223> OTHER INFORMATION: Description of Artificial Sequence: Synthetic
      disintegrin variant

<400> SEQUENCE: 112

Glu Ala Gly Glu Glu Cys Asp Cys Gly Ala Pro Ala Asn Pro Cys Cys
  1               5                  10                  15

Asp Ala Ala Thr Cys Lys Leu Arg Pro Gly Ala Gln Cys Ala Glu Gly
             20                  25                  30

Leu Cys Cys Asp Gln Cys Arg Phe Ile Lys Lys Gly Lys Ile Cys Arg
         35                  40                  45

Arg Ala Arg Gly Asp Asn Pro Asp Asp Arg Cys Thr Gly Gln Ser Ala
     50                  55                  60

Asp Cys Pro Arg Asn Gly Tyr Tyr Gly
 65                  70


<210> SEQ ID NO 113
<211> LENGTH: 219
<212> TYPE: DNA
<213> ORGANISM: Artificial Sequence
<220> FEATURE:
<223> OTHER INFORMATION: Description of Artificial Sequence: Synthetic
      disintegrin variant

<400> SEQUENCE: 113

gaagcgggcg aagaatgcga ttgcggcgcg ccggcgaacc cgtgctgcga tgcggcgacc     60

tgcaaactgc gtccgggcgc gcagtgcgcg gaaggcctgt gctgcgatca gtgccgtttt    120

attaaaaaag gcaaaatttg ccgtcgtgcg cgtggcgata acccggatga tcgttgcacc    180

ggccagagcg cggattgccc gcgtaacggc tattatggc                            219


<210> SEQ ID NO 114
<211> LENGTH: 73
<212> TYPE: PRT
<213> ORGANISM: Artificial Sequence
<220> FEATURE:
<223> OTHER INFORMATION: Description of Artificial Sequence: Synthetic
      disintegrin variant

<400> SEQUENCE: 114
```

```
Glu Ala Gly Glu Glu Cys Asp Cys Gly Ser Pro Ala Asn Pro Cys Cys
  1               5                  10                  15

Asp Ala Ala Thr Cys Lys Leu Arg Pro Gly Ala Gln Cys Ala Asp Gly
            20                  25                  30

Leu Cys Cys Asp Gln Cys Arg Phe Ile Lys Lys Gly Thr Val Cys Arg
        35                  40                  45

Val Ala Arg Gly Asp Trp Asn Asp Asp Thr Cys Thr Gly Gln Ser Ala
    50                  55                  60

Asp Cys Pro Arg Asn Gly Leu Tyr Gly
65                  70
```

```
<210> SEQ ID NO 115
<211> LENGTH: 219
<212> TYPE: DNA
<213> ORGANISM: Artificial Sequence
<220> FEATURE:
<223> OTHER INFORMATION: Description of Artificial Sequence: Synthetic
      disintegrin variant

<400> SEQUENCE: 115

gaagcgggcg aagaatgcga ttgcggcagc ccggcgaacc cgtgctgcga tgcggcgacc      60

tgcaaactgc gtccgggcgc gcagtgcgcg gatggcctgt gctgcgatca gtgccgtttt     120

attaaaaaag gcaccgtgtg ccgtgtggcg cgtggcgatt ggaacgatga tacctgcacc     180

ggccagagcg cggattgccc gcgtaacggc ctgtatggc                            219
```

```
<210> SEQ ID NO 116
<211> LENGTH: 73
<212> TYPE: PRT
<213> ORGANISM: Artificial Sequence
<220> FEATURE:
<223> OTHER INFORMATION: Description of Artificial Sequence: Synthetic
      disintegrin variant

<400> SEQUENCE: 116

Glu Ala Gly Ile Glu Cys Asp Cys Gly Ser Pro Glu Asn Pro Cys Cys
  1               5                  10                  15

Asp Ala Ala Thr Cys Lys Leu Arg Pro Gly Ala Gln Cys Ala Asp Gly
            20                  25                  30

Leu Cys Cys Asp Gln Cys Arg Phe Ile Lys Lys Gly Lys Ile Cys Arg
        35                  40                  45

Arg Ala Arg Gly Asp Asn Pro Asp Asp Arg Cys Thr Gly Gln Ser Ala
    50                  55                  60

Asp Cys Pro Arg Asn Arg Phe His Ala
65                  70
```

```
<210> SEQ ID NO 117
<211> LENGTH: 219
<212> TYPE: DNA
<213> ORGANISM: Artificial Sequence
<220> FEATURE:
<223> OTHER INFORMATION: Description of Artificial Sequence: Synthetic
      disintegrin variant

<400> SEQUENCE: 117

gaagcgggca ttgaatgcga ttgcggcagc ccggaaaacc cgtgctgcga tgcggcgacc      60

tgcaaactgc gtccgggcgc gcagtgcgcg gatggcctgt gctgcgatca gtgccgtttt     120

attaaaaaag gcaaaatttg ccgtcgtgcg cgtggcgata acccggatga tcgttgcacc     180

ggccagagcg cggattgccc gcgtaaccgt tttcatgcg                            219
```

<210> SEQ ID NO 118
<211> LENGTH: 73
<212> TYPE: PRT
<213> ORGANISM: Artificial Sequence
<220> FEATURE:
<223> OTHER INFORMATION: Description of Artificial Sequence: Synthetic disintegrin variant

<400> SEQUENCE: 118

```
Glu Ala Gly Glu Glu Cys Asp Cys Gly Ser Pro Gly Asn Pro Cys Cys
  1               5                  10                  15

Asp Ala Ala Thr Cys Lys Leu Arg Gln Gly Ala Gln Cys Ala Glu Gly
             20                  25                  30

Leu Cys Cys Asp Gln Cys Arg Phe Met Lys Glu Gly Thr Ile Cys Arg
         35                  40                  45

Arg Ala Arg Gly Asp Asp Leu Asp Asp Tyr Cys Asn Gly Ile Ser Ala
     50                  55                  60

Gly Cys Pro Arg Asn Pro Phe His Ala
 65                  70
```

<210> SEQ ID NO 119
<211> LENGTH: 219
<212> TYPE: DNA
<213> ORGANISM: Artificial Sequence
<220> FEATURE:
<223> OTHER INFORMATION: Description of Artificial Sequence: Synthetic disintegrin variant

<400> SEQUENCE: 119

```
gaagcgggcg aagaatgcga ttgcggcagc ccgggcaacc cgtgctgcga tgcggcgacc      60

tgcaaactgc gtcagggcgc gcagtgcgcg gaaggcctgt gctgcgatca gtgccgtttt     120

atgaaagaag gcaccatttg ccgtcgtgcg cgtggcgatg atctggatga ttattgcaac     180

ggcattagcg cgggctgccc gcgtaacccg tttcatgcg                            219
```

<210> SEQ ID NO 120
<211> LENGTH: 73
<212> TYPE: PRT
<213> ORGANISM: Artificial Sequence
<220> FEATURE:
<223> OTHER INFORMATION: Description of Artificial Sequence: Synthetic disintegrin variant

<400> SEQUENCE: 120

```
Glu Ala Gly Glu Glu Cys Asp Cys Gly Ala Pro Ala Asn Pro Cys Cys
  1               5                  10                  15

Asp Ala Ala Thr Cys Lys Leu Arg Pro Gly Ala Gln Cys Ala Glu Gly
             20                  25                  30

Leu Cys Cys Asp Gln Cys Arg Phe Met Lys Glu Gly Thr Ile Cys Arg
         35                  40                  45

Met Ala Arg Gly Asp Asp Met Asp Asp Tyr Cys Asn Gly Ile Ser Ala
     50                  55                  60

Gly Cys Pro Arg Asn Pro Phe His Ala
 65                  70
```

<210> SEQ ID NO 121
<211> LENGTH: 219
<212> TYPE: DNA
<213> ORGANISM: Artificial Sequence
<220> FEATURE:
<223> OTHER INFORMATION: Description of Artificial Sequence: Synthetic disintegrin variant

<400> SEQUENCE: 121
gaagcgggcg aagaatgcga ttgcggcgcg ccggcgaacc cgtgctgcga tgcggcgacc 60
tgcaaactgc gtccgggcgc gcagtgcgcg gaaggcctgt gctgcgatca gtgccgtttt 120
atgaaagaag gcaccatttg ccgtatggcg cgtggcgatg atatggatga ttattgcaac 180
ggcattagcg cgggctgccc gcgtaacccg tttcatgcg 219

<210> SEQ ID NO 122
<211> LENGTH: 73
<212> TYPE: PRT
<213> ORGANISM: Artificial Sequence
<220> FEATURE:
<223> OTHER INFORMATION: Description of Artificial Sequence: Synthetic
disintegrin variant

<400> SEQUENCE: 122

Glu Ala Gly Glu Glu Cys Asp Cys Gly Ser Pro Ala Asn Pro Cys Cys
1 5 10 15

Asp Ala Ala Thr Cys Lys Leu Arg Pro Gly Ala Gln Cys Ala Asp Gly
20 25 30

Leu Cys Cys Asp Gln Cys Arg Phe Met Lys Lys Gly Thr Val Cys Arg
35 40 45

Val Ala Arg Gly Asp Trp Asn Asp Asp Thr Cys Thr Gly Gln Ser Ala
50 55 60

Asp Cys Pro Arg Asn Gly Leu Tyr Gly
65 70

<210> SEQ ID NO 123
<211> LENGTH: 219
<212> TYPE: DNA
<213> ORGANISM: Artificial Sequence
<220> FEATURE:
<223> OTHER INFORMATION: Description of Artificial Sequence: Synthetic
disintegrin variant

<400> SEQUENCE: 123
gaagcgggcg aagaatgcga ttgcggcagc ccggcgaacc cgtgctgcga tgcggcgacc 60
tgcaaactgc gtccgggcgc gcagtgcgcg gatggcctgt gctgcgatca gtgccgtttt 120
atgaaaaaag gcaccgtgtg ccgtgtggcg cgtggcgatt ggaacgatga tacctgcacc 180
ggccagagcg cggattgccc gcgtaacggc ctgtatggc 219

<210> SEQ ID NO 124
<211> LENGTH: 70
<212> TYPE: PRT
<213> ORGANISM: Artificial Sequence
<220> FEATURE:
<223> OTHER INFORMATION: Description of Artificial Sequence: Synthetic
disintegrin variant

<400> SEQUENCE: 124

Gly Glu Glu Cys Asp Cys Gly Ser Pro Ser Asn Pro Cys Cys Asp Ala
1 5 10 15

Ala Thr Cys Lys Leu Arg Pro Gly Ala Gln Cys Ala Asp Gly Leu Cys
20 25 30

Cys Asp Gln Cys Arg Phe Lys Lys Lys Arg Thr Ile Cys Arg Ile Ala
35 40 45

Arg Gly Asp Phe Pro Asp Asp Arg Cys Thr Gly Gln Ser Ala Asp Cys
50 55 60

Pro Arg Trp Asn Gly Leu
65 70

<210> SEQ ID NO 125
<211> LENGTH: 210
<212> TYPE: DNA
<213> ORGANISM: Artificial Sequence
<220> FEATURE:
<223> OTHER INFORMATION: Description of Artificial Sequence: Synthetic disintegrin variant

<400> SEQUENCE: 125
ggcgaagaat gcgattgcgg cagcccgagc aacccgtgct gcgatgcggc gacctgcaaa 60
ctgcgtccgg gcgcgcagtg cgcggatggc ctgtgctgcg atcagtgccg ttttaaaaaa 120
aaacgtacca tttgccgtat tgcgcgtggc gattttccgg atgatcgttg caccggccag 180
agcgcggatt gcccgcgttg gaacggcctg 210

<210> SEQ ID NO 126
<211> LENGTH: 73
<212> TYPE: PRT
<213> ORGANISM: Artificial Sequence
<220> FEATURE:
<223> OTHER INFORMATION: Description of Artificial Sequence: Synthetic disintegrin variant

<400> SEQUENCE: 126

Glu Ala Gly Glu Glu Cys Asp Cys Gly Ser Pro Glu Asn Pro Cys Cys
1 5 10 15

Asp Ala Ala Thr Cys Lys Leu Arg Pro Gly Ala Gln Cys Ala Glu Gly
20 25 30

Leu Cys Cys Asp Gln Cys Arg Phe Lys Lys Lys Arg Thr Ile Cys Arg
35 40 45

Arg Ala Arg Gly Asp Asn Pro Asp Asp Arg Cys Thr Gly Gln Ser Ala
50 55 60

Asp Cys Pro Arg Asn Gly Leu Tyr Gly
65 70

<210> SEQ ID NO 127
<211> LENGTH: 219
<212> TYPE: DNA
<213> ORGANISM: Artificial Sequence
<220> FEATURE:
<223> OTHER INFORMATION: Description of Artificial Sequence: Synthetic disintegrin variant

<400> SEQUENCE: 127
gaagcgggcg aagaatgcga ttgcggcagc ccggaaaacc cgtgctgcga tgcggcgacc 60
tgcaaactgc gtccgggcgc gcagtgcgcg gaaggcctgt gctgcgatca gtgccgtttt 120
aaaaaaaaac gtaccatttg ccgtcgtgcg cgtggcgata acccggatga tcgttgcacc 180
ggccagagcg cggattgccc gcgtaacggc ctgtatggc 219

<210> SEQ ID NO 128
<211> LENGTH: 73
<212> TYPE: PRT
<213> ORGANISM: Artificial Sequence
<220> FEATURE:
<223> OTHER INFORMATION: Description of Artificial Sequence: Synthetic disintegrin variant

<400> SEQUENCE: 128

Glu Ala Gly Glu Glu Cys Asp Cys Gly Ser Pro Glu Asn Pro Cys Cys
1 5 10 15

Asp Ala Ala Thr Cys Lys Leu Arg Pro Gly Ala Gln Cys Ala Glu Gly

-continued

```
            20                  25                  30

Leu Cys Cys Asp Gln Cys Arg Phe Lys Lys Lys Arg Thr Ile Cys Arg
        35                  40                  45

Arg Ala Arg Gly Asp Asn Pro Asp Asp Arg Cys Thr Gly Gln Ser Ala
    50                  55                  60

Asp Cys Pro Arg Asn Gly Leu Tyr Gly
65                  70


<210> SEQ ID NO 129
<211> LENGTH: 219
<212> TYPE: DNA
<213> ORGANISM: Artificial Sequence
<220> FEATURE:
<223> OTHER INFORMATION: Description of Artificial Sequence: Synthetic
      disintegrin variant

<400> SEQUENCE: 129

gaagcgggcg aagaatgcga ttgcggcagc ccggaaaacc cgtgctgcga tgcggcgacc     60

tgcaaactgc gtccgggcgc gcagtgcgcg gaaggcctgt gctgcgatca gtgccgtttt    120

aaaaaaaaac gtaccatttg ccgtcgtgcg cgtggcgata acccggatga tcgttgcacc    180

ggccagagcg cggattgccc gcgtaacggc ctgtatggc                           219


<210> SEQ ID NO 130
<211> LENGTH: 71
<212> TYPE: PRT
<213> ORGANISM: Artificial Sequence
<220> FEATURE:
<223> OTHER INFORMATION: Description of Artificial Sequence: Synthetic
      disintegrin variant

<400> SEQUENCE: 130

Gly Glu Glu Cys Asp Cys Gly Ser Pro Gly Asn Pro Cys Cys Asp Ala
1               5                   10                  15

Ala Thr Cys Lys Leu Arg Pro Gly Ala Gln Cys Ala Glu Gly Leu Cys
            20                  25                  30

Cys Glu Gln Cys Arg Phe Ile Lys Ala Gly Thr Val Cys Arg Val Ala
        35                  40                  45

Arg Gly Asp Trp Asn Asp Asp Lys Cys Thr Gly Gln Ser Ala Asp Cys
    50                  55                  60

Pro Arg Asn Gly Phe Tyr Gly
65                  70


<210> SEQ ID NO 131
<211> LENGTH: 213
<212> TYPE: DNA
<213> ORGANISM: Artificial Sequence
<220> FEATURE:
<223> OTHER INFORMATION: Description of Artificial Sequence: Synthetic
      disintegrin variant

<400> SEQUENCE: 131

ggcgaagaat gcgattgcgg cagcccgggc aacccgtgct gcgatgcggc gacctgcaaa     60

ctgcgtccgg gcgcgcagtg cgcggaaggc ctgtgctgcg aacagtgccg ttttattaaa    120

gcgggcaccg tgtgccgtgt ggcgcgtggc gattggaacg atgataaatg caccggccag    180

agcgcggatt gcccgcgtaa cggcttttat ggc                                 213


<210> SEQ ID NO 132
<211> LENGTH: 71
<212> TYPE: PRT
<213> ORGANISM: Artificial Sequence
```

<220> FEATURE:
<223> OTHER INFORMATION: Description of Artificial Sequence: Synthetic
disintegrin variant

<400> SEQUENCE: 132

Glu Ala Gly Glu Glu Cys Asp Cys Gly Ala Pro Ala Asn Pro Cys Cys
1 5 10 15

Asp Ala Ala Thr Cys Lys Leu Arg Pro Gly Ala Gln Cys Ala Glu Gly
20 25 30

Asp Cys Cys Glu Gln Cys Arg Phe Val Lys Glu Gly Thr Val Cys Arg
35 40 45

Glu Ala Lys Gly Asp Trp Asn Asp Asp Ser Cys Thr Gly Gln Ser Ala
50 55 60

Asp Cys Pro Arg Asn Gly Phe
65 70

<210> SEQ ID NO 133
<211> LENGTH: 213
<212> TYPE: DNA
<213> ORGANISM: Artificial Sequence
<220> FEATURE:
<223> OTHER INFORMATION: Description of Artificial Sequence: Synthetic
disintegrin variant

<400> SEQUENCE: 133
gaagcgggcg aagaatgcga ttgcggcgcg ccggcgaacc cgtgctgcga tgcggcgacc 60
tgcaaactgc gtccgggcgc gcagtgcgcg gaaggcgatt gctgcgaaca gtgccgtttt 120
gtgaaagaag gcaccgtgtg ccgtgaagcg aaaggcgatt ggaacgatga tagctgcacc 180
ggccagagcg cggattgccc gcgtaacggc ttt 213

<210> SEQ ID NO 134
<211> LENGTH: 71
<212> TYPE: PRT
<213> ORGANISM: Artificial Sequence
<220> FEATURE:
<223> OTHER INFORMATION: Description of Artificial Sequence: Synthetic
disintegrin variant

<400> SEQUENCE: 134

Ala Gly Glu Glu Cys Asp Cys Gly Ser Pro Ala Asn Pro Cys Cys Asp
1 5 10 15

Ala Ala Thr Cys Lys Leu Arg Pro Gly Ala Gln Cys Ala Asp Gly Leu
20 25 30

Cys Cys Asp Gln Cys Arg Phe Ile Lys Lys Gly Lys Ile Cys Arg Arg
35 40 45

Ala Arg Gly Asp Asn Pro Asp Asp Arg Cys Thr Gly Gln Ser Ala Asp
50 55 60

Cys Pro Arg Asn Arg Phe His
65 70

<210> SEQ ID NO 135
<211> LENGTH: 213
<212> TYPE: DNA
<213> ORGANISM: Artificial Sequence
<220> FEATURE:
<223> OTHER INFORMATION: Description of Artificial Sequence: Synthetic
disintegrin variant

<400> SEQUENCE: 135
gcgggcgaag aatgcgattg cggcagcccg gcgaacccgt gctgcgatgc ggcgacctgc 60
aaactgcgtc cgggcgcgca gtgcgcggat ggcctgtgct gcgatcagtg ccgttttatt 120
aaaaaaggca aaatttgccg tcgtgcgcgt ggcgataacc cggatgatcg ttgcaccggc 180
cagagcgcgg attgcccgcg taaccgtttt cat 213

<210> SEQ ID NO 136
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 136
ccgcggccgc ggtcagtggt atcttggaca gtcagc 36

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: Synthetic linker peptide

<400> SEQUENCE: 137

Gly Ser Gly Ser Gly Ser
1 5

<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence: Synthetic rhodostomin variant

<400> SEQUENCE: 138

Ala Lys Gly Asp Trp Asn
1 5

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic rhodostomin variant

<400> SEQUENCE: 139

Pro Arg Gly Glu Met Pro
1 5

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic rhodostomin variant

<400> SEQUENCE: 140

Pro Arg Pro Asp Asp Leu
1 5

METHODS OF TREATING αVβ3 INTEGRIN-ASSOCIATED DISEASES BY ADMINISTERING POLYPEPTIDES SELECTIVE FOR αVβ3 INTEGRIN

CROSS-REFERENCE TO RELATED APPLICATIONS

This patent application claims priority of U.S. patent application Ser. No. 12/004,045 filed Dec. 20, 2007, now U.S. Pat. No. 7,943,728, which claims priority of U.S. provisional patent application Ser. No. 60/871,854 filed Dec. 26, 2006, the contents of which are hereby incorporated by reference in their entirety.

FIELD OF THE INVENTION

The present invention relates to disintegrin variants, and more specifically to disintegrin variants as selective αvβ3 integrin antagonists for treatment and prevention of αvβ3 integrin-associated diseases. The present invention also relates to pegylated proteins comprising a disintegrin variant having an RGD motif variant $^{48}$ARLDDL$^{53}$. The invention also relates to the use of the polypeptides of the invention for the treatment and prevention of αvβ3 integrin-associated diseases.

BACKGROUND OF THE INVENTION

Bone is a complex tissue composed of several cell types which are continuously undergoing a process of renewal and repair termed "bone remodeling." The two major cell types responsible for bone remodeling are osteoclasts, which resorb bone, and osteoblasts, which form new bone. Bone remodeling has been known to be regulated by several systemic hormones (e.g., parathyroid hormone, 1,25-dihydroxy vitamin $D_3$, sex hormones, and calcitonin) and local factors (e.g., nitric oxide, prostaglandins, growth factors, and cytokines).

Integrins are heterodimeric matrix receptors that anchor cells to substrates and transmit externally derived signals across the plasma membrane. Integrin αvβ3 is involved in the osteoclast-mediated bone resorption, both in vivo and in vitro. This heterodimer molecule recognizes the amino acid motif Arg-Gly-Asp (RGD) contained in bone matrix proteins such as osteopontin and bone sialoprotein. Integrin αvβ3 is expressed in an osteoclast and its expression is modulated by resorptive steroids and cytokines. Based on blocking experiments, αvβ3 integrin has been identified as a major functional adhesion receptor on osteoclasts. Inhibitors of integrin αvβ3 reduce the capacity of osteoclasts to bind to and resorb bone. Integrin αvβ3 plays a major role in the function of osteoclasts and inhibitors of this integrin are being considered for treating or preventing osteoporosis, osteolytic metastases, and malignancy-induced hypercalcemia.

There are many bone diseases that are related to osteolysis that is mediated by osteoclasts. Osteoporosis is the most common one that is induced when resorption and formation of bone are not coordinated and bone breakdown overrides bone building. Osteoporosis is also caused by other conditions, such as hormonal imbalance, diseases, or medications (e.g., corticosteroids or anti-epileptic agents). Bone is one of the most common sites of metastasis by human breast, prostate, lung and thyroid cancers, as well as other cancers. Osteoporosis may also result from post-menopausal estrogen deficiency. Secondary osteoporosis may be associated with rheumatoid arthritis. Bone metastasis shows a very unique step of osteoclastic bone resorption that is not seen in metastasis of other organs. It is widely accepted that osteolysis that is associated with cancer is essentially mediated by osteoclasts, which seem to be activated and may be indirectly activated through osteoblasts or directly by tumor products. In addition, hypercalcemia (increased blood-calcium concentration) is an important complication of osteolytic bone diseases. It occurs relatively frequently in patients with extensive bone destruction, and is particularly common in breast, lung, renal, ovarian and pancreatic carcinomas and in myeloma.

Disintegrins are a family of low-molecular-weight RGD-containing peptides that bind specifically to integrins αIIbβ3, α5β1 and αvβ3 expressed on platelets and other cells including vascular endothelial cells and some tumor cells. In addition to their potent antiplatelet activity, studies of disintegrins have revealed new uses in the diagnosis of cardiovascular diseases and the design of therapeutic agents in arterial thrombosis, osteoporosis and angiogenesis-related tumor growth and metastasis. Rhodostomin (Rho), a disintegrin derived from the venom of *Colloselasma rhodostoma*, has been found to inhibit platelet aggregation in vivo and in vitro through the blockade of platelet glycoprotein αIIbβ3. Furthermore, rhodostomin is reported to inhibit the adhesion of breast and prostate carcinoma cells to both unmineralized and mineralized bone extracellular matrices in a dose-dependent manner, without affecting the viability of tumor cells. In addition, rhodostomin inhibits the migration and invasion of breast and prostate carcinoma cells. Rhodostomin has also been shown to inhibit adipogenesis and obesity. However, because rhodostomin non-specifically binds to integrins αIIbβ3, α5β1 and αvβ3, the pharmaceutical uses of rhodostomin may cause serious side effects. For example, when applying rhodostomin in treating carcinomas, the inhibition of platelet aggregation is an undesirable side effect.

The role of αvβ3 integrin in bone diseases has been well documented. See, for example, F. Patrick Ross et al, *Nothing but skin and bone*, the Journal of Clinical Investigation, Vol. 116, #5, May 2006; S. B. Rodan et al, *Integrin function in osteoclasts*, Journal of Endocrinology (1997) 154, S47-S56; Steven L. Teitelbaum, *Editorial: Osteoporosis and Integrins*, the Journal of Clinical Endocrinology and Metabolism, April 2005, 90(4): 2466-2468; Steven L. Teitelbaum, *Osteoclasts, integrins, and osteoporosis*, Journal of Bone and Mineral Metabolism, (2000) 18: 344-349; Ichiro Nakamura et al, *Involvement of* αvβ3 *integrins in osteoclast function*, Journal of Bone and Mineral Metabolism, (2007) 25: 337-344; Le T. Duong et at, The role of integrins in osteoclast function, Journal of Bone and Mineral Metabolism, (1999) 17: 1-6; and A Teti et al, *The Role of the AlphaVbeta3 Integrin in the Development of Osteolytic Bone Metastases: A Pharmacological Target for Alternative Therapy*?, Calcified Tissue International (2002) 71: 293-299.

In addition to bone diseases, αvβ3 integrin plays an important role in angiogenesis and tumor growth in conditions not related to bone diseases.

Thus, it may be desirable to create polypeptides selective for αvβ3 integrin with improved stability and lasting effects. These polypeptides will be potentially suitable to treat diseases and conditions involving αvβ3 integrin, including but not limited to various bone diseases, cancer, and diseases involving angiogenesis.

It would also be advantageous to create pegylated polypeptides selective for αvβ3 integrin to prolong the duration and decrease the antigenicity of a protein drug.

SUMMARY OF THE INVENTION

In accordance with the invention, one aspect of the invention is a polypeptide that is selective for αvβ3 integrin. The polypeptide exhibits reduced binding to αIIbβ3 and/or α5β1 integrin compared to a wild-type disintegrin. The polypeptide is encoded by a modified disintegrin nucleotide sequence that encodes a modified amino acid sequence, with reduced αIIbβ3 and/or α5β1 integrin binding activity.

The polypeptide may be pegylated or conjugated with albumin or conjugated with a tissue target molecule. More specifically, the invention provides pegylated polypeptides, including but not limited to PEG-ARLDDL which is a pegylated ARLDDL protein.

The disintegrin nucleotide sequence may be derived from snake venom. The disintegrin may be chosen from rhodostomin, albolabrin, applagin, basilicin, batroxostatin, bitistatin, cereberin, cerastin, crotatroxin, durissin, elegantin, flavoridin, flavostatin, halysin, halystatin, jararacin, jarastatin, kistrin, lachesin, lutosin, molossin, salmosin, saxatilin, tergeminin, trimestatin, trimucrin, trimutase, ussuristatin, and viridin.

Another aspect of the invention is a polypeptide that is a variant of rhodostomin, in which the rhodostomin comprises the amino acid sequence of SEQ ID NO: 1.

Another aspect of the invention is a polypeptide that comprises an amino acid chosen from SEQ ID NOs: 30-42.

Another aspect of the invention is a polypeptide comprising the amino acid sequence of SEQ ID NO: 29, which further comprises, one, two, three of four amino acid substitutions in positions corresponding to amino acids 48, 50, 52, or 53 of SEQ ID NO: 1.

Another aspect of the invention is a polypeptide comprising amino acid substitutions chosen from Ala at position 48, Leu, Ile, and His at position 50, Asp, Met, and Asn at position 52, and Val, Leu, and Met at position 53 of SEQ ID NO: 1.

Another aspect of the invention is a polypeptide that is an encoded nucleotide sequence chosen from SEQ ID NOs: 43-56.

Another aspect of the invention is a polypeptide that exhibits at least about a 5, 50, or 100-fold decrease in affinity to αIIbβ3 and/or α5β1 as compared to rhodostomin. In one embodiment of the invention, the polypeptide exhibits at least about a 200-fold decrease in affinity to αIIbβ3 and/or α5β1 integrin as compared to rhodostomin. In another embodiment of the invention, the polypeptide exhibits at least about a 1000 or 2000-fold decrease in affinity to αIIbβ3 and/or α5β1 integrin as compared to rhodostomin. In another embodiment of the invention, the polypeptide exhibits at least about 5, 50, 100, 1000, or 2000-fold decrease in affinity to platelet as compared to rhodostomin. In still another embodiment of the invention, the polypeptide exhibits a substantially reduced activity in prolongation of blood clotting time as compared to rhodostomin and or a wild-type disintegrin.

Yet another aspect of the invention is a physiologically acceptable composition comprising a polypeptide of the invention, and a pharmaceutically acceptable carrier.

Another aspect of the invention is a polypeptide comprising an amino acid sequence chosen from SEQ ID NOs: 57-69.

Yet another aspect of the invention is a method of using a disintegrin variant for treatment and/or prevention of an αvβ3 integrin-associated disease in a mammal including a human. The method includes the step of administering to the mammal in need thereof a therapeutically effective amount of a disintegrin variant. The polypeptide employed in the method may be pegylated or conjugated with albumin or conjugated with a tissue target molecule.

In one aspect of the invention, the disintegrin may be derived from a snake venom, and may be chosen from one of rhodostomin, albolabrin, applagin, basilicin, batroxostatin, bitistatin, cereberin, cerastin, crotatroxin, durissin, elegantin, flavoridin, flavostatin, halysin, halystatin, jararacin, jarastatin, kistrin, lachesin, lutosin, molossin, salmosin, saxatilin, tergeminin, trimestatin, trimucrin, trimutase, ussuristatin, and viridin.

In one aspect of the invention, the disintegrin is rhodostomin.

In another aspect of the invention, the rhodostomin comprises a variant of rhodostomin comprising the amino acid sequence of SEQ ID NO: 1.

In another aspect, the rhodostomin comprises an RGD motif variant comprising an amino acid chosen from SEQ ID NOs: 30-42.

In another aspect, the rhodostomin comprises an amino acid chosen from SEQ ID NOs: 57-69.

In one aspect of the invention, the αvβ3 integrin-associated disease includes, but is not limited to, osteoporosis, bone tumor or cancer growth and symptoms related thereto, angiogenesis-related tumor growth and metastasis, tumor metastasis in bone, malignancy-induced hypercalcemia, angiogenesis-related eye diseases, Paget's disease, rheumatic arthritis and osteoarthritis.

In another aspect of the invention, a polypeptide of the invention is used for treatment and/or prevention of an angiogenesis-related eye disease, which includes, but is not limited to, age-related macular degeneration, diabetic retinopathy, corneal neovascularizing diseases, ischaemia-induced neovascularizing retinopathy, high myopia, and retinopathy of prematurity.

In still another aspect of the invention, a polypeptide of the invention is used for treatment and/or prevention of osteoporosis. The osteoporosis is may be associated with a pathological condition chosen from post-menopausal estrogen deficiency, secondary osteoporosis, rheumatoid arthritis, ovariectomy, Paget's disease, bone cancer, bone tumor, osteoarthritis, increased osteoclast formation, and increased osteoclast activity. Furthermore, the osteoporosis includes, but is not limited to, an ovariectomy-induced or post-menopausal osteoporosis or bone loss.

Yet another aspect of the invention is a method of using a polypeptide of the invention for treatment and/or prevention of an ovariectomy-induced physiological change in a mammal including a human.

Yet another aspect of the invention is a method of using a disintegrin variant for inhibition and/or prevention of tumor cell growth in bone and symptoms related thereto in a mammal including a human.

Yet another aspect of the invention is a method for making a polypeptide of the invention, the method comprising the steps of: (a) transfecting a host cell with a polynucleotide encoding said polypeptide (b) growing said host cell in a culture medium; and (c) isolating said polypeptide. The method of the invention may further comprise growing host cells in a culture medium free of amino acids; and collecting supernatant to obtain said polypeptide. The method may further comprise adding methanol to the culture medium to induce polypeptide expression in the host cells. The method may further comprise the step of performing column chromatography to obtain said polypeptide. In one embodiment, the method may further comprise the step of performing HPLC to obtain the isolated polypeptide. The method may further comprise pegylating said polypeptide or a fusion of a tissue targeting molecule to the said polypeptide.

Another aspect of the invention is a polynucleotide encoding a polypeptide selective for αvβ3 integrin, wherein the polypeptide may be a variant of a disintegrin isolated from snake venom.

In another aspect of the invention, the disintegrin is chosen from rhodostomin, albolabrin, applagin, basilicin, batroxostatin, bitistatin, cereberin, cerastin, crotatroxin, durissin, elegantin, flavoridin, flavostatin, halysin, halystatin, jararacin, jarastatin, kistrin, lachesin, lutosin, molossin, salmosin, saxatilin, tergeminin, trimestatin, trimucrin, trimutase, ussuristatin, and viridin.

In another aspect of the invention, the disintegrin comprises rhodostomin.

In another aspect of the invention, the disintegrin comprises a variant of rhodostomin comprising the amino acid sequence of SEQ ID NO: 1.

In another aspect of the invention, the polypeptide comprises an RGD motif variant having an amino acid sequence chosen from SEQ ID NOs: 30-42.

In another aspect of the invention, the polynucleotide comprises a sequence chosen from SEQ ID NOs: 43-56 and 78-135.

In another aspect of the invention, the polynucleotide may encode the polypeptides with one, two, three of four amino acid substitutions in positions corresponding to amino acids 48, 50, 52, or 53 of SEQ ID NO: 1.

Another aspect of the invention is a polynucleotide that hybridizes under stringent conditions to a polynucleotide of the invention.

Another aspect of the invention is a polypeptide encoded by a polynucleotide that hybridizes to a polynucleotide sequence of the invention.

These and other aspects will become apparent from the following description of the various embodiments taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

BRIEF DESCRIPTION OF THE DRAWINGS

FIGS. 14A-D show amino acid sequences SEQ ID NOs: 1, and 57-69 of rhodostomin variants.

FIGS. 15A-C show nucleotide sequences SEQ ID NOs: 43-56 of rhodostomin variants.

FIGS. 16A-H show amino acid and nucleotide sequences SEQ ID NOs: 78-135 of disintegrin variants.

FIG. 17A shows photographs showing reduced blood vessel density in MATRIGEL™ plugs from mice treated with PEG-ARLDDL in comparison with untreated control mice.

FIG. 17B is a bar chart that shows that mice treated with PEG-ARLDDL had significantly lower hemoglobin content in comparison with untreated control mice.

FIG. 18 shows photographs of tumors excised from the control mice; mice treated with 2 mg/kg/week PEG-ARLDDL; and mice treated with 10 mg/kg/week PEG-ARLDDL.

FIG. 19 is a bar chart that shows that PEG-ARLDDL significantly inhibited tumor growth in a dose-dependent manner.

FIG. 20 is a graph that shows that PEG-ARLDDL administered once a week had a stronger inhibitory effect on tumor growth as compared to PEG-ARLDDL administered once every two weeks.

FIG. 21 shows photographs of tumors excised from the control mice; mice treated with 10 mg/kg/week PEG-ARLDDL administered once a week; and mice treated with 10 mg/kg/week PEG-ARLDDL administered twice a week.

FIG. 23 is a graph that shows that PEG-ARLDDL significantly enhanced the cytotoxic activity of daunomycin.

FIG. 24 shows photographs of tumors excised from the control mice; mice treated with daunomycin alone; mice treated with PEG-ARLDDL alone; and mice treated with a combination of daunomycin and PEG-ARLDDL.

FIG. 25 is a bar chart that shows that PEG-ARLDDL significantly enhanced the cytotoxic activity of daunomycin.

FIG. 26 shows photographs of U87 human glioma cells that demonstrate that PEG-ARLDDL significantly inhibited osteopontin-induced glioma invasion in hypoxia.

DETAILED DESCRIPTION OF THE INVENTION

Figure 1:
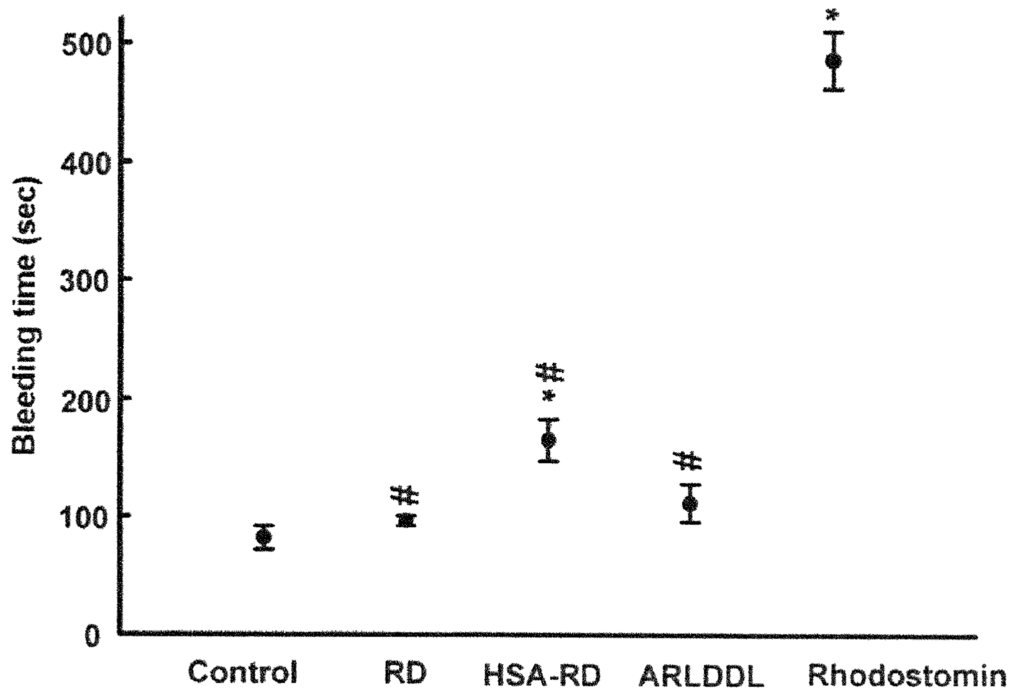
FIG. 1 is a graph showing less impact of RD and HSA-RD and ARLDDL than rhodostomin protein on bleeding time in mice.

The present invention is more particularly described in the following examples that are intended as illustrative only since numerous modifications and variations therein will be apparent to those skilled in the art. Various embodiments of the invention are now described in detail. As used in the description and throughout the claims that follow, the meaning of "a", "an", and "the" includes plural reference unless the context clearly dictates otherwise. Also, as used in the description and throughout the claims that follow, the meaning of "in" includes "in" and "on" unless the context clearly dictates otherwise. Additionally, some terms used in this specification are more specifically defined below. All references cited and discussed in this specification are incorporated herein by reference in their entireties and to the same extent as if each reference was individually incorporated by reference.

Reference will now be made in detail to the present embodiments (exemplary embodiments) included in the invention, examples of which are illustrated in the accompanying drawings.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. The invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

"Around," "about" or "approximately" shall generally mean within 20 percent, within 10 percent, within 5, 4, 3, 2, or 1 percent of a given value or range. Numerical quantities given are approximate, meaning that the term "around," "about" or "approximately" can be inferred if not expressly stated.

The terms "polynucleotide," "nucleotide," "nucleic acid," "nucleic acid molecule," "nucleic acid sequence," "polynucleotide sequence," and "nucleotide sequence" are used interchangeably to refer to polymeric forms of nucleotides of any length. The polynucleotides can comprise deoxyribonucleotides, ribonucleotides, and/or their analogs or derivatives. The term includes variants. Variants may include insertions, additions, deletions, or substitutions. Nucleotide sequences are listed in the 5' to 3' direction.

The terms "polypeptide," "peptide," and "protein," are used interchangeably to refer to a polymeric form of amino acids of any length, which can include naturally-occurring amino acids, coded and non-coded amino acids, chemically or biochemically modified, derivatized, or designer amino acids, amino acid analogs, peptidomimetics, and depsipeptides, and polypeptides having modified, cyclic, bicyclic, depsicyclic, or depsibicyclic peptide backbones. The term includes single chain protein as well as multimers. The term also includes proteins conjugated to a label such as FITC, biotin, and radioisotopes, including, but not limited to $^{64}$Cu, $^{67}$Cu, $^{90}$Y, 99mTc, $^{111}$In, $^{124}$I, $^{125}$I, $^{131}$I, $^{137}$Cs, $^{186}$Re, $^{211}$At, $^{212}$Bi, $^{213}$Bi, $^{223}$Ra, $^{241}$Am, and $^{244}$Cm; enzymes having detectable products (for example, luciferase, peroxidase, alkaline phosphatase, β-galactosidase, and the like); fluorescers and fluorescent labels, fluorescence emitting metals, for example, $^{152}$Eu, or others of the lanthanide series, electrochemiluniescent compounds, chemiluminescent compounds, for example, luminol, isoluminol, or acridinium salts; specific binding molecules, for example, magnetic particles, microspheres, nanospheres, and the like. The term also includes peptides conjugated to therapeutic agents.

The terms also include fusion proteins, including, but not limited to, glutathione S-transferase (GST) fusion proteins, fusion proteins with a heterologous amino acid sequence such as bioluminescent proteins, for example, luciferin, or aequorin (green fluorescent protein), with heterologous and homologous leader sequences, fusion proteins with or without N-terminal methionine residues, pegylated proteins, and immunologically tagged, or his-tagged proteins. Such fusion proteins also include fusions to epitopes. Such fusion proteins can comprise multimers of the peptides of the invention, e.g. homodimers or homomultimers, and heterodimers and heteromultimers. The term also includes peptide aptamers.

The term "hybridizes specifically," in the context of a polynucleotide, refers to hybridization under stringent conditions. Conditions that increase stringency of both DNA/DNA and DNA/RNA hybridization reactions are widely known and published in the art. Examples of stringent hybridization conditions include hybridization in 4× sodium chloride/sodium citrate (SSC), at about 65-70° C., or hybridization in 4×SSC plus 50% formamide at about 42-50° C., followed by one or more washes in 1×SSC, at about 65-70° C.

The term "ligand" refers to a molecule that binds to another molecule, including a receptor.

A "host cell" is an individual cell or cell culture which can be or has been a recipient of any recombinant vector(s) or polynucleotide. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention may be called a "recombinant host cell."

"Treatment," covers any administration or application of remedies for disease in a mammal, including a human, and includes inhibiting the disease, arresting its development, or relieving the disease, for example, by causing regression, or restoring or repairing a lost, missing, or defective function; or stimulating an inefficient process. The term includes obtaining a desired pharmacologic and/or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse affect attributable to the disorder. Thus, the invention provides both treatment and prophylaxis. It includes (1) preventing the disorder from occurring or recurring in a subject who may be predisposed to the disorder but is not yet symptomatic, (2) inhibiting the disorder, such as arresting its development, (3) stopping or terminating the disorder or at least its associated symptoms, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, and/or tumor size.

The phrase "cancer associated with a highly expressed osteopontin (OPN)" refers to a cancer wherein the expression level of OPN is higher than the expression level of OPN in peripheral normal tissues.

A "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

A "composition" refers to a mixture that usually contains a carrier, such as a pharmaceutically acceptable carrier or excipient that is conventional in the art and which is suitable for administration into a subject for therapeutic, diagnostic, or prophylactic purposes. It may include a cell culture in which the polypeptide or polynucleotide is present in the cells or in the culture medium. For example, compositions for oral administration can form solutions, suspensions, tablets, pills, capsules, sustained release formulations, oral rinses, or powders.

"Disease" refers to any condition, infection, disorder, or syndrome that requires medical intervention or for which medical intervention is desirable. Such medical intervention can include treatment, diagnosis, and/or prevention.

Peptides

The peptides of the invention can be expressed using methods known in the art. Cell-based methods and cell-free methods are suitable for producing peptides of the invention. Cell-based methods generally involve introducing a nucleic acid construct into a host cell in vitro and culturing the host cell under conditions suitable for expression, then harvesting the peptide, either from the culture medium or from the host cell, (for example, by disrupting the host cell), or both. The invention also provides methods of producing a peptide using cell-free in vitro transcription/translation methods, which are well known in the art.

Suitable host cells include prokaryotic or eukaryotic cells, including, for example, bacterial, yeast, fungal, plant, insect, and mammalian cells.

Typically, a heterologous peptide, whether modified or unmodified, may be expressed on its own, as described above, or as a fusion protein, and may include not only secretion signals, but also a secretory leader sequence. A secretory leader sequence of the invention may direct certain proteins to the endoplasmic reticulum (ER). The ER separates the membrane-bound proteins from other proteins. Once localized to the ER, proteins can be further directed to the Golgi apparatus for distribution to vesicles, including secretory vesicles, the plasma membrane, lysosomes, and other organelles.

Additionally, peptide moieties and/or purification tags may be added to the peptides. Such regions may be removed prior to final preparation of the polypeptide. The addition of peptide moieties to polypeptides to engender secretion or excretion, to improve stability, and to facilitate purification, among other reasons, are familiar and routine techniques in the art. Suitable purification tags include, for example, V5, polyhistidines, avidin, and biotin. Conjugation of peptides to compounds such as biotin can be accomplished using techniques well known in the art. (Hermanson ed. (1996) Bioconjugate Techniques; Academic Press). Peptides can also be conjugated with radioisotopes, toxins, enzymes, fluorescent labels, colloidal gold, nucleic acids, vinorelbine, and doxorubicin using techniques known in the art. (Hermanson ed. (1996) Bioconjugate Techniques; Academic Press; Stefano et al. (2006).

Fusion partners suitable for use in the invention include, for example, fetuin, human serum albumin, Fc, and/or one or more of their fragments. Conjugated proteins, such as polyethylene glycol conjugates, are also provided.

The peptides of the invention can also be chemically synthesized using techniques known in the art (e.g., see Hunkapiller et al., Nature, 310:105 111 (1984); Grant ed. (1992) Synthetic Peptides, A Users Guide, W.H. Freeman and Co.; U.S. Pat. No. 6,974,884)). For example, a polypeptide corresponding to a fragment of a polypeptide can be synthesized by use of a peptide synthesizer or through the use of solid-phase methods known in the art.

Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levo rotary).

The polypeptides of the invention can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In one embodiment, high performance liquid chromatography ("HPLC") is employed for purification. Well known techniques for refolding protein may be employed to regenerate active conformation when the polypeptide is denatured during isolation and/or purification.

A peptide or peptidomimetic of the invention can be modified with or covalently coupled to one or more of a variety of hydrophilic polymers to increase solubility and circulation half-life of the peptide. Suitable nonproteinaceous hydrophilic polymers for coupling to a peptide include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran, and dextran derivatives. Generally, such hydrophilic polymers have an average molecular weight ranging from about 500 to about 100,000 daltons, from about 2,000 to about 40,000 daltons, or from about 5,000 to about 20,000 daltons. The peptide can be derivatized with or coupled to such polymers using any of the methods set forth in Zallipsky, S. (1995) Bioconjugate Chem., 6:150-165; Monfardini, C., et al. (1995) Bioconjugate Chem. 6:62-69; U.S. Pat. Nos. 4,640,835; 4,496,689; 4,301,144; 4,670,417; 4,791,192; 4,179,337, or WO 95/34326.

In some embodiments, a peptide of the invention is provided in formulation with pharmaceutically acceptable carriers, excipients, and diluents, of which a wide variety are known in the art. These pharmaceutical carriers, excipients, and diluents include those listed in the USP pharmaceutical excipients listing. USP and NF Excipients, Listed by Categories, p. 2404-2406, USP 24 NF 19, United States Pharmacopeial Convention Inc., Rockville, Md. (ISBN 1-889788-03-1). Pharmaceutically acceptable excipients, such as vehicles, adjuvants, carriers, or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable carriers include, but are not limited to, water, dextrose, glycerol, saline, ethanol, and combinations thereof. The carrier can contain additional agents such as wetting or emulsifying agents, pH buffering agents, or adjuvants which enhance the effectiveness of the formulation. Topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents can be added as necessary. Percutaneous penetration enhancers such as Azone can also be included.

In pharmaceutical dosage forms, the compositions of the invention can be administered in the form of their pharmaceutically acceptable salts, or they can also be used alone or in appropriate association, as well as in combination, with other pharmaceutically active compounds. The subject compositions are formulated in accordance to the mode of potential administration.

Methods of Treatment

An $\alpha v\beta 3$ integrin-associated disease, includes, but is not limited to, osteoporosis, cancer, bone tumor or cancer growth and symptoms related thereto, angiogenesis-related tumor growth and metastasis, tumor metastasis in bone, malignancy-induced hypercalcemia, angiogenesis-related eye diseases, Paget's disease, rheumatic arthritis and osteoarthritis.

Peptides of the invention may be administered to a subject in need of treatment by systemic injection, such as by intravenous injection; or by injection or application to the relevant site, such as by direct injection, or direct application to the site when the site is exposed in surgery; or by topical application, such as if the disorder is on the skin, for example.

Peptides of the invention can be used as monotherapy. Alternatively, the peptides of the invention can be used in combination with standard regimens to treat $\alpha v\beta 3$ integrin associated diseases.

For example, the peptides of the invention can be used in a combinational therapy with a therapeutically effective amount of one or more other pharmaceutical agents.

Preferably, another pharmaceutical agent is selected from the group consisting of an anti-cancer agent, an anti-inflammatory agent, an immune-modulating agent and an anti-osteoporosis agent.

Preferably, an anti-cancer agent is selected from the group consisting of an anti-angiogenic agent, a cytotoxic agent and an anti-neoplastic agent.

The other pharmaceutical agent(s) can be administered prior to, together with, or after administration of the peptides of the invention.

In some embodiments, the combinational therapy with other pharmaceutical agents provides synergistic effects, including but not limited to enhancing the therapeutic efficacy of the other agents; allowing using lower doses of the other agents, thereby decreasing their side effects and reducing resistance to the other agents; and lowering the likelihood and/or the rate of cancer recurrence.

In some embodiments, the polypeptides of the invention are particularly effective against cancers which are associated with a highly expressed osteopontin. In preferred embodiments, the polypeptides of the invention can inhibit osteopontin-induced tumor invasion.

Administration of the agents can be achieved in various ways, including oral, buccal, nasal, rectal, parenteral, intraperitoneal, intradermal, transdermal, subcutaneous, intravenous, intra-arterial, intracardiac, intraventricular, intracranial, intratracheal, and intrathecal administration, etc., or otherwise by implantation or inhalation. Thus, the subject compositions can be formulated into preparations in solid, semi-solid, liquid, or gaseous forms, such as tablets, capsules, powders, granules, ointments, solutions, suppositories, injections, inhalants and aerosols. The following methods and excipients are merely exemplary and are in no way limiting.

Suitable excipient vehicles are, for example, water, saline, dextrose, glycerol, ethanol, or the like, and combinations thereof. In addition, if desired, the vehicle can contain minor amounts of auxiliary substances such as wetting or emulsifying agents or pH buffering agents. Actual methods of preparing such dosage forms are known, or will be apparent, to those skilled in the art. The composition or formulation to be administered will, in any event, contain a quantity of the agent adequate to achieve the desired state in the subject being treated.

Peptides of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers, and preservatives. Other formulations for oral or parenteral delivery can also be used, as conventional in the art.

"Disintegrins" refer to a family of polypeptides that may be purified from snake venoms, which contain the arginine-glycine-aspartic acid (RGD) sequence. Without being bound by any theory or mechanism, it is believed that the RGD tripeptide binds with high affinity to integrins to block the interaction of integrins with RGD-containing proteins. Disintegrins thus block adhesive functions and act as platelet aggregation inhibitors.

The abbreviation "Rho" means "rhodostomin," which is a disintegrin derived from the venom of *Colloselasma rhodostoma*. Rhodostomin non-specifically binds to integrins $\alpha IIb\beta 3$, $\alpha 5\beta 1$ and $\alpha v\beta 3$, and prolongs blood clotting time by inhibiting platelet aggregation through the blockade of platelet glycoprotein $\alpha IIb\beta 3$.

The "disintegrin variant" or "rhodostomin variant" refers to a functionally active protein, or a polypeptide or any derivatives thereof, that comprises an amino acid sequence derived or modified or mutated from a wild-type disintegrin such as rhodostomin. A functionally active disintegrin/rhodostomin variant can specifically bind to and inhibit integrin $\alpha v\beta 3$ activity. The disintegrin or rhodostomin variant of the present invention can be constructed by any method suitable to the aims of the present invention, and in one embodiment by a site-directed mutagenesis method, and in another embodiment by a polymerase chain reaction method. Variants may include insertions, additions, deletions, or substitutions compared with the subject peptides. Variants of polypeptide sequences include biologically active polymorphic variants.

Peptides of the invention can include naturally-occurring and non-naturally occurring amino acids. Peptides can comprise D-amino acids, a combination of D- and L-amino acids, and various "designer" or "synthetic" amino acids (for example, β-methyl amino acids, Cα-methyl amino acids, and Nα-methyl amino acids, etc.) to convey special properties. Additionally, peptides can be cyclic. Peptides can include non-classical amino acids in order to introduce particular conformational motifs. Any known non-classical amino acid can be used. Amino acid analogs and peptidomimetics can be incorporated into a peptide to induce or favor specific secondary structures, including, but not limited to, LL-Acp (LL-3-amino-2-propenidone-6-carboxylic acid), a β-turn inducing dipeptide analog; β-sheet inducing analogs; β-turn inducing analogs; α-helix inducing analogs; γ-turn inducing analogs; Gly-Ala turn analogs; amide bond isostere; or tretrazol, and the like.

A desamino or descarboxy residue can be incorporated at the terminal ends of the peptide, so that there is no terminal amino or carboxyl group, to decrease susceptibility to proteases or to restrict conformation. C-terminal functional groups include amide, amide lower alkyl, amide di (lower alkyl), lower alkoxy, hydroxy, and carboxy, and the lower ester derivatives thereof, and the pharmaceutically acceptable salts thereof.

The term "$IC_{50}$," or "the half maximal inhibitory concentration" refers to the concentration of Rho or its variant that is required for 50% inhibition of its receptor. $IC_{50}$ is a measure of how much of Rho or its variant is needed to inhibit a biological process by 50%, such as the variant's affinity to its receptor.

The term "therapeutically effective amount" as used refers to an amount which, when administered to a living subject, achieves a desired effect on the living subject. For example, an effective amount of the disintegrin or Rho variant of the invention for administration to the living subject is an amount that prevents and/or treats an integrin $\alpha v\beta 3$-mediated disease. The exact amount will depend on the purpose of the treatment, and will be ascertainable by one skilled in the art using known techniques. As is known in the art, adjustments for systemic versus localized delivery, age, body weight, general health, sex, diet, time of administration, drug interaction, and the severity of the condition may be necessary, and will be ascertainable with routine experimentation by those skilled in the art.

The term "receptor antagonist" refers to a binding ligand of a receptor that inhibits the function of a receptor by blocking the binding of an agonist to the receptor, or which allows agonist binding, but inhibits the ability of the agonist to activate the receptor.

The term "substantially reduced integrin $\alpha IIb\beta 3$ and/or $\alpha 5\beta 1$ receptor-blocking activity" refers to a reduced activity of at least five fold in blocking integrin $\alpha IIb\beta 3$ and/or $\alpha 5\beta 1$ receptor compared to wild type rhodostomin or other disintegrins. For example, to calculate the reduction in $\alpha IIb\beta 3$ and/or $\alpha 5\beta 1$ receptor-blocking activity, the $IC_{50}$ of a rhodostomin variant for inhibition of integrin $\alpha IIb\beta 3$ and/or $\alpha 5\beta 1$ binding to a matrix protein, such as fibrinogen, is compared to of the $IC_{50}$ of Rho.

The term "RGD motif variant" refers to a peptide comprising a modification in the amino acid sequence that spans the RGD sequence of a corresponding wild-type sequence, such as the sequence comprising RGD in Rhodostomin. Examples of "RGD motif variants" include $^{48}$ARGDDP$^{53}$, $^{48}$PRLDMP$^{53}$, $^{48}$PRIDMP$^{53}$, and $^{48}$ARLDDL$^{53}$.

The term "RD" refers to a rhodostomin variant having a RGD motif variant $^{48}$PRLDMP$^{53}$.

The term "PGP" refers to a rhodostomin variant having a RGD motif variant $^{48}$PRGDGP$^{53}$.

The term "ARLDDL" refers to a rhodostomin variant having a RGD motif variant $^{48}$ARLDDL$^{53}$.

The term "inhibitory selectivity for integrin αvβ3 relative to αIIbβ3 and/or α5β1 receptors" refers to a variant's binding selectivity toward integrin αvβ3 over αIIbβ3 and/or α5β1 receptors, which is expressed as a ratio of the $IC_{50}$ of the variant for inhibition of αIIbβ3 and/or α5β1 receptors over that for inhibition of αvβ3 receptor.

The term "substantially reduced activity in prolongation of blood bleeding time" refers to a reduced ability to inhibit blood clotting in a statistically significant manner as measured by the bleeding time experiment described in the specification.

The term "PEG-ARLDDL" refers to a pegylated ARLDDL protein.

The terms "albumin-ARLDDL" or "HSA-ARLDDL" refers to a human albumin-conjugated product of RD protein.

Overview of the Invention

The present invention is related to disintegrin variants that are selective αvβ3 integrin antagonists. Disintegrin variants such as RD-related compounds potently inhibit osteoclast differentiation in vitro. They also inhibit osteoclast resorbing activity and ovariectomy-induced increase in osteoclast formation in animal studies. In addition, RD inhibits the tumor growth of human prostate and breast cancer cells in bone. Malignancy-induced hypercalcemia was also effectively blocked by RD-related proteins. Paget's disease (also known as osteitis deformans) is a chronic bone disorder that typically results in enlarged and deformed bones due to irregular breakdown and formation of bone tissues. Bisphosphonates have been approved for the treatment of Paget's disease. Osteoarthritis is also related to the increase in osteoclast activity. Based on the similar mechanism of action, RD derivatives should also be effective for treatment of these bone disorders. An intravenous injection of RD or PGP at a very large dose at 30 mg/kg did not affect the survival of mice (n=3). In addition, long term administration of PGP (I.V., 0.5 mg/kg/day) for 6 weeks did not affect serum level of creatinine, GOT, and GPT, suggesting lack of side effects on kidney and liver. Therefore, RD and its derivatives are potential drug candidates for treatment of osteoporosis, bone tumor, malignancy-induced hypercalcemia, Paget's disease, rheumatic arthritis, osteoarthritis and angiogenesis-related eye diseases.

Many kinds of snake venom contain proteins that comprise an RGD domain. These RGD domain-containing proteins are called disintegrins. A modification in the sequence spanning the RGD domain results in a very unique polypeptide variant with a reduced binding affinity to other kinds of integrins but an increased selectivity to αvβ3 integrin. The disintegrin variants including rhodostomin variants prove to be potential therapeutic candidates for, among others, osteoporosis, suppression of tumor growth in bone, and angiogenesis-related eye diseases. Moreover, disintegrin variants including rhodostomin variants having a RGD-motif region with at least one amino acid substitution may be valuable tools for developing selective antagonists of αvβ3 integrin.

One aspect of the invention is a polypeptide that has integrin αvβ3 receptor-antagonist activity and reduced integrin αIIbβ3 and/or α5β1 receptor-blocking activity as compared to a wild-type disintegrin. The polypeptide is encoded by a modified disintegrin nucleotide sequence that encodes a modified amino acid sequence, which results in a polypeptide having substantially reduced integrin αIIbβ3 and/or α5β1 receptor-blocking activity. The polypeptide may be pegylated or conjugated with albumin or conjugated with a tissue target molecule.

The disintegrin nucleotide sequence may be derived from snake venom. According to the invention, disintegrins include, but are not limited to, albolabrin (*Cryptelytrops albolabris*), applagin (*Agkistrodon piscivorus piscivorus*), basilicin (*Crotalus basiliscus*), batroxostatin (*Bothrops atrox*), bitistatin (*Bitis arietans*), cereberin (*Crotalus oreganus cerberus*), cerastin (*Crotalus cerastes cerastes*), crotatroxin (*Crotalus atrox*), durissin (*Crotalus durissus durissus*), elegantin (*Protobothrops elegans*), flavoridin (*Trimeresurus flavoviridis*), flavostatin (*Trimeresurus flavoviridis*), halysin (*Gloydius blomhoffi*), halystatin (*Gloydius halys*), jararacin (*Bothrops jararaca*), jarastatin (*Bothrops jararaca*), kistrin (*Calloselasma rhodostoma*), lachesin (*Lachesis muta muta*), lutosin (*Crotalus oreganus lutosus*), molossin (*Crotalus molossus molossus*), salmosin (*Gloydius blomhoffi brevicaudus*), saxatilin (*Gloydius halys*), tergeminin (*Sistrurus catenatus tergeminus*), trimestatin (*Trimeresurus flavoviridis*), trimucrin (*Protobothrops mucrosquamatus*), trimutase (*Protobothrops mucrosquamatus*), ussuristatin (*Gloydius ussuriensis*), virid in (*Crotalus viridis*).

Another aspect of the invention is an isolated polypeptide that is a variant of rhodostomin, in which the rhodostomin comprises an amino acid sequence defined by SEQ ID NO: 1, and the variant comprises an RGD motif variant.

In one embodiment of the invention, the RGD motif variant may contain an amino acid sequence chosen from SEQ ID NOs: 30-42.

Another aspect of the invention is a polypeptide comprising the amino acid sequence of SEQ ID NO: 29, which further comprises, one, two, three of four amino acid substitutions in positions corresponding to amino acids 48, 50, 52, or 53 of SEQ ID NO: 1.

Another aspect of the invention is a polypeptide comprising amino acid substitutions chosen from Ala at position 48, Leu, Ile, and His at position 50, Asp, Met, and Asn at position 52, and Val, Leu, and Met at position 53 of SEQ ID NO: 1.

Another aspect of the invention is a polypeptide that is encoded with a nucleotide sequence chosen from SEQ ID NOs: 43-56.

For example, and specifically, in another embodiment of the invention, the RGD motif variant may comprise at least one amino acid substitution at a residue corresponding to Gly$^{50}$ or Met$^{52}$ of the wild-type RGD motif set forth by SEQ ID NO: 29. The at least one amino acid substitution occurs at a residue corresponding to Leu$^{50}$ of SEQ ID NO: 36-37, Ile$^{50}$ of SEQ ID NO: 39, His$^{50}$ of SEQ ID NO: 40, Asn$^{52}$ of SEQ ID NO: 41, or Gly$^{52}$ of SEQ ID NO: 42.

In another embodiment of the invention, the RGD motif variant may comprise at least two amino acid substitutions at residues corresponding to Pro$^{48}$ and Met$^{52}$, or Met$^{52}$ and Pro$^{53}$ of the wild-type RGD motif set forth by SEQ ID NO: 29. The at least two amino acid substitutions may be residues corresponding to Ala$^{48}$ and Asp$^{52}$ of SEQ ID NO: 30, or Asp$^{52}$ and Met$^{53}$ of SEQ ID NO: 35.

In still another embodiment of the invention, the RGD motif variant may comprise at least three amino acid substitutions at residues corresponding to Pro$^{48}$, Met$^{52}$ and Pro$^{53}$, or Gly$^{50}$, Met$^{52}$ and Pro$^{53}$ of the wild-type RGD motif set forth by SEQ ID NO: 29. The at least three amino acid substitutions may be residues corresponding to Ala$^{48}$, Asp$^{52}$ and Val$^{53}$ of SEQ ID NO: 31, Ala$^{48}$, Asp$^{52}$ and Leu$^{53}$ of SEQ ID NO: 32, $Ala^{48}$, $Asp^{52}$ and $Met^{53}$ of SEQ ID NO: 34, $Leu^{50}$, $Asp^{52}$ and $Leu^{53}$ of SEQ ID NO: 37.

In still another embodiment of the invention, the RGD motif variant may comprise at least four amino acid substitutions at residues corresponding to $Pro^{48}$, $Gly^{50}$, $Met^{52}$ and $Pro^{53}$ of the wild-type RGD motif set forth by SEQ ID NO: 29. The at least four amino acid substitutions may be residues corresponding to $Ala^{48}$, $Leu^{50}$, $Asp^{52}$ and $Leu^{53}$ of SEQ ID NO: 38.

Another aspect of the invention is an isolated polypeptide that is encoded by a DNA having a modified rhodostomin nucleotide sequence chosen from SEQ ID NOs: 44-56. The polypeptide exhibits at least about a 5, 50, or 100-fold decrease in affinity to αIIbβ3 and/or α5β1 as compared to rhodostomin. In one embodiment of the invention, the polypeptide exhibits at least about a 200-fold decrease in affinity to αIIbβ3 and/or α5β1 integrin as compared to rhodostomin. In another embodiment of the invention, the polypeptide exhibits at least about a 1000 or 2000-fold decrease in affinity to αIIbβ3 and/or α5β1 integrin as compared to rhodostomin. In another embodiment of the invention, the polypeptide exhibits at least about 5, 50, 100, 1000, or 2000-fold decrease in affinity to platelet as compared to rhodostomin. In still another embodiment of the invention, the polypeptide exhibits a substantially reduced activity in prolongation of blood clotting time as compared to rhodostomin or wild-type disintegrin.

Yet another aspect of the invention is a physiologically acceptable composition comprising a polypeptide of the invention and a pharmaceutically acceptable carrier.

Yet another aspect of the invention is a method of using a disintegrin variant for treatment and/or prevention of an αvβ3 integrin-associated disease in a mammal including a human. The method includes the step of administering to the mammal in need thereof a therapeutically effective amount of an isolated polypeptide, or a pharmaceutically acceptable salt thereof. The polypeptide therein has integrin αvβ3 receptor-antagonist activity and substantially reduced integrin αIIbβ3 and/or integrin α5β1 receptor-blocking activity as compared to a wild-type disintegrin, and thereby results in treatment and/or prevention of the αvβ3 integrin-associated disease in the mammal. The polypeptide is encoded by a modified disintegrin nucleotide sequence that encodes a modified disintegrin amino acid sequence, which results in a polypeptide having substantially reduced integrin αIIbβ3 and/or integrin α5β1 receptor-blocking activity. The polypeptide employed in the method may be pegylated or conjugated with albumin or conjugated with a tissue target molecule.

As described above, the disintegrin nucleotide sequence may be derived from a snake venom, and may be chosen from rhodostomin, albolabrin, applagin, basilicin, batroxostatin, bitistatin, cereberin, cerastin, crotatroxin, durissin, elegantin, flavoridin, flavostatin, halysin, halystatin, jararacin, jarastatin, kistrin, lachesin, lutosin, molossin, salmosin, saxatilin, tergeminin, trimestatin, trimucrin, trimutase, ussuristatin, and viridin.

In one embodiment of the invention, the method includes the step of administering to the mammal in need thereof a therapeutically effective amount of an isolated polypeptide, or a pharmaceutically acceptable salt thereof, in which the polypeptide comprises the amino acid sequence of SEQ ID NO: 1, and the variant comprises an RGD motif variant.

In another embodiment of the invention, the method includes the step of administering to the mammal in need thereof a therapeutically effective amount of an isolated polypeptide, or a pharmaceutically acceptable salt thereof, in which the polypeptide is a variant of rhodostomin comprising the amino acid sequence defined by SEQ ID NO: 1, and the variant comprises a RGD motif variant having an amino acid sequence chosen from SEQ ID NOs: 30-42.

In still another embodiment of the invention, the method includes the step of administering to a mammal in need thereof a therapeutically effective amount of an isolated polypeptide, or a pharmaceutically acceptable salt thereof, in which the polypeptide comprises an amino acid sequence chosen from SEQ ID NOs: 57-69.

In one embodiment of the invention, a polypeptide of the invention is used for treatment and/or prevention of an αvβ3 integrin-associated disease, which includes, but is not limited to, osteoporosis, cancer, bone tumor or cancer growth and symptoms related thereto, angiogenesis-related tumor growth and metastasis, tumor metastasis in bone, malignancy-induced hypercalcemia, angiogenesis-related eye diseases, Paget's disease, rheumatic arthritis, and osteoarthritis.

In another embodiment of the invention, a polypeptide of the invention is used for treatment and/or prevention of an angiogenesis-related eye disease, which includes, but is not limited to, age-related macular degeneration, diabetic retinopathy, corneal neovascularizing diseases, ischaemia-induced neovascularizing retinopathy, high myopia, and retinopathy of prematurity.

In still another embodiment of the invention, a polypeptide of the invention is used for treatment and/or prevention of osteoporosis. The osteoporosis is associated with a pathological condition chosen from post-menopausal estrogen deficiency, secondary osteoporosis, rheumatoid arthritis, ovariectomy, Paget's disease, bone cancer, bone tumor, osteoarthritis, increased osteoclast formation, and increased osteoclast activity. Furthermore, the osteoporosis includes, but is not limited to, an ovariectomy-induced osteoporosis or bone loss and post-menopausal osteoporosis or bone loss.

Yet another aspect of the invention is a method of using a disintegrin variant for treatment and/or prevention of physiological changes in a mammal including a human induced by ovariectomy or post-menopausal osteoporosis. The method includes administering to the mammal in need thereof a therapeutically effective amount of an isolated polypeptide, or a pharmaceutically acceptable salt thereof, which has integrin αvβ3 receptor-antagonist activity and substantially reduced integrin αIIbβ3 and/or α5β1 receptor-blocking activity as compared to a wild-type disintegrin, and thereby resulting in treatment and/or prevention of the ovariectomy-induced physiological change in the mammal. The polypeptide is encoded by a modified disintegrin nucleotide sequence that encodes a modified amino acid sequence resulting in said polypeptide having substantially reduced integrin αIIbβ3 and/or α5β1 receptor-blocking activity. The disintegrin nucleotide sequence may be derived from a snake venom, and may be chosen from one of rhodostomin, albolabrin, applagin, basilicin, batroxostatin, bitistatin, cereberin, cerastin, crotatroxin, durissin, elegantin, flavoridin, flavostatin, halysin, halystatin, jararacin, jarastatin, kistrin, lachesin, lutosin, molossin, salmosin, saxatilin, tergeminin, trimestatin, trimucrin, trimutase, ussuristatin, and viridin.

The polypeptide variant used for treatment and/prevention of an ovariectomy-induced or post-menopausal physiological change in the mammal may contain an RGD motif variant that comprises an amino acid sequence chosen from SEQ ID NOs: 30-42.

In one embodiment of the invention, the method includes administering to the mammal in need thereof a therapeutically effective amount of an isolated polypeptide, or a pharmaceutically acceptable salt thereof, in which the polypeptide variant comprises an amino acid sequence chosen from SEQ ID NOs: 57-69. In another embodiment, the polypeptide variant is pegylated or conjugated with albumin or conjugated with a tissue target molecule.

Yet another aspect of the invention is a method of using a disintegrin variant for inhibition and/or prevention of tumor cell growth in bone and symptoms related thereto in a mammal including a human. The method includes administering to the mammal in need thereof a therapeutically effective amount of an isolated polypeptide, or a pharmaceutically acceptable salt thereof, which has integrin $\alpha v\beta 3$ receptor-antagonist activity and substantially reduced integrin $\alpha IIb\beta 3$ and/or $\alpha 5\beta 1$ receptor-blocking activity as compared to a wild-type disintegrin, and thereby resulting in inhibition and/or prevention of tumor cell growth in bone and symptoms related thereto in the mammal. The polypeptide is encoded by a modified disintegrin nucleotide sequence that encodes a modified amino acid sequence and thereby results in said polypeptide having substantially reduced integrin $\alpha IIb\beta 3$ and/or $\alpha 5\beta 1$ receptor-blocking activity.

The disintegrin nucleotide sequence may be derived from a snake venom, and may be chosen from rhodostomin, albolabrin, applagin, basilicin, batroxostatin, bitistatin, cereberin, cerastin, crotatroxin, durissin, elegantin, flavoridin, flavostatin, halysin, halystatin, jararacin, jarastatin, kistrin, lachesin, lutosin, molossin, salmosin, saxatilin, tergeminin, trimestatin, trimucrin, trimutase, ussuristatin, and viridin.

The pathological symptoms related to tumor cell growth in bone include an increased osteoclast activity, an increased bone resorption, bone lesion, hypercalcemia, a body weight loss, and any combinations thereof. The tumor cell growth in bone includes bone cancer cells and metastasized cancer cells originating from prostate cancer, breast cancer, lung cancer, renal cancer, ovarian cancer, pancreatic cancer, myeloma cancer, hepatoma, and melanoma.

In one embodiment of the invention, the method includes administering to a mammal in need thereof a therapeutically effective amount of an isolated polypeptide, or a pharmaceutically acceptable salt thereof, in which the polypeptide is a variant of rhodostomin, in which rhodostomin comprises the amino acid sequence defined by SEQ ID NO: 1, and the variant comprises an RGD motif variant. The RGD motif variant may comprise an amino acid sequence chosen from SEQ ID NOs: 30-42.

In another embodiment of the invention, the method includes the step of administering to a mammal in need thereof a therapeutically effective amount of an isolated polypeptide, or a pharmaceutically acceptable salt thereof, in which the polypeptide comprises an amino acid sequence chosen from SEQ ID NOs: 57-69. The polypeptide variant may be pegylated or conjugated with albumin or conjugated with a tissue target molecule.

Yet another aspect of the invention is a method for making a polypeptide of the invention, the method comprising the steps as follows: (a) transforming a host cell with a polynucleotide encoding said polypeptide to obtain one or more than one transformant; (b) selecting a transformant having one or more than one copy of said DNA construct inserted into the tansformant; (c) growing the transformant in a culture medium to amplify cell population thereof; (d) harvesting transformant cells; (e) growing the harvested transformant cells in a culture medium free of amino acids; and (g) collecting supernatant to obtain said polypeptide.

The aforementioned step (e) may further comprise the step of adding methanol to the culture medium to induce the polypeptide expression in the transformant cells. In one embodiment, the step (g) may further comprise the step of performing column chromatography to obtain said polypeptide. In a further embodiment, the aforementioned method may further comprise the step of performing HPLC to obtain the purified, isolated polypeptide.

These and other aspects of the present invention are more specifically described below.

Human recombinant RANKL and M-CSF were purchased from R&D Systems (Minneapolis, Minn.). The C-terminal telopeptides of type-I collagen ELISA kit was obtained from Cross Laps (Herlev, Denmark). All other chemicals were obtained from Sigma.

EXAMPLE 1

Construction of DNAs Encoding Rhodostomin and Variants

Rhodostomin was cloned and expressed in the vector pGEX-2KS as a template. The DNA encoding Rho was composed of codons preferentially used in *Pichia pastoris*. Rho DNA was amplified by the polymerase chain reaction (PCR) with the sense primer 5'-GAATTCGAATTCCATCATCATCATCATCAT CATGGTAAGGAATGTGACTGTTCTT-3' (Rho-Pic-1; SEQ ID NO: 3) that had Eco R1 recognition and six histidine residues for facilitating purification. The antisense primer is 5'-CCGCGGCCGCGGTCAGTGGTATCTTGGACAGTCAGC-3' or 5'-CCGCGGCCGCGGTTAGTGGTATCTTGGACAGTCAGC-3' (Rho-Pic-2; SEQ ID NO: 4) with Sac II recognition and a TCA (or TTA) stop codon. The PCR product was purified and then ligated into the Eco R1 and Sac II sites of the yeast recombination vector, pPICZαA. The recombinant plasmid was used to transform a DH5α strain, and colonies were selected on agar plates with low salt LB (1% tryptone, 0.5% yeast extract, 0.5% NaCl, 1.5% agar at pH 7.0) and 25 μg/ml antibiotic Zeocin.

Rhodostomin variants were synthesized and amplified by the polymerase chain reaction (PCR) using an overlapping oligonucleotide strategy with primers containing Eco RI and Sac II restriction sites. The nucleotide sequences of various primers used for synthesizing or confirming variants are listed in Table 1. RD-HSA fusion protein was constructed using similar procedures. The cDNA of human serum albumin was purchased from Invitrogen, and the structural gene of albumin was fused at N-terminus of Rho gene with a GSGSGS linker amino acid sequence and with six histidine residues at the N-terminus.

TABLE 1

| Primer | | Sequence | SEQ ID NO: |
|---|---|---|---|
| RLD-1 | Sense | GAATCCCAAGACTTGACATGCCAG | (SEQ ID NO: 5) |
| RLD-2 | Anti-sense | CTGGCATGTCAAGTCTTGGGATTC | (SEQ ID NO: 6) |
| RHD-1 | Sense | AGAATCCCAAGACACGACATGCCAGAC | (SEQ ID NO: 7) |
| RHD-2 | Anti-sense | GTCTGGCATGTCGTGTCTTGGGATTCT | (SEQ ID NO: 8) |
| RID-1 | Sense | AGAATCCCAAGAATCGACATGCCAGAC | (SEQ ID NO: 9) |
| RID-2 | Anti-sense | GTCTGGCATGTCGATTCTTGGGATTCT | (SEQ ID NO: 10) |
| P48A-1 | Sense | TGTAGAATCGCTAGAGGTGACATG | (SEQ ID NO: 11) |

TABLE 1-continued

| Primer | | Sequence | SEQ ID NO: |
|---|---|---|---|
| P48A-2 | Anti-sense | CATGTCACCTCTAGCGATTCTACA | (SEQ ID NO: 12) |
| ARGD-2 | Anti-sense | GTCACCTCTTGCGATTCTACAG | (SEQ ID NO: 13) |
| RGDNP-1 | Sense | CAAGAGGTGACAACCCAGACGACAG | (SEQ ID NO: 14) |
| RGDNP-2 | Anti-sense | CTGTCGTCTGGGTTGTCACCTCTTG | (SEQ ID NO: 15) |
| RGDDP-1 | Sense | CAAGAGGTGACGACCCAGACGACAG | (SEQ ID NO: 16) |
| RGDDP-2 | Anti-sense | CTGTCGTCTGGGTCGTCACCTCTTG | (SEQ ID NO: 17) |
| RGDGP-1 | Sense | CAAGAGGTGACGGTCCAGACGACAGATG | (SEQ ID NO: 18) |
| RGDGP-2 | Anti-sense | CATCTGTCGTCTGGACCGTCACCTCTTG | (SEQ ID NO: 19) |
| RGDDL-1 | Sense | CAAGAGGTGACGACCTAGACGACAGATG | (SEQ ID NO: 20) |
| RGDDL-2 | Anti-sense | CATCTGTCGTCTAGGTCGTCACCTCTTG | (SEQ ID NO: 21) |
| RGDDM-1 | Sense | CAAGAGGTGACGACATGGACGACAGATG | (SEQ ID NO: 22) |
| RGDDM-2 | Anti-sense | CATCTGTCGTCCATGTCGTCACCTCTTG | (SEQ ID NO: 23) |
| RGDDV-1 | Sense | CAAGAGGTGACGACGTAGACGACAGATG | (SEQ ID NO: 24) |
| RGDDV-2 | Anti-sense | CATCTGTCGTCTACGTCGTCACCTCTTG | (SEQ ID NO: 25) |
| α-factor | | TATTGCCAGCATTGCTGC | (SEQ ID NO: 26) |
| 5'-AOX1 | Sense | GACTGGTTCCAATTGACAAGC | (SEQ ID NO: 27) |
| 3'-AOX1 | Anti-sense | GCAAATGGCATTCTGACATCC | (SEQ ID NO: 28) |
| RLDDL-1 | Sense | CAAGACTTGACGACCTAGAC | (SEQ ID NO: 74) |
| RLDD-2 | Anti-sense | GTCGTCAAGTCTTGGGATTC | (SEQ ID NO: 75) |
| RGDDL-1 | Sense | CAAGACTTGACGACCTAGAC | (SEQ ID NO: 76) |
| ARLDD-2 | Anti-sense | GTCGTCAAGTCTTGCGATTC | (SEQ ID NO: 77) |

Note: Primer α-factor was used as a sequencing primer; 5'-AOX1 & 3'-AOX1 primers were used for checking for the presence of the inserted DNA.

The polymerase chain reactions were carried out at 95° C. for 1 min, 55° C. for 1 min, then 72° C. for 1 min for 25 cycles. A mixture of primers was also used for generating multiple mutation sites. The PCR products were separated on 2% agarose gels and visualized by ethidium bromide staining. The desired PCR products were purified and then ligated into the Eco RI and Sac II sites of the yeast transfer vector pPICZα A. The recombinant plasmid was used to transform an *Escherichia coli* XL1-blue strain and colonies selected on agar plates containing antibiotic Zeocin. The *E. coli* XL1-blue colonies were picked, plasmid DNA isolated, and the sequence confirmed by sequencing the insert. Table 2 lists primer sequence ID NOs. used for synthesizing DNAs encoding Rhodostomin and various variants.

TABLE 2

Primers for synthesizing DNAs encoding Rhodostomin and various variants

| Sense Primer | Antisense Primer | Rhodostomin Variant |
|---|---|---|
| SEQ ID NO: 3 | SEQ ID NO: 4 | (Rho) $^{48}$PRGDMP$^{53}$ |
| SEQ ID NO: 16 | SEQ ID NO: 13 | Variant $^{48}$ARGDDP$^{53}$ |
| SEQ ID NO: 24 | SEQ ID NO: 13 | Variant $^{48}$ARGDDV$^{53}$ |
| SEQ ID NO: 70 | SEQ ID NO: 71 | Variant $^{48}$ARGDDL$^{53}$ |
| SEQ ID NO: 20 | SEQ ID NO: 21 | Variant $^{48}$PRGDDL$^{53}$ |
| SEQ ID NO: 72 | SEQ ID NO: 73 | Variant $^{48}$ARGDDM$^{53}$ |
| SEQ ID NO: 22 | SEQ ID NO: 23 | Variant $^{48}$PRGDDM$^{53}$ |
| SEQ ID NO: 5 | SEQ ID NO: 6 | Variant $^{48}$PRLDMP$^{53}$ |
| SEQ ID NO: 74 | SEQ ID NO: 75 | Variant $^{48}$PRLDDL$^{53}$ |
| SEQ ID NO: 76 | SEQ ID NO: 77 | Variant $^{48}$ARLDDL$^{53}$ |
| SEQ ID NO: 9 | SEQ ID NO: 10 | Variant $^{48}$PRIDMP$^{53}$ |
| SEQ ID NO: 7 | SEQ ID NO: 8 | Variant $^{48}$PRHDMP$^{53}$ |
| SEQ ID NO: 14 | SEQ ID NO: 15 | Variant $^{48}$PRGDNP$^{53}$ |
| SEQ ID NO: 18 | SEQ ID NO: 19 | Variant $^{48}$PRGDGP$^{53}$ |

EXAMPLE 2

Protein Expression and Purification of Rhodostomin and Variants

The protein expression of rhodostomin and its variants in *Pichia* was performed according to the protocols of the *Pichia* EasyComp™ Kit with minor modifications. Briefly, a total of 10 μg plasmids containing DNA encoding rhodostomin or its variants were purified and digested with Sac I to linearize the plasmids. *Pichia* strain X33 was transformed with the linearized constructs by a heat shock method, using a *Pichia* EasyComp™ kit from Invitrogen®. The transformant integrated at the 5' AOX1 locus by a single crossover. PCR was used to analyze *Pichia* integrants to determine if the Rho gene had been integrated into the *Pichia* genome, and cells were lysed by Lyticase (Sigma). Colonies were selected on agar plates containing YPD (1% yeast extract, 2% peptone, 2% glucose, and 2% agar) and 100 μg/ml Zeocin. A number of clones with multiple copies of Rho gene insertions were selected to pick the clone having the highest Rho protein expression.

Recombinant Rho and its variants were produced as follows: Selected colonies were grown in the YPD medium (1% yeast extract, 2% peptone, and 2% dextrose) containing 100 μg/ml Zeocin™ at 30° C. After 48 hours, cells were collected by centrifugation and grown in 1 liter of minimal methanol medium (containing 1.34% yeast nitrogen base with ammonium sulfate without amino acids and $4\times10^{-5}$% biotin). A total of 1% methanol was added once every 24 hours to induce Rho or variant expression for 2 days. The supernatant was collected by centrifugation and dialyzed twice against 5 liter buffer A (5 mM EDTA, 8M urea and 10 mM Na-phosphate buffer, pH 7.7). The final solution was loaded into a nickel-chelating column and eluted with a gradient of 200 mM imidazole. The recombinant rhodostomin and its variants were further purified by HPLC (reverse phase C18 HPLC). The purified recombinant Rho had a purity of greater than 95% as judged by Tricine-SDS-PAGE.

Rho and its variants were subsequently subjected to electrospray mass spectrometry analyses for checking the molecular weight. The amino acid sequences of the RGD motifs of Rho and variants are shown in Table 3.

TABLE 3

| SEQ ID NO. | RGD Motif and Variants thereof | Abbreviation |
|---|---|---|
| 2 | $^{49}$Arg-Gly-Asp$^{51}$ | $^{49}$RGD$^{51}$ |
| 29 | $^{48}$Pro-Arg-Gly-Asp-Met-Pro$^{53}$ (Wild type) | $^{48}$PRGDMP$^{53}$ |
| 30 | $^{48}$Ala-Arg-Gly-Asp-Asp-Pro$^{53}$ | $^{48}$ARGDDP$^{53}$ |
| 31 | $^{48}$Ala-Arg-Gly-Asp-Asp-Val$^{53}$ | $^{48}$ARGDDV$^{53}$ |
| 32 | $^{48}$Ala-Arg-Gly-Asp-Asp-Leu$^{53}$ | $^{48}$ARGDDL$^{53}$ |
| 33 | $^{48}$Pro-Arg-Gly-Asp-Asp-Leu$^{53}$ | $^{48}$PRGDDL$^{53}$ |
| 34 | $^{48}$Ala-Arg-Gly-Asp-Asp-Met$^{53}$ | $^{48}$ARGDDM$^{53}$ |
| 35 | $^{48}$Pro-Arg-Gly-Asp-Asp-Met$^{53}$ | $^{48}$PRGDDM$^{53}$ |
| 36 | $^{48}$Pro-Arg-Leu-Asp-Met-Pro$^{53}$ | $^{48}$PRLDMP$^{53}$ (RD) (RLD) |
| 36 | $^{48}$Pro-Arg-Leu-Asp-Met-Pro$^{53}$ (pegylated) | *$^{48}$PRLDMP$^{53}$-5K |
| 37 | $^{48}$Pro-Arg-Leu-Asp-Asp-Leu$^{53}$ | $^{48}$PRLDDL$^{53}$ |
| 38 | $^{48}$Ala-Arg-Leu-Asp-Asp-Leu$^{53}$ | $^{48}$ARLDDL$^{53}$ |
| 39 | $^{48}$Pro-Arg-Ile-Asp-Met-Pro$^{53}$ | $^{48}$PRIDMP$^{53}$ (RID) |
| 40 | $^{48}$Pro-Arg-His-Asp-Met-Pro$^{53}$ | $^{48}$PRHDMP$^{53}$ |
| 41 | $^{48}$Pro-Arg-Gly-Asp-Asn-Pro$^{53}$ | $^{48}$PRGDNP$^{53}$ |
| 42 | $^{48}$Pro-Arg-Gly-Asp-Gly-Pro$^{53}$ | $^{48}$PRGDGP$^{53}$ (PGP) |

*$^{48}$PRLDMP$^{53}$-5K refers to pegylated $^{48}$PRLDMP$^{53}$.

EXAMPLE 3

Effects of RD and its Derivatives on Bleeding Time

Measurement of bleeding time was performed as follows: Mice were anaesthetized with trichloroacetaldehyde (200 mg/kg), and bleeding time was measured by a method described previously, with minor modifications. Saline or proteins were injected intravenously through the tail vein of the mouse (ICR, male, with an average body weight of 23.5±1.8 g). A sharp cut of 0.5 mm from the tail tip of the mouse was made 5 min after injection. The tail was then immediately immersed in a saline-filled beaker, kept at 37° C., and the bleeding time was measured.

FIG. 1 shows the effects of RD and ARLDDL proteins on tail bleeding time in mice. Tail bleeding time was measured 5 min after intravenous administration of saline, RD, ARLDDL, rhodostomin (0.6 mg/kg for each) of HSA-RD (5 mg/kg). An intravenous injection of rhodostomin (0.5 mg/kg) exerted a pronounced effect in prolonging the clotting time in mice. However, both RD and ARLDDL (0.5 mg/kg), which exerted selectivity for αvβ3 integrin, only slightly affected the clotting time in mice as compared to rhodostomin. Results are expressed as the mean±S.E.M (n=6).

EXAMPLE 4

Platelet aggregation Assay

Venous blood (9 parts) samples from healthy donors who had not received any medication for at least two weeks were collected in 3.8% sodium citrate (1 part). Blood samples were centrifuged at 150×g for 10 min to obtain platelet-rich plasma (PRP) and allowed to stand for 5 min, and PRP was collected. The platelet-poor plasma (PPP) was prepared from the remaining blood by centrifuging at 2000×g for 25 min. The PPP platelet count was measured on a hematology analyzer and diluted to 250,000 platelets/μl. A solution of 190 μl of PRP and 10 μl of either Rho or PBS buffer were incubated for 5 min in a Hema Tracer 601 aggregometer at 37° C. Ten microliters of 200 μM adenosine diphosphate (ADP) were further added to monitor the response of platelet aggregation by light transmission.

EXAMPLE 5

Cell Adhesion Inhibition Assay

Cell adhesion inhibition assays were performed as described previously in Zhang, X. P., Kamata, T., Yokoyama, K., Puzon-McLaughlin, W., and Takada, Y. (1998) *Specific interaction of the recombinant disintegrin-like domain of MDC*-15 (*metargidin, ADAM*-15) *with integrin alphavbeta*3, J Biol Chem 273:7345-7350. Briefly, wells of 96-well Immulon-2 microtiter plates (Costar, Corning, USA) were coated with 100 μl of phosphate-buffered saline (PBS: 10 mM phosphate buffer, 0.15M NaCl, pH 7.4) containing substrates at a concentration of 50-500 nM, and incubated overnight at 4° C. The substrates and their coating concentrations were fibrinogen (Fg) 200 μg/ml, vitronectin (Vn) 50 μg/ml, and fibronectin (Fn) 25 μg/ml. Non-specific protein binding sites were blocked by incubating each well with 200 μl of heat-denatured 1% bovine serum albumin (BSA, Calbiochem) at room temperature (25° C.) for 1.5 hr. The heat-denatured BSA was discarded and each well was washed twice with 200 μl of PBS.

Chinese hamster ovary (CHO) cells expressing αvβ3 (CHO-αvβ3) and αIIbβ3 (CHO-αIIbβ3) integrins were maintained in 100 μl of Dulbecco's Modified Eagle's Medium (DMEM) medium. Chinese hamster ovary (CHO) cells expressing integrins αvβ3 (CHO-αvβ3) and αIIbβ3 (CHO-αIIbβ3) were kindly provided by Dr. Y. Takada (Scripps Research Institute). Human erythroleukemia K562 cells were purchased from ATCC and cultured in the RPMI-1640 medium containing 5% fetal calf serum. CHO and K562 cells growing in log phase were detached by trypsinization and used in the assay at $3\times10^5$ and $2.5\times10^5$ cells/ml, respectively. Rho and its variants were added to the cultured cells and incubated at 37° C., 5% $CO_2$ for 15 minutes. Rho and its variants were used as inhibitors at the concentrations of 0.001-500 μM. The treated cells were then added into the coated plate and reacted at 37° C., 5% $CO_2$ for 1 hour. The incubation solution was then discarded and non-adhered cells were removed by washing twice with 200 μl PBS. Bound cells were quantified by crystal violet staining. Briefly, the well was fixed with 100 μl of 10% formalin for 10 minutes and dried. Fifty microliters of 0.05% crystal violet were then added into the well at room temperature for 20 minutes. Each well was washed with 200 μl of distilled water four times and dried. Colorization was carried out by adding 150 μl of colorizing solution (50% alcohol and 0.1% acetic acid). The resulting absorbance was read at 600 nm and the readings were correlated with the number of adhering cells. Inhibition was defined as % inhibition=100−[$OD_{600}$ (rhodostomin variant-treated sample)/$OD_{600}$ (untreated sample)]×100.

EXAMPLE 6

Inhibitory Effects of RD and its Derivatives on Integrins αvβ3, αIIbβ3, and α5β1

The $IC_{50}$ of RD and its derivatives on integrin binding was obtained by the cell adhesion assay as described in Example 5 above. Briefly, matrix proteins such as fibronectin, vitronectin, or fibrinogen, were coated at a fixed concentration on microtiter plates, as described in Example 5, and Rho and its variants were added to the cells expressing integrin at different concentrations ranging from 0.001-500 μM to obtain an $IC_{50}$. The lower the $IC_{50}$, the greater the specificity or potency of the variant.

The modification of the RGD motif of Rho had unique effects on Rho's biological activities: the activity in inhibiting the integrin αIIbβ3 or α5β1's binding to the matrix proteins was reduced and the selectivity to the integrin αvβ3 was increased as a result of the sequence modification. Table 4 shows the result of $IC_{50}$ for inhibition of cell adherence by Rho and its derivatives.

TABLE 4

Inhibition of Cell adhesion to ECM by RD and its Derivatives

| RGD motif variant & SEQ ID NO: | IC50 (nM) αIIbβ3/Fg | IC50 (nM) αvβ3/Fg | IC50 (nM) α5β1/Fn |
|---|---|---|---|
| $^{48}$PRGDMP$^{53}$ (29) | 21.0 ± 11.2 (17[a]) | 13.0 ± 5.7 (20) | 256.8 ± 87.5 (21) |
| $^{48}$ARGDDP$^{53}$ (30) | 850.9 ± 322.6 (3) | 45.3 ± 17.4 (3) | 5044.5 ± 1554.5 (3) |
| $^{48}$ARGDDV$^{53}$ (31) | 255.2 ± 107.2 (3) | 15.8 ± 5.5 (3) | 213.1 ± 74.4 (3) |
| $^{48}$ARGDDL$^{53}$ (32) | 1518.1 ± 740.4 (4) | 41.3 ± 16.0 (5) | 526.7 ± 200.3 (5) |
| $^{48}$PRGDDL$^{53}$ (33) | 1224.0 ± 231.2 (4) | 76.0 ± 16.0 (4) | 3017.0 ± 801.5 (3) |
| $^{48}$ARGDDM$^{53}$ (34) | 627.2 ± 317.6 (3) | 49.0 ± 19.2 (6) | 350.8 ± 81.0 (4) |
| $^{48}$PRGDDM$^{53}$ (35) | 1117.8 ± 379.7 (3) | 211.0 ± 91.3 (5) | 4047.3 ± 1784.3 (4) |
| $^{48}$PRLDMP$^{53}$ (36) | 2219.8 ± 996.9 (6) | 35.0 ± 14.1 (5) | 3043.3 ± 1117.6 (4) |
| *$^{48}$PRLDMP$^{53}$-5K | 2408.0 ± 1090.0 (2) | 114.8 ± 51.1 (4) | >3730 (3) |
| $^{48}$PRLDDL$^{53}$ (37) | >5880 (3) | 342.3 ± 110.1 (3) | >5880 (4) |
| $^{48}$ARLDDL$^{53}$ (38) | 59217.8 ± 966.4 (3) | 36.8 ± 12.8 (3) | 23171.0 ± 925.5 (3) |
| $^{48}$PRIDMP$^{53}$ (39) | >5880 (2) | 119.9 ± 19.7 (3) | >5880 (3) |
| $^{48}$PRHDMP$^{53}$ (40) | 2109.0 ± 810.0 (3) | 131.6 ± 35.3 (3) | >5880 (3) |
| $^{48}$PRGDNP$^{53}$ (41) | 185.0 ± 61.7 (4) | 24.8 ± 13.1 (5) | 357.0 ± 80.6 (3) |
| $^{48}$PRGDGP$^{53}$ (42) | 2591.0 ± 572.2 (3) | 204.1 ± 87.0 (3) | 3462.0 ± 1525.5 (4) |

*$^{48}$PRGDMP$^{53}$ (29) refers to the RGD motif of Rho and comprises an amino acid sequence set forth by SEQ ID NO: 29; $^{48}$PRLDMP$^{53}$ (36) refers to the RGD motif variant of RD and comprises an amino acid sequence set forth by SEQ ID NO: 36.

[a]The numbers represents the numbers of experiments.

The rhodostomin variants have a much lower affinity to αIIbβ3 and/or α5β1 as compared to the Rho (Table 4). As shown in Table 4, for example, the $IC_{50}$ of RD (i.e., PRLDMP) in inhibition of integrins αIIbβ3 and α5β1 increased more than 104 and 10-fold, respectively, as compared to that of the Rho. Moreover, the $IC_{50}$ of ARLDDL in inhibition of integrins αIIbβ3 and α5β1 increased more than 2000-fold compared to that of the Rho. The $IC_{50}$ of pegylated RD and human albumin-conjugated RD on αIIbβ3 binding increased 113.7- and 129.9-fold, respectively, as compared to that of the Rho (Table 5). Therefore, the variants' affinities to platelets were markedly reduced compared to that of Rho (Table 5).

EXAMPLE 7

Effects of RD and its Derivatives on Osteoclastogenesis

Osteoclasts are specialized monocyte/macrophage family members that differentiate from bone marrow hematopoietic precursors. Cultures of osteoclast precursors in the presence of M-CSF (20 ng/ml) and sRANKL (50 ng/ml) for 8 days induced the formation of large mature osteoclasts with multinuclei, which were characterized by the acquisition of mature phenotypic markers, such as TRAP. The method of osteoclastogenesis from cultured hematopoietic cells of bone marrow and the effects of RD and its derivatives on osteoclastogenesis were investigated as follows.

Bone marrow cells were prepared by removing femurs from 6~8-week-old SD rats and flushing the bone marrow cavity with a-MEM which was supplemented with 20 mM HEPES and 10% heat-inactivated FCS, 2 mM-glutamine, penicillin (100 U/ml) and streptomycin (100 μg/ml). The non-adherent cells (hematopoietic cells) were collected and used as osteoclast precursors after 24 hr. Cells were seeded at $1\times10^6$ cells/well (0.5 ml) in 24-well plates in the presence of human recombinant soluble RANKL (50 ng/ml) and murine M-CSF (20 ng/ml). The culture medium was replaced every 3 days. Osteoclast formation was confirmed by an assay of tartrate-resistant acid phosphatase (TRAP) on day-8. In brief, adherent cells were fixed with 10% formaldehyde in phosphate-buffered saline for 3 min. After treatment with ethanol/acetone (50:50 v/v) for 1 min, the cell surface was air-dried and incubated for 10 min at room temperature in an acetate buffer (0.1 M sodium acetate, pH 5.0) containing 0.01% naphthol AS-MX phosphate (Sigma) and 0.03% fast red violet LB salt (Sigma) in the presence of 50 mM sodium tartrate. Osteoclast-like TRAP-positive cells in each well were scored by counting the number of TRAP-positive and multinucleated cells containing more than three nuclei.

RD derivatives markedly inhibited the differentiation of osteoclasts, which was correlated with their inhibitory activities on αvβ3 (Table 5). On the other hand, AKGDWN and PRGEMP were less effective in inhibiting integrin αvβ3 and differentiation of osteoclasts (Table 5).

TABLE 5

Inhibition of Platelet Aggregation, Cell adhesion, and Osteoclastogenesis by RD and its Derivatives

| | IC50 (nM) | | | | |
|---|---|---|---|---|---|
| | Platelet aggregation | αvβ3 | α5β1 | αIIbβ3 | Osteoclastogenesis |
| Rhodostomin | 83 | 13 | 257 | 21 | 5.52 |
| ARGDDL | 455 | 41 | 527 | 1518 | 8.02 |
| PGP | 283 | 24 | 4000 | 500 | 5.76 |
| RD | 433 | 35 | 3043 | 2220 | 3.32 |
| RID | 448 | 120 | >5850 | >5850 | 5.82 |
| PRGDDL | 396 | 76 | 3017 | 1224 | 3.15 |
| ARLDDL | 10380 | 37 | 23171 | 59217 | — |
| PRPDDL | 3530 | 188 | 21381 | 13590 | |
| AKGDWN | 138 | 96637 | >119000 | 69 | 78400 |
| PRGEMP | 4908 | >17850 | >5950 | >59500 | 68200 |
| Pegylated-RD | 398 | 115 | >5880 | 2408 | 3.88 |
| HSA-RD | 438 | 45 | >5880 | 2750 | 6.68 |

EXAMPLE 8

Ovariectomy-Induced Osteoporosis

Female Sprague-Dawley rats (3 months old, 270~290 g) or ICR mice (4 weeks old, 22~28 g) were used for this study. Rats or mice were ovariectomized (OVX) bilaterally under trichloroacetaldehyde anesthesia and control rats were sham-operated (Sham) for comparison. The animals were all kept under controlled conditions at the room temperature (22±1° C.) and a 12-hr light-dark cycle. Animals were fed with Purina Laboratory Rodent Diet (PMI; St. Louis, Mo.) (0.95% calcium) and water ad libitum. The body weights of the rats were recorded weekly.

EXAMPLE 9

Analysis of Bone Mineral Density (BMD) and Content (BMC)

At the end of the experiment, rats or mice were sacrificed by decapitation. The tibia and femur were removed, cleaned of soft tissue, and the length and weight of the tibia and femur were measured with a precision caliper (±0.05 mm) as described by Weinreb M, Rodan G A, Thompson D D., (1991) *Depression of osteoblastic activity in immobilized limbs of suckling rats*, J Bone Miner Res 6:725-731. BMD and BMC of the tibia were measured with a dual-energy X-ray absorptiometer (DEX, XR-26; Norland, Fort Atkinson, Wis.). The mode adapted to the measurements of small subjects was adopted. See Chih-Hsin et al., "Enhancement of Fibronectin Fibrillogenesis and Bone Formation by Basic Fibroblast Growth Factor via Protein Kinase C-Dependent Pathway in Rat Osteoblasts," Mol. Pharmacol: 66: 440-449, (2004). A coefficient of variation of 0.7% was calculated from daily measurements of BMD on a lumbar phantom for more than 1 year [22, 23]. The whole tibia and femur were scanned and BMD and BMC were measured by an absorptiometer.

EXAMPLE 10

Histomorphometry of Bone

Tibiae were fixed by 4% formaldehyde and then decalcified with 12% EDTA and dehydrated in an ascending series of ethanol solution and acetone, and embedded in paraffin. Serial sections (5 mm) were cut longitudinally and stained with Mayer's hematoxylin-eosin solution. Images of the growth plate and proximal tibia were photographed using an Olympus microscope. The bone volume was measured using an image analysis software (Image-pro plus 3.0) in the secondary spongiosa, which was located under the primary spongiosa and characterized by a network of larger trabeculae. To measure the number of osteoclasts, the sections were stained with tartrate-resistant acid phosphatase (TRAP).

EXAMPLE 11

Biomechanical Three-Point Bending Test

Mechanical properties of bone tissues were measured by performing three-point bending test in a material testing system (MTS-858, MTS System Inc., Minneapolis, Minn.). The span of the two support points was 20 millimeters and the deformation rate was 1 mm/min. Load/deformation curves were input to a computer and analyzed by Team 490 software (version 4.10, Nicolet Instrument Technologies Inc., Madison, Wis.). Cross-sectional parameters were measured from the photographs and used in the calculation of the cross-sectional moment of inertia. The cross-sectional moment of inertia was calculated under the assumption that the cross-sections were elliptically shaped [24]:

$$I=\pi[(ab3\times(a\times 2t)(b\times 2t)3)/64$$

where a is the width of the cross section in the mediolateral direction, b is the width of the cross section in the anteroposterior direction, and t is the average of the cortical thickness. All of these parameters were obtained using the image software Image Pro Plus 3.0 for Windows (Media Cybernetics, Silver Spring, Md.). The maximal stress, ultimate stress, and elastic modulus (Young's modulus) were calculated using the following equations [25]:

$$\sigma=FLc/4I$$

$$E=F/d \ni L3/48I$$

where σ is ultimate stress, c is the distance from the center of mass (equal to ½ b as described above), F is the applied load (N), d is the displacement (mm), and L is the span between the two support points of the bending fixture (mm). In addition, the energies in the ultimate stress were measured by computing the respective areas under the stress-strain curve.

EXAMPLE 12

Inhibition of OVX-Induced Bone Loss by RD Derivatives in Mice

To examine the effects of RD derivatives on bone loss, osteoporosis was induced in female mice by ovariectomy (OVX), as described in Example 8. OVX mice showed a decrease in BMD and BMC of total body. Treatment with RD derivatives (I.M., 1.5 mg/kg/alternate day) or alendronate (p.o., 1.5 mg/kg/alternate day) for 2 weeks inhibited the loss of BMD and BMC (Table 6). The blood concentration of the C-terminal telopeptide of collagen can reflect the osteoclastic activity. As shown in Table 6, RD derivatives or alendronate also inhibited ovariectomy-induced increase in osteoclast activity (Table 6). It appeared that some of the RD derivatives were much more effective than alendronate. In addition, treatment with RD (I.M., 1.5 mg/kg) once per week for 2 weeks also inhibited the loss of BMD and BMC (Table 6). These data indicate that RD and its derivatives may inhibit osteoporosis at longer dosing intervals.

TABLE 6

Inhibition of OVX-induced bone loss by RD and its derivatives in mice

| | BMD (g/cm$^2$) | BMC (g) | C-terminal telopeptide of COL(1)α1 chain (ng/ml) |
|---|---|---|---|
| (Alternate day) | | | |
| Sham | 0.095 ± 0.001 | 0.649 ± 0.011 | 395 ± 11.9 |
| OVX | 0.075 ± 0.002* | 0.517 ± 0.007* | 686 ± 12.1* |
| OVX + RD | 0.091 ± 0.001§ | 0.627 ± 0.008§ | 391 ± 8.3§ |
| OVX + PGP | 0.092 ± 0.001§ | 0.621 ± 0.006§ | 372 ± 24.2§ |
| OVX + ARGDDL | 0.093 ± 0.001§ | 0.624 ± 0.007§ | 389 ± 16.4§ |
| OVX + RID | 0.091 ± 0.001§ | 0.622 ± 0.004§ | 391 ± 12§ |
| OVX + Rhodostomin | 0.090 ± 0.001§ | 0.619 ± 0.006§ | 397 ± 13.6§ |
| OVX + PRLDDL | 0.091 ± 0.002§ | 0.563 ± 0.056§ | 410 ± 25.1§ |
| OVX + Alendronate | 0.086 ± 0.002§ | 0.607 ± 0.051§ | 504 ± 19.6§ |
| OVX + pegylated-RD | 0.092 ± 0.002§ | 0.629 ± 0.008§ | 398 ± 9.2§ |
| (Once/week) | | | |
| OVX + RD | 0.085 ± 0.002§ | 0.582 ± 0.009§ | 533 ± 27.4§ |
| OVX + pegylated-RD | 0.087 ± 0.005§ | 0.595 ± 0.009§ | 538 ± 19.8§ |

Values are means ± SE.
*Compared with Sham-group, $p < 0.05$
§Compared with OVX-group, $p < 0.05$

EXAMPLE 13

Inhibition of Ovariectomy-Induced Bone Loss by PGP and RD Derivatives in Rats PGP (a RD derivative) was chosen to examine in more detail the protection from ovariectomy (OVX)-induced bone loss in rats. Adult female rats (3 month-old) were ovariectomized, as in Example 8, and bone volumes were measured 6 weeks after the ovariectomy, as in Examples 9-11. It was shown that PGP protein inhibited both ovariectomy-induced bone volume decrease and osteoclast number increase.

As shown in FIG. 2A, compared to the sham-operated rats (Sham), ovariectomy (OVX) caused a significant loss of the trabecular bone. However, treatment with PGP (IV, 0.3 mg/kg/day or IM, 1.5 mg/kg/alternate day) significantly inhibited the ovariectomy-induced loss of the trabecular bone in secondary spongiosa.

In FIG. 2B, tartrate-resistant acid phosphatase (TRAP) staining showed that osteoclasts were predominantly localized around the trabecular bone, and that PGP inhibited the OVX-induced increase in osteoclast formation.

OVX rats also showed an increase in body weight at the end of the experiment. Treatment with PGP (I.V., 0.3 mg/kg/day or I.M., 1.5 mg/kg/alternate day) significantly inhibited the OVX-induced increase in body weight.

Figure 2:
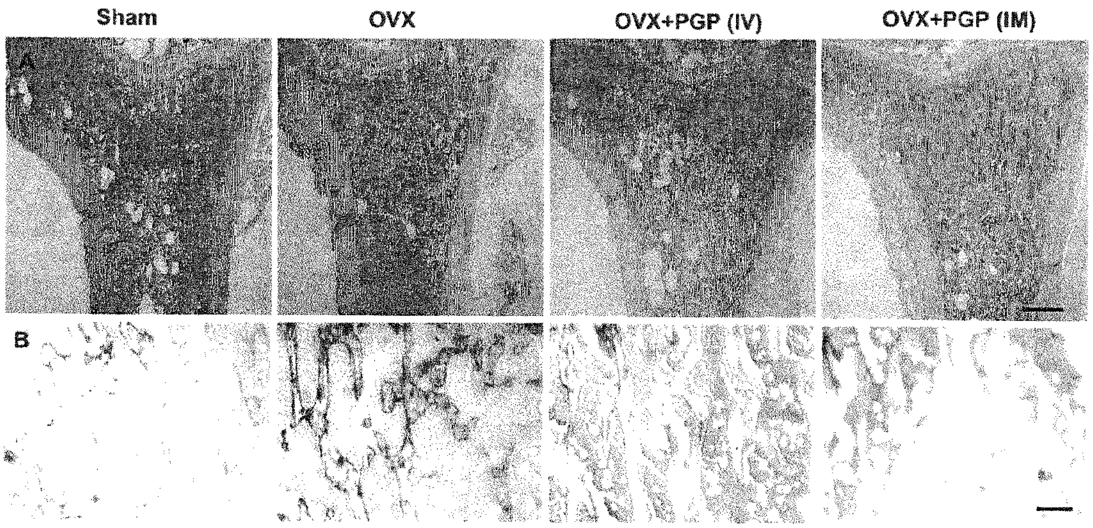
FIG. 2A are photographs of trabecular bones showing inhibition of ovariectomy-induced trabecular bone loss in rats treated with PGP protein. Bar=1 mm.
FIG. 2B are photographs of Tartrate-resistant acid phosphatase (TRAP) stained trabecular bones showing inhibition of ovariectomy-induced increase in osteoclast number in rats treated with PGP protein. Bar=100 mm.

Rats also showed a decrease in wet weight, BMD and BMC in both femur and tibia 6 weeks after the ovariectomy (Table 7). Treatment with PGP (either I.V. or I.M.) inhibited the reduction in wet weight, BMD and BMC of both tibia and femur in OVX rats. Histomorphometry demonstrated that ovariectomy caused the loss of trabecular bone in secondary spongiosa (FIG. 2). Treatment with PGP markedly reversed the loss of bone volume (FIG. 2 and Table 7). In addition, TRAP staining demonstrated that osteoclasts were predominantly localized around the trabecular bone and OVX increased the osteoclast number. A long-term administration of PGP antagonized the OVX-induced osteoclastic formation (FIG. 2 and Table 7). The serum level of the C-terminal telopeptide of collagen reflects osteoclast activity. It was found that the value was markedly increased in the OVX-group compared with that of the Sham-group, whereas treatment with PGP effectively antagonized the OVX-induced increase in osteoclast activity (Table 7).

TABLE 7

Inhibition of Ovariectomy-induced Bone Loss by PGP Protein in Rats

| | Sham (n = 22) | OVX (n = 22) | OVX + PGP(IV) (n = 13) | OVX + PGP(IM) (n = 12) |
|---|---|---|---|---|
| Bone length, mm | | | | |
| Tibia | 4.04 ± 0.01 | 4.04 ± 0.01 | 4.05 ± 0.01 | 4.04 ± 0.01 |
| Femur | 3.62 ± 0.01 | 3.62 ± 0.02 | 3.60 ± 0.02 | 3.64 ± 0.02 |
| Wet weight, mg | | | | |
| Tibia | 755.5 ± 6.3 | 647.5 ± 8.5* | 735.8 ± 8.5§ | 740.6 ± 8.7§ |
| Femur | 946.0 ± 10.9 | 850 ± 9.9* | 904.9 ± 10.2§ | 904.0 ± 13.5§ |
| BMD, $g/cm^2$ | | | | |
| Tibia | 0.108 ± 0.002 | 0.099 ± 0.015* | 0.109 ± 0.002§ | 0.111 ± 0.002§ |
| Femur | 0.131 ± 0.012 | 0.126 ± 0.003* | 0.130 ± 0.002§ | 0.136 ± 0.002§ |
| BMC, g | | | | |
| Tibia | 0.301 ± 0.011 | 0.269 ± 0.011* | 0.286 ± 0.010§ | 0.316 ± 0.009§ |
| Femur | 0.420 ± 0.005 | 0.369 ± 0.011* | 0.422 ± 0.013§ | 0.437 ± 0.009§ |
| Bone volume, % | 18.1 ± 1.5 | 9.4 ± 1.5* | 14.3 ± 1.5§ | 16.8 ± 1.8§ |
| N.Oc/BS (No/mm) | 1.77 ± 0.09 | 2.06 ± 0.17* | 1.83 ± 0.10§ | 1.81 ± 0.09§ |
| C-terminal telopeptide of collagen (n = 5 for each) | 230 ± 5.1 | 459 ± 18.4* | 259 ± 22.8§ | 221 ± 15.1§ |

ALP, alkaline phosphatase; N.Oc/BS, osteoclast number/mm bone surface.
Values are means ± SE.
*Compared with Sham-group, $p < 0.05$
§Compared with OVX-group OVX, $p < 0.05$ A three-point bending test was performed in the femur to examine the mechanical activity of the bone. Compared with the Sham-operated group, the maximal load, ultimate load, Young's modulus and ultimate stress decreased in OVX rats. Treatment with PGP exhibited a protection against the OVX-induced decrease in bone strength (Table 8). These results suggest that PGP-like protein drugs may markedly inhibit the bone loss caused by ovariectomy.

TABLE 8

Increase in biomechanical properties by PGP protein in OVX rats

| | Sham (n = 22) | OVX (n = 22) | OVX + PGP (IV) (n = 13) | OVX + PGP (IM) (n = 12) |
|---|---|---|---|---|
| Maximal load, N | 132.7 ± 4.8 | 112.1 ± 4.3* | 123.9 ± 4.9§ | 129.8 ± 7.9§ |
| Ultimate loading, N | 85.5 ± 3.7 | 70.4 ± 3.1* | 81.9 ± 2.2§ | 83.2 ± 2.5§ |
| Young's modulus, GPa | 203.7 ± 3.6 | 185.5 ± 3.3* | 194.0 ± 3.0§ | 199.9 ± 6.2§ |
| Energy to ultimate stress, $mJ/mm^3$ | 5.9 ± 0.4 | 3.5 ± 0.3* | 4.9 ± 0.8§ | 5.1 ± 0.9§ |

Values are means ± SE.
*Compared with Sham-group, $p < 0.05$
§Compared with OVX-group OVX, $p < 0.05$

EXAMPLE 14

Post-Treatment of RD Protein Inhibited OVX-Induced Osteoclast Activation

To examine the dynamic therapeutic effect of RD derivatives on osteoclast activity in vivo, osteoporosis was induced in female rats by ovariectomy and the C-terminal telopeptides of type-I collagen were measured from blood at different intervals. Compared with sham-operated rats (Sham), ovariectomy (OVX) caused a significant increase in the osteoclast activity. Measurement of the serum level of the C-terminal telopeptide of COL(1)$\alpha$1 chain showed an increase in the osteoclast activity in OVX rats. The C-terminal telopeptide of type-I collagen increased from a basal level of 361±25.6 (n=15) to 708±50.7 ng/ml (n=15) 28 days after the ovariectomy.

Figure 3:
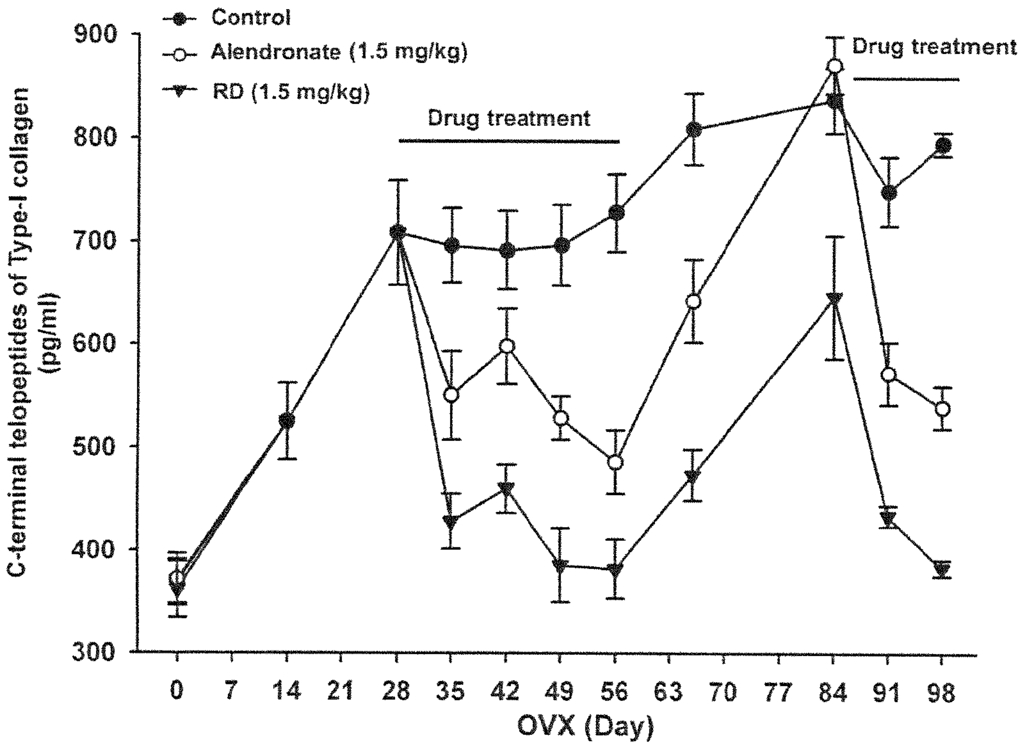
FIG. 3 is a graph showing inhibition of ovariectomy-induced osteoclast activation in rats treated with RD protein or alendronate (drug treatment), rebound of the osteoclast marker concentration during the period of drug withdrawal, and reversal of ovariectomy-induced increase in osteoclast activity during re-administration with RD or alendronate.

RD or alendronate was then post-treated one month after the ovariectomy. The post-treatment with RD (I.M., 1.5 mg/kg/alternate day) or alendronate (p.o., 1.5 mg/kg/alternate day) reversed the ovariectomy-induced increase in osteoclast activity, and RD was much more effective than alendronate (FIG. 3). Osteoclast activity recovered after the withdrawal of the RD or alendronate treatment. The recovery of osteoclast activity was much faster in the alendronate-treated group than the RD-treated group. However, re-application of RD effectively inhibited the ovariectomy-induced increase in osteoclast activity. The value of the osteoclast in response to the RD treatment was much lower than that in response to the alendronate treatment (FIG. 3). These results indicate that RD-related proteins have therapeutic effects on the bone loss caused by ovariectomy-induced osteoclastic activation.

After the second drug treatment period, rats were sacrificed, and BMD and BMC of the tibia and femur were measured. As shown in Table 9, post-treatment of RD effectively reversed the bone loss effect of ovariectomy. With regard to the preservation of the bone volume, RD was more effective than alendronate.

TABLE 9

| Post-treatment of RD inhibits OVX-induced bone loss in rats | | | | |
|---|---|---|---|---|
| | Sham | OVX | RD | Alendronate |
| Bone length, mm | | | | |
| Tibia | 4.04 ± 0.03 | 4.05 ± 0.03 | 4.01 ± 0.03 | 4.02 ± 0.05 |
| Femur | 3.69 ± 0.03 | 3.68 ± 0.02 | 3.71 ± 0.06 | 3.68 ± 0.05 |
| Wet weight, mg | | | | |
| Tibia | 766.6 ± 19.9 | 661 ± 18.2* | 749 ± 20.1§ | 712.1 ± 10.1§ |
| Femur | 1002.6 ± 17.4 | 861 ± 10.7* | 985.3 ± 9.8§ | 912.4 ± 10.9§ |
| BMD, g/cm$^2$ | | | | |
| Tibia | 0.114 ± 0.003 | 0.101 ± 0.002* | 0.113 ± 0.009§ | 0.108 ± 0.002§ |
| Femur | 0.137 ± 0.002 | 0.121 ± 0.002* | 0.135 ± 0.004§ | 0.131 ± 0.003§ |
| BMC, g | | | | |
| Tibia | 0.315 ± 0.013 | 0.272 ± 0.006* | 0.299 ± 0.011§ | 0.289 ± 0.009§ |
| Femur | 0.442 ± 0.012 | 0.391 ± 0.008* | 0.441 ± 0.018§ | 0.401 ± 0.017§ |
| Bone volume, % | 18.1 ± 1.2 | 7.9 ± 2.1* | 16.3 ± 2.7§ | 12.1 ± 1.3§ |

BMD is the abbreviation of bone mineral density; BMC is the abbreviation of bone mineral content.
Values are means ± SD.
*Compared with Sham-group, P < 0.05
§Compared with OVX-group OVX, P < 0.05
RD: I.M. injection (1.5/mg/kg/alternate day)
Alendronate: p.o. (1.5 mg/kg/alternate day)
n = 5 for each group

EXAMPLE 15

Inhibition of Chondrocyte Damage by RD in Osteoarthritis Animals

Figure 4:
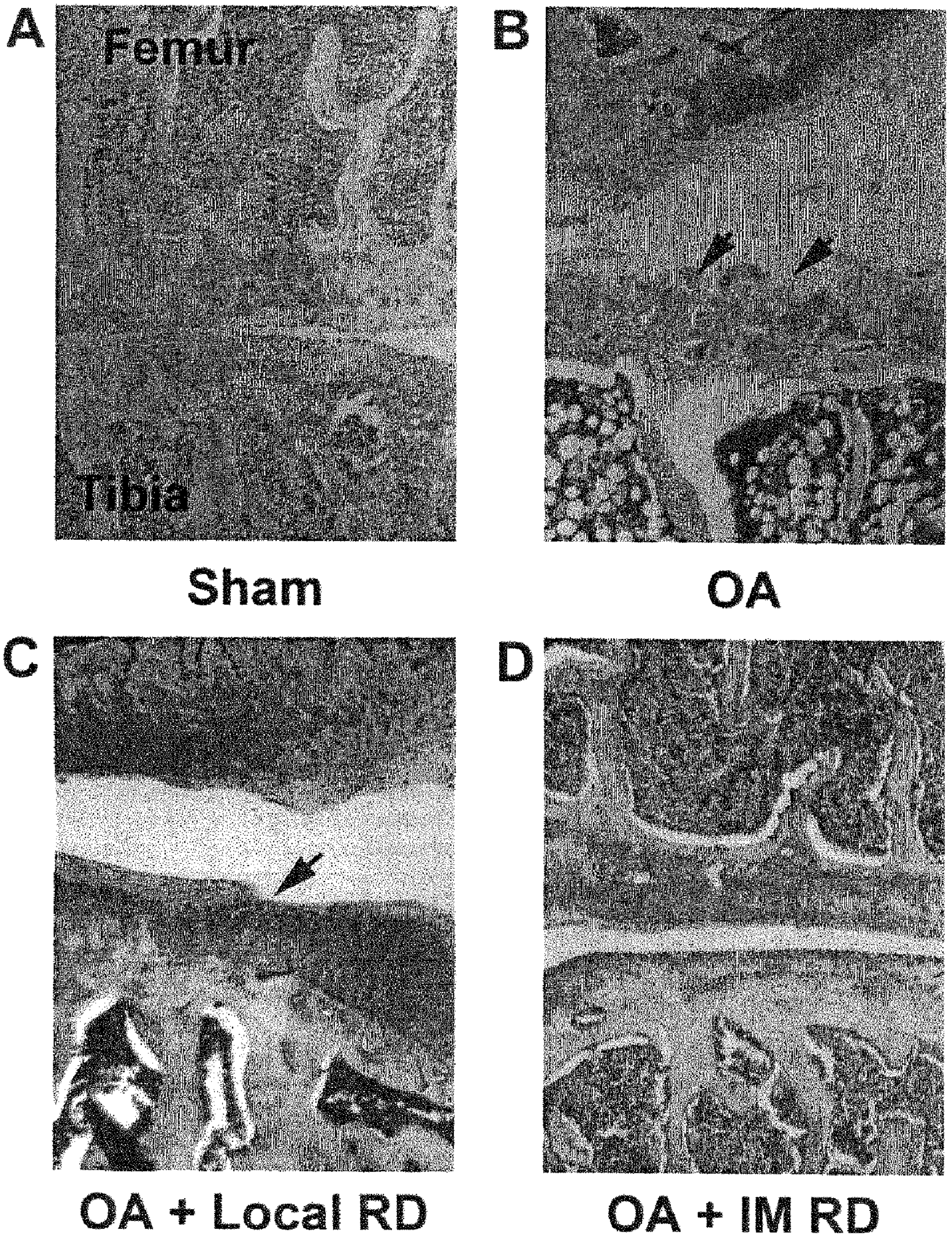
FIGS. 4A-4D are photographs of safranin-O and haematoxylin stained knee joint showing inhibition of chondrocyte layer destruction in arthritic rats treated with RD protein. Arrows indicate the chondrocyte layer.

An osteoarthritis animal model was obtained by surgery only on the right knees of male Sprague-Dawley rats. Surgery involved anterior cruciate ligation transaction and partial medial meniscectomy. After the surgery, RD protein was administered via intramuscular route (1.5 mg/kg/alternate day) or local joint injection (once/week) until the last day when the rats were sacrificed 6 weeks after the surgery. Each joint was embedded in paraffin wax, sectioned and stained with 0.1% safranin-O and haematoxylin. As shown in FIG. 4B, the chondrocyte layer in the right knee joint was damaged by arthritis and RD in either intramuscular injection (FIG. 4D) or local application (FIG. 4C) inhibited the chondrocyte layer destruction.

EXAMPLE 16

Inhibition of Blood Cytokine Elevation by RD in Osteoarthritis Rat

Figure 5:
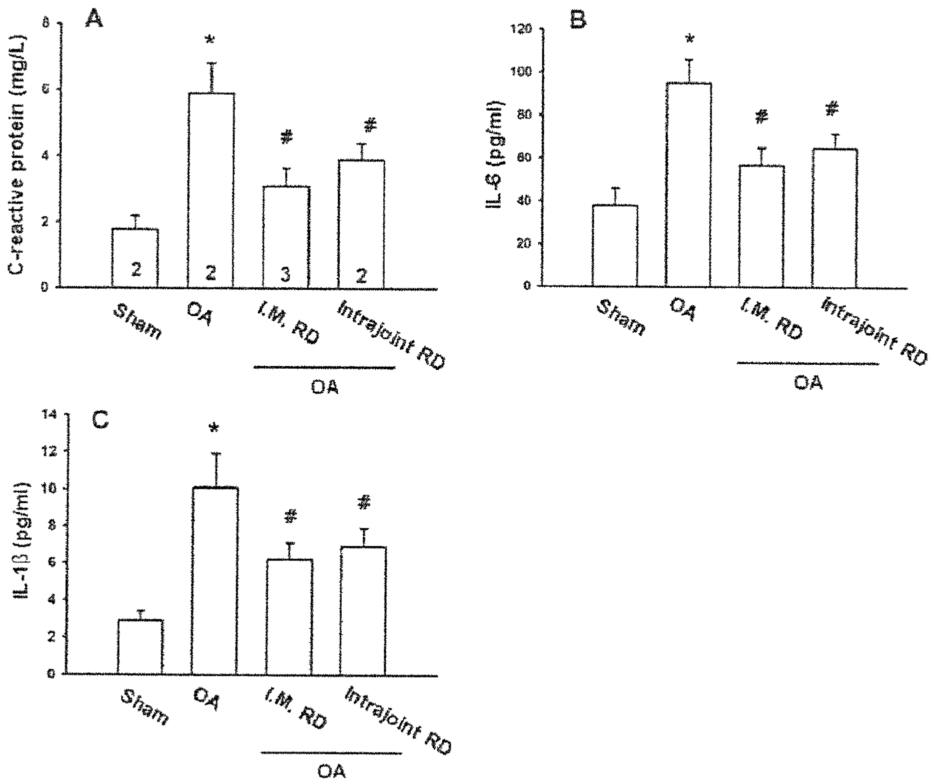
FIGS. 5A-5C are graphs showing inhibition of blood cytokine elevation in osteoarthritis rat treated with RD protein.

Osteoarthritic rats were generated by surgery as described above. Six weeks after surgery, serum was obtained to measure the blood level of cytokines. As shown in FIGS. 5A-5C, the serum levels of cytokines, such as c-reactive protein, IL-1β and IL-6, increased in osteoarthritic rats, and RD administration markedly inhibited the osteoarthritis-induced elevation of cytokines.

EXAMPLE 17

Inhibition of Blood Cytokine Elevation by RD in Osteoarthritis Mice

Figure 6:
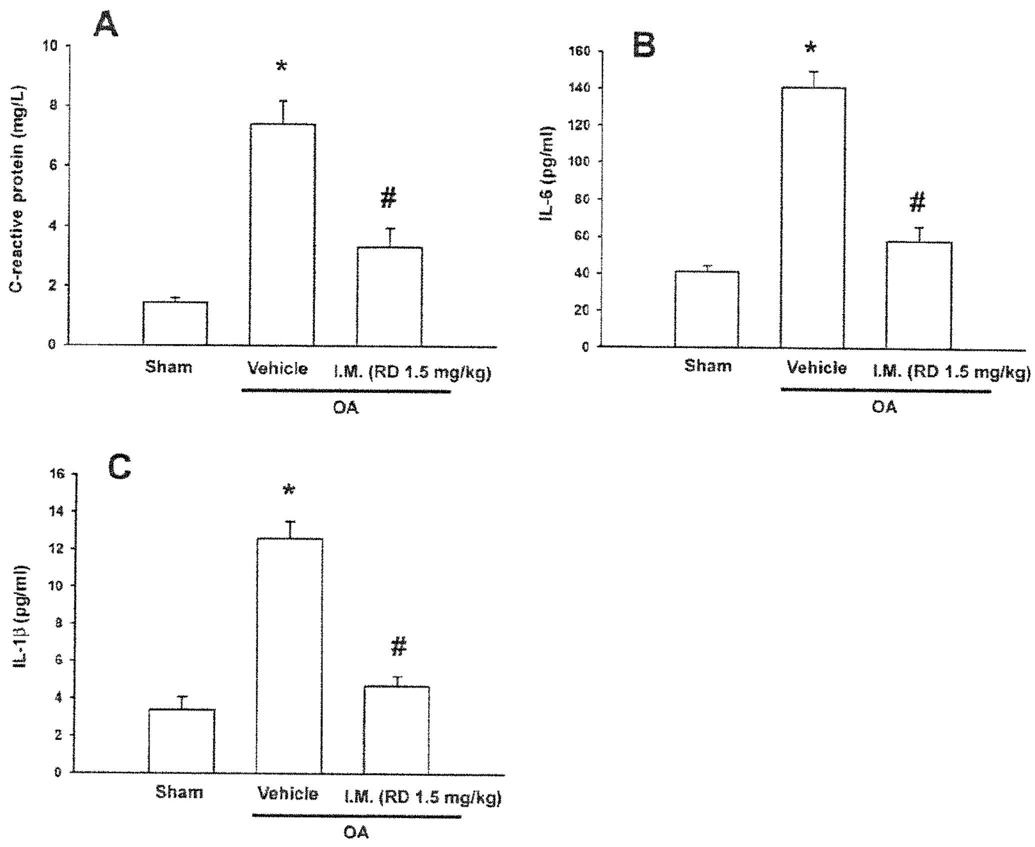
FIGS. 6A-6C are graphs showing inhibition of blood cytokine elevation in osteoarthritis mice treated with RD protein.

Osteoarthritic mice were generated by surgery as described above. Six weeks after the surgery, the serum was obtained to measure the level of cytokines. As shown in FIG. 6A-6C, the serum levels of cytokines, such as c-reactive protein, IL-1□ and IL-6, increased in osteoarthritic mice, and RD administration markedly inhibited the osteoarthritis-induced elevation of cytokines.

EXAMPLE 18

Intra-Tibia Injection of Prostate or Breast Cancer Cells in Mice

Severe Combined Immune Deficiency (SCID) male mice or BALB/c-nu/nu male mice weighing 20-22 g (6 weeks old) bred in an animal isolator (IVC racks) under a specific pathogen-free (SPF) condition at 22±2° C. were used. Human prostate adenocarcinoma PC-3 cells or human breast cancer MDA-MB-231 cells (1×10$^6$ cells in 15 ml sterile PBS) were injected into the bone marrow of both the left and right tibia of the SCID mice or nude mice on day-1, respectively. On day-11, the animals were randomly assigned into three groups and the administration of test substances was initiated. RD (1.5 mg/kg) was administered by intramuscular (IM) injection and alendronate (1.5 mg/kg) was given by subcutaneous (SC) injection, once daily for a total of 15 doses (5 days on, 2 days off for 3 weeks). The body weight and tumor growth condition were observed and recorded every week during the experimental period. After one month, the mice were sacrificed and the weight of the hind legs was measured. The weight of the control leg was subtracted to reflect the relative tumor weight. In addition, blood samples were collected at the end of the experiment for the blood count of red blood cells (RBC), white blood cell (WBC) and platelet, and for the measurement of the C-terminal telopeptides of type I collagen (CTX) and serum calcium concentration.

In order to determine bone osteolysis, radiographs were taken by a soft X-ray generating unit (Young-kid Enterprise Co., Ltd., Taipei, Taiwan). Animals were deeply anesthetized with trichloroacetaldehyde monohydrate, laid down in a prone position on a Kodak Scientific Imaging film (13×18 cm), and X-ray exposure was performed at 45 kV for 5 seconds. The degree of osteolysis was measured using image analysis software (Image-pro plus 3.0).

EXAMPLE 19

Inhibition of Tumor Growth in Bone and Hypercalcemia

Figure 7:
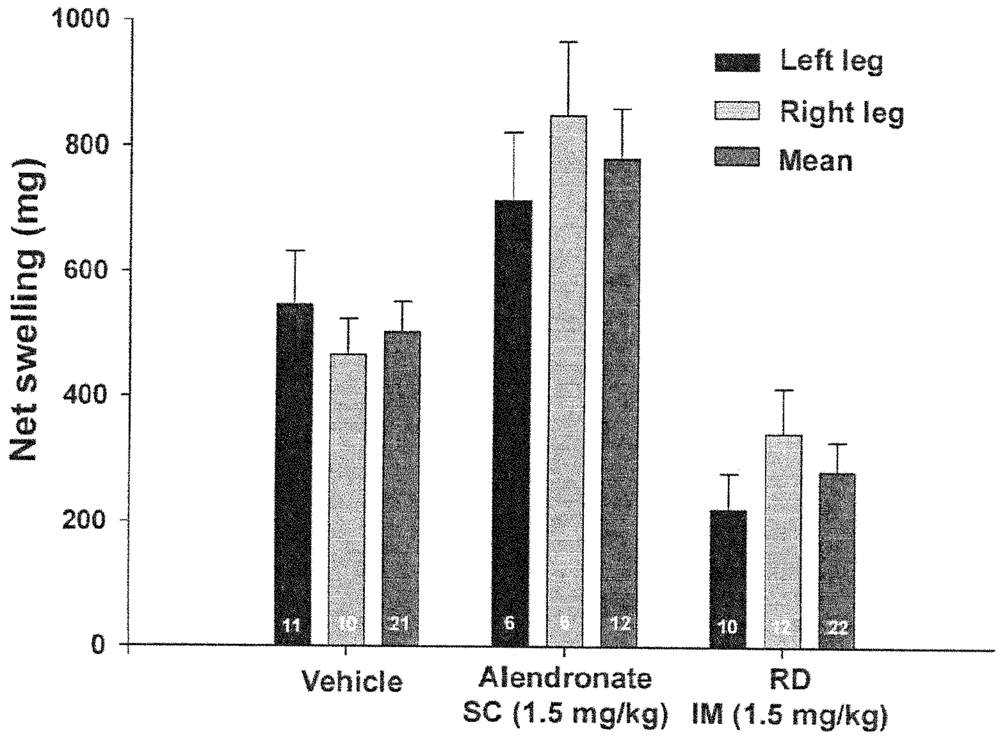
FIG. 7 is a graph showing inhibition of PC-3 bone tumor growth in SCID mice treated with RD protein, but not with alendronate.

Tumor cell growth in bone is related to the bone resorption activity. The effect of RD protein on the tumor growth of prostate cancer cells in bone was thus examined. PC-3 cells ($1\times10^6$) were locally injected into the bone marrow cavities of both tibia in SCID mice. RD or alendronate was administered 10 days after the implantation of tumor cells. RD at 1.5 mg/kg was given by the intramuscular (IM) route while alendronate was given at 1.5 mg/kg by the subcutaneous (SC) injection, once daily for a total of 15 doses (5 days on, 2 days off for 3 weeks). The swelling of hind legs was calculated to reflect the tumor growth on day 33. The body weight was measured throughout the experimental period. The results indicated that RD at 1.5 mg/kg caused a significant inhibition in tumor cell-induced swelling in hind legs on day-33 (43.8±4.1%, n=21-22) (FIG. 7). However, the subcutaneous administration of alendronate at 1.5 mg/kg did not inhibit the tumor growth in legs (FIG. 7).

Figure 8:
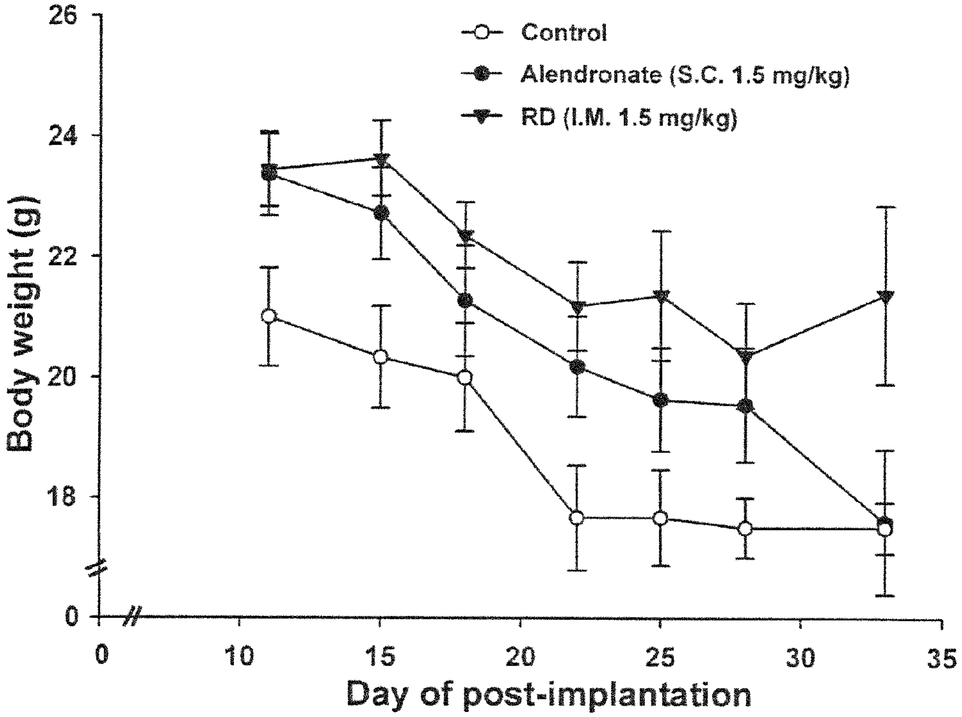
FIG. 8 is a graph showing inhibition of tumor-induced decrease in body weight in SCID mice treated with RD protein.

FIG. 8 shows the effect of RD on the decrease in body weight in response to the tumor growth in SCID mice. Untreated control mice showed a decrease in body weight at the end of the experiment. Treatment with RD prevented the loss of body weight caused by the tumor growth. Alendronate was used as a positive control.

Figure 9:
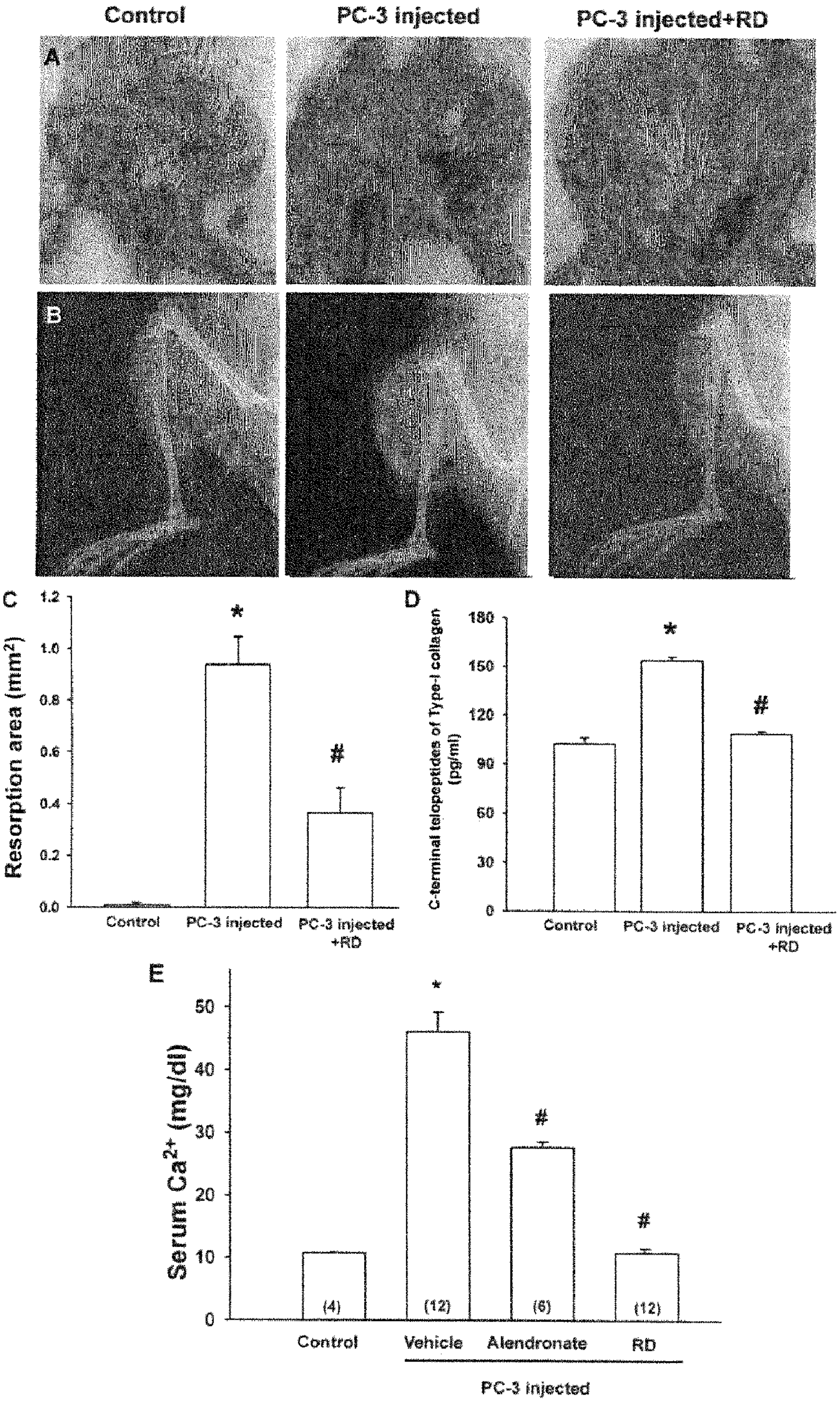
FIG. 9A are photographs showing a visible spherical tumor growth in the proximal tibia of each leg after the intratibial injection of PC-3 cells (shown by arrows in the middle panel) and an inhibition of the bone tumor growth in SCID mice treated with RD protein.
FIG. 9B are radiographs of tibia bones showing inhibition of PC-3 tumor cells-induced osteolytic bone lesion in SCID mice treated with RD protein.
FIG. 9C is a graph of the quantitation of the data in FIG. 9B showing inhibition of PC-3 tumor-induced osteolysis in SCID mice treated with RD protein.
FIG. 9D is a graph showing inhibition of PC-3 tumor-induced increase in C-terminal telopeptides of type-I collagen in SCID mice treated with RD protein.
FIG. 9E is a graph showing inhibition of PC-3 tumor-induced increase in the serum calcium concentration in SCID mice treated with RD protein or alendronate.

FIG. 9 shows the inhibition of tumor growth and osteolytic bone lesion by RD in SCID mice. In order to determine bone osteolysis, radiographs were taken by a soft X-ray generating unit. In FIG. 9A, photographs were taken 33 days after the intratibial injection of PC-3 cells. A visible spherical tumor grew up from the proximal tibia. Treatment with RD (I.M., 1.5 mg/kg/alternate day) inhibited tumor growth. In FIG. 9B, radiographs taken on day-33 revealed that osteolytic lesions appeared in the cancer cell-injected tibia and treatment of RD inhibited osteolysis. FIG. 9C shows the quantitation of the data. FIG. 9D shows that RD inhibited a tumor-induced increase in C-terminal telopeptides of type-collagen (a marker for the osteoclast activity) using an ELISA method. FIG. 9E demonstrates that RD and alendronate (1.5 mg/kg/alternate day) also inhibited a tumor-induced increase in the serum calcium concentration (i.e., hypercalcemia). *: $p<0.05$, as compared with control. #: $p<0.05$, as compared with the PC-3-injected group.

Figure 10:
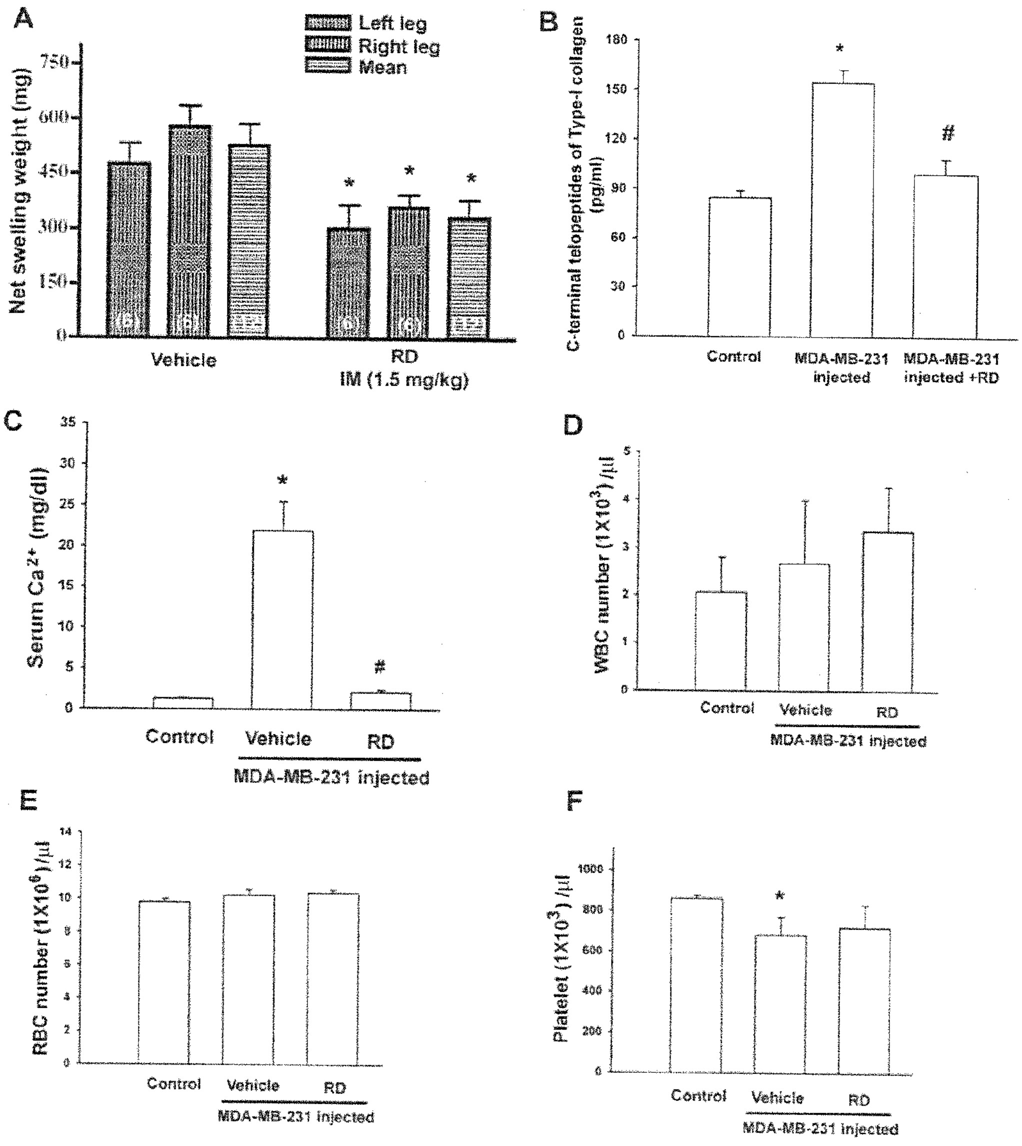
FIG. 10A is a graph showing inhibition of MDA-MB-231 bone tumor growth in nude mice treated with RD protein.
FIG. 10B is a graph showing inhibition of MDA-MB-231 bone tumor-induced increase in C-terminal telopeptides of type-I collagen in nude mice treated with RD protein.
FIG. 10C is a graph showing inhibition of MDA-MB-231 bone tumor-induced hypercalcemia in nude mice treated with RD protein.
FIG. 10D is a graph showing no change in white blood cell counts in nude mice injected with MDA-MB-231 cells and treated with RD protein.
FIG. 10E is a graph showing no change in red blood cell counts in nude mice injected with MDA-MB-231 cells and treated with RD protein.
FIG. 10F is a graph showing no change in the platelet counts in nude mice injected with MDA-MB-231 cells and treated with RD protein.

Breast cancer has a strong predilection for metastasizing to bone. FIG. 10 shows inhibition of tumor growth by RD in nude mice. Human breast cancer cells MDA-MB-231 ($1\times10^6$) were locally injected into the bone marrow cavities of both tibia in nude mice. RD (I.M., 1 mg/kg/day) was administered 10 days after the implantation of tumor cells for a total of 14 days. Treatment with RD (IM, 1.5 mg/kg/day) for 2 weeks inhibited MDA-MB-231-induced increase in tumor growth in bone (FIG. 10A). Furthermore, RD also prevented the tumor-induced increase in osteoclast activity (FIG. 10B) and hypercalcemia (FIG. 10C), but did not affect the blood counts of RBC, WBC and platelet (FIGS. 10D-10F). *: $p<0.05$, as compared with the control. #: $p<0.05$, as compared with the MDA-MB-231-injected group.

EXAMPLE 20

Pegylation of RD Protein

A pegylated product or a conjugation with albumin can prolong the duration and decrease the antigenicity of a protein drug. In order to minimize the antigenicity and prolong the duration of RD protein, pegylated RD protein was prepared as follows: RD protein (4 mg) in 20 mM $NaCNBH_3$ at pH 5 was reacted with 5 mM PEGk5-propionaldehyde (O-Methyl-O'-[2-(6-oxocaproylamino)ethyl]polyethylene glycol 5,000) (Sigma) at 4° C. for 12 h. The pegylated RD protein was purified by reverse phase C18 HPLC. The final yield of pegylated RD protein after purification was greater than 60%.

As shown in Table 6, pegylated-RD inhibited the differentiation of osteoclasts. In addition, treatment with pegylated-RD (I.M., 1.5 mg/kg, once/week) for 2 weeks inhibited the loss of BMD and BMC (Table 6). These data indicate that pegylated-RD did not lose its activity in vivo.

EXAMPLE 21

MATRIGEL™ Plug Antiangiogenesis Assays

It has been reported that integrin αvβ3 is related to angiogenesis. Whether RD protein can inhibit angiogenesis was investigated using MATRIGEL™ plug angiogenesis assays as described previously with minor modifications. See, Passaniti A, Taylor R M, Pili R, Guo Y, Long P V, Haney J A, Pauly R R, Grant D S, Martin G R (1992) *A simple, quantitative method for assessing angiogenesis and antiangiogenic agents using reconstituted basement membrane, heparin, and fibroblast growth factor*, Lab Invest 67: 519-528.

Figure 11:
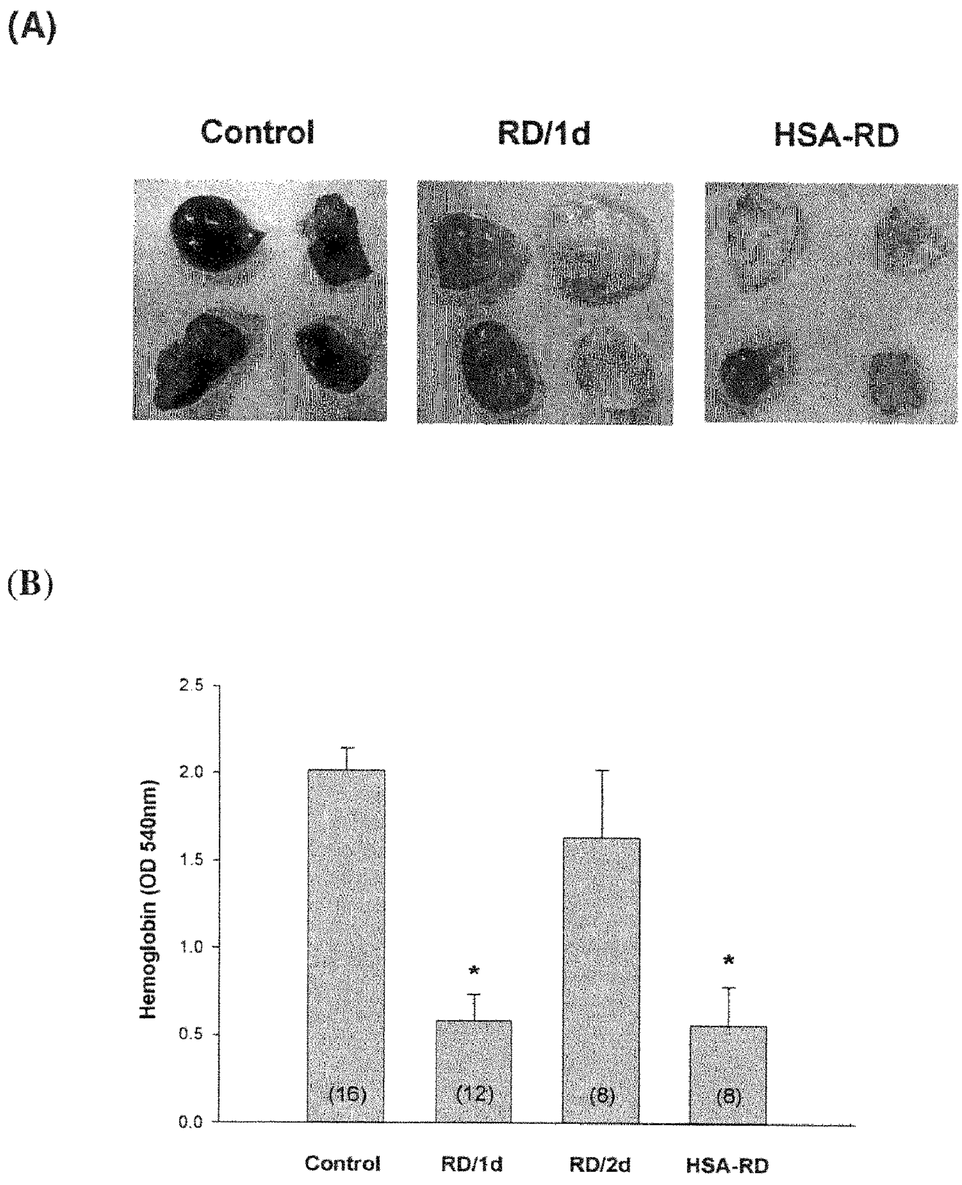
FIG. 11A are photographs showing reduced blood vessel density in MATRIGEL™ plugs from C57BL/6 mice treated with RD or RD-albumin (HSA-RD) protein in comparison with untreated control mice.
FIG. 11B is a graph showing reduced hemoglobin content in MATRIGEL™ plugs from C57BL/6 mice treated with RD (every day-RD/1d or every other day-RD/2d) or RD-albumin (HSA-RD-every other day) protein in comparison with untreated control mice.

Briefly, an aliquot (500 μl) of MATRIGEL™ (Becton Dickinson Lab.) containing 200 ng/ml VEGF was injected subcutaneously into the dorsal region of 6-8 week-old C57BL/6 mice. The MATRIGEL™ formed a plug rapidly. RD was administered intramuscularly (3 mg/kg) daily (RD/1d) or the other day (RD/2d or HSA-RD) before sacrifice. After 8 days, plugs were taken and photographed (FIG. 11A). Neovessels were quantified by measuring the hemoglobin of the plugs as an indication of blood vessel formation with the Drabkin method and Drabkin reagent kit 525 (Sigma) (FIG. 11B). As shown in FIGS. 11A and 11B, RD protein was effective in inhibiting angiogenesis using MATRIGEL™ plug assays. *: $P<0.05$ versus control group.

EXAMPLE 22

Radioligand-Binding Assay: Specificity of RD-Related Proteins

To determine whether RD and its derivative PGP bind to other receptors besides αvβ3 integrin, RD and its derivative PGP were used to analyze the target specificity toward receptors whose ligands are proteins (assayed by MDS Pharma services, Taipei, Taiwan).

As shown in Table 10, RD and PGP did not affect the binding activity of calcitonin, endothelin ETA, endothelin ETB, insulin, leptin, sodium channel, transforming growth factor-β (TGF-β), tumor necrosis factor (TNF) and vascular endothelial growth factor (VEGF) to their respective receptors. This indicates that RD-related proteins exert selective binding activity toward target protein αvβ3 in viva

TABLE 10

The binding assay of RD and PGP protein

| | Inhibition | |
|---|---|---|
| Target | RD | PGP |
| Calcitonin | 4% | −6% |
| Endothelin $ET_A$ | 26% | −3% |
| Endothelin $ET_B$ | 10% | −7% |
| Insulin | −6% | −8% |
| Leptin | 1% | 2% |
| Sodium Channel (Site 2) | 2% | −14% |
| TGF-β | 14% | −10% |

TABLE 10-continued

| The binding assay of RD and PGP protein | | |
|---|---|---|
| | Inhibition | |
| Target | RD | PGP |
| TNF | 4% | 20% |
| VEGF | −14% | 19% |

TGF-β: transforming growth factor-β
TNF: tumor necrosis factor
VEGF: vascular endothelial growth factor

EXAMPLE 23

Inhibition of Angiogenesis by RD in a Mouse Model of Retinopathy of Prematurity

An animal model for retinopathy of prematurity in mice was generated by using hypoxic-induced angiogenesis as described in Wilkinson-Berka et al. [28]. Briefly, seven-day-old pups and their mother were housed in sealed chambers containing 75% $O_2$ and air. Mice remained in the chamber for five days (hyperoxic period, P7 to P12) and were then housed in room air for a further seven days (hypoxic-induced angiogenic period, postnatal 12 days to postnatal 19 days, or P12 to P19). RD (2 μg) was administered via an intravitreous route on day-12 and the mice were sacrificed on day-19.

Three sections from one of the eyes of each animal were made, deparaffinized, and stained with hematxylin and eosin. Blood vessel profiles (BVPs) were counted in the inner retina, and included vessels adherent to the inner limiting membrane. Counting was performed on a photomicroscope (Leica) at a magnification of 100×.

Figure 12:
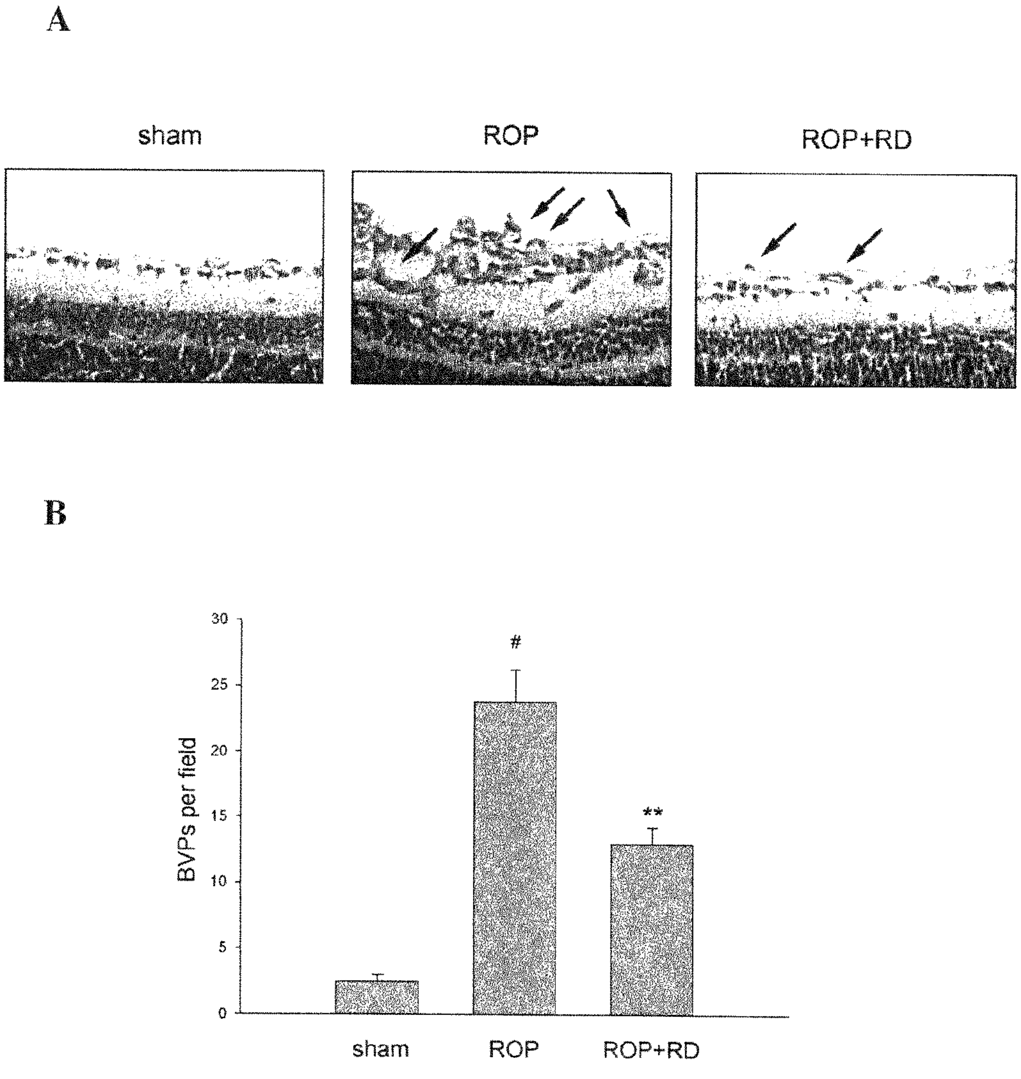
FIG. 12A are photographs showing angiogenesis in a mouse model of retinopathy of prematurity (ROP), and reduced angiogenesis in a ROP mouse treated with RD protein (ROP+RD). Arrows indicate blood vessel profiles (BVPs).
FIG. 12B is a graph showing reduced BVPs in a mouse model of retinopathy of prematurity (ROP) treated with RD protein.

As shown in FIG. 12A, RD protein inhibited angiogenesis in a mouse model of retinopathy of prematurity (ROP). FIG. 12B shows reduced BVPs in a mouse model of retinopathy of prematurity (ROP) treated with RD protein. Angiogenesis was quantitated by counting blood vessel profiles (BVPs) in the inner retina and extending into the vitreous cavity from three hematoxylin-and-eosin-stained sections. The ROP group treated with RD (2 μg) (i.e., ROP RD) reduced about 46% of angiogenesis compared to the ROP group treated with vehicle (ROP). (n=7 for each ROP group; n=2 for sham group.) Data are presented as Mean±SE. #: $p<0.01$, as compared to the sham group. **: $p<0.001$, as compared to the ROP group.

EXAMPLE 24

Inhibition of Ovariectomy-Induced Osteoporosis by Albumin-Conjugated RD

Figure 13:
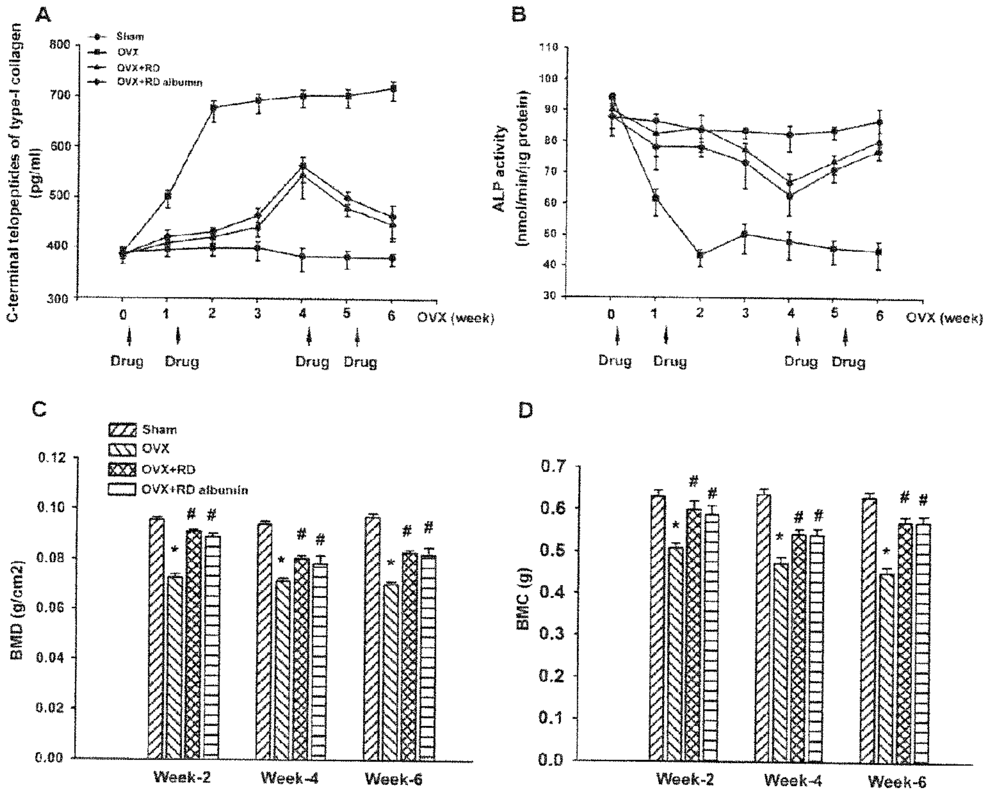
FIG. 13A is a graph showing inhibition of ovariectomy-induced osteoclast activation in mice treated with RD or RD-albumin protein.
FIG. 13B is a graph showing inhibition of ovariectomy-induced alkaline phosphatase (ALP) inactivation in mice treated with RD or RD-albumin protein.
FIG. 13C is a graph showing inhibition of ovariectomy-induced decrease in BMD.
FIG. 13D is a graph showing inhibition of ovariectomy-induced decrease in BMC.

The effect of albumin-conjugated RD on osteoporosis was examined in ovariectomized female mice. Human serum albumin-conjugated RD (i.e., RD-albumin) was administered as indicated by arrows shown in FIGS. 13A and 13B. The data for RD was incorporated into FIGS. 13A-13D for comparison. Serum levels of the C-terminal peptide of type I collagen and alkaline phosphatase (ALP) were measured as indicators of osteoclast and osteoblast activity, respectively. The BMD and BMC were also measured every 2 weeks, as shown in FIGS. 13C and 13D. Treatment of RD-albumin (15 mg/kg/week) markedly reduced osteoclast, but increased ALP, activities in a reversible manner.

EXAMPLE 25

Inhibition of Rheumatoid Arthritis by RD

Rheumatoid arthritis is a chronic systemic inflammatory disorder of unknown etiology characterized by invasive synovial hyperplasia that leads to progressive joint destruction. Osteoclasts, derived from the monocyte/macrophage lineage, play a crucial role in subchondral bone destructions in rheumatoid arthritis. Radiographic studies have shown that in rheumatoid arthritis, osteopenia of the subchondral bone and bone erosion begin at an early stage of the disease, and are gradually exacerbated. See, van der Heijde D M, van Leeuwen M A, van Riel P L, van de Putte L B, *Radiographic progression on radiographs of hands and feet during the first* 3 *years of rheumatoid arthritis measured according to sharp's method* (*van der Heijde modification*), J Rheumatol 1995; 22:1792-1796. Bone-resorbing osteoclasts are observed at the erosive synovium/bone interface. See, Sakae Tanaka (2007), *Signaling axis in osteoclast biology and therapeutic targeting in the RANKL/RANK/OPG System*, Am. J. Nephrol, 27:466-478. A recent review discusses the role of osteoclasts in rheumatoid arthritis. Sato K, Takayanagi H., (2006) *Osteoclats, rheumatoid arthritis and osteoimmunology*, Curr Opin Rheumatol 18: 419-426. Therefore, RD-related proteins, which markedly inhibit osteoclast functions, may be useful for treatment of rheumatoid arthritis.

Lewis rats are given intradermal/subcutaneous (SC) injections of bovine type II collagen (2 mg/ml in Freund's incomplete adjuvant). As rats develop the rheumatoid disease, they are randomly divided into several study groups. Treatment is initiated on the first day when the clinical signs of arthritis are clearly visible, as evidenced, for example, by ankle joint swelling. After measuring the paw volume, rats are sacrificed, and ankle and knee joints are collected for the examination of histopathological change.

FIGS. 14A-D show amino acid sequences of Rho and its variants, SEQ ID NOs: 1, and 57-69, respectively. FIGS. 15A-C show nucleotide sequences of rhodostomin variants, SEQ ID NOs: 43-56. FIGS. 16A-H show amino acid and nucleotide sequences of disintegrin variants, SEQ ID NOs: 78-135.

EXAMPLE 26

Pegylation of ARLDDL Protein

A pegylated product or a conjugation with albumin can prolong the duration and decrease the antigenicity of a protein drug. In order to minimize the antigenicity and prolong the duration of ARLDDL protein, pegylated ARLDDL (PEG-ARLDDL) protein was prepared substantially as pegylated-RD protein was prepared as described in Example 20.

Briefly, ARLDDL protein (4 mg) in 20 mM $NaCNBH_3$ at pH 5 was reacted with 5 mM PEGk5-propionaldehyde (O-Methyl-O'-[2-(6-oxocaproylamino)ethyl]polyethylene glycol 5,000) (Sigma) at 4° C. for 12 h. PEG-ARLDDL protein was purified by reverse phase $C^{18}$ HPLC. The final yield of PEG-ARLDDL protein after purification was greater than 60%.

EXAMPLE 27

MATRIGEL™ Plug Anti-Angiogenesis Assays

To investigate whether PEG-ARLDDL can inhibit angiogenesis, MATRIGEL™ plug angiogenesis assays were used as described in parent US Patent Application Publication No. 2008-0188413 A1. Briefly, 0.3 ml of MATRIGEL™ (Becton Dickinson Lab.) containing 150 ng recombinant human VEGF and 30 IU heparin was injected subcutaneously into the dorsal region of 6-8 week-old C57BL/6 mice. The MATRIGEL™ formed a plug rapidly. On day 2, PEG-ARLDDL at 0.5 mg/kg or at 5 mg/kg was intravenously administered via tail. After seven days, the skin of mouse was pulled back and the Matrigel™ plug was excised from it. FIG. 17A depicts photographs of the plugs.

Neovessels were quantified by measuring the hemoglobin of the plugs as an indication of blood vessel formation with the Drabkin method and Drabkin reagent kit 525 (Sigma) (FIG. 17B).

FIGS. 17A (photographs) and 17B (a bar chart) show that PEG-ARLDDL was effective in inhibiting angiogenesis using MATRIGEL™ plug assays because it significantly reduced the hemoglobin content of the Matrigel™ plug as compared with control group. *: $P<0.05$ versus control

EXAMPLE 28

Dose-Dependent Inhibition of PC-3 Tumor Growth by PEG-ARLDDL

The human PC-3 (prostate cancer) cells were implanted in Non-Obese Diabetic Severe Combined Immune Deficiency (NOD-SCID) mice as follows. 4 to 5 week-old male NOD-SCID mice were purchased from Laboratory Animal Center of the National Taiwan University. All mice were kept under standard temperature, humidity, and timed lighting conditions and were provided mouse chow and water. All animal experiments were conducted in accordance with the Guidelines for Animal Research of Agriculture Council, ROC and approved by the Ethical Committee for Animal Research of the National Taiwan University.

PC-3 tumor cells at $10^7$ were injected subcutaneously in the flank of the mice in serum-free medium.

One week after PC-3 cells injection, mice were injected intravenously with saline (control, n=4); PEG-ARLDDL (2 mg/kg/week, n=2) and PEG-ARLDDL (10 mg/kg/week, n=4). Tumor volume was measured weekly. After the mice were sacrificed on day 39, tumors were isolated and weighted.

Tumor Volume was calculated using the following equation:

$$0.52\times(\text{width(cm)}^2\times\text{length}).$$

Tumor weight was estimated based on the assumption that 1 mg is equivalent to 1 $mm^3$ of tumor volume.

FIG. 18 depicts photographs of tumors excised from the control mice (left photograph); mice treated with 2 mg/kg/week PEG-ARLDDL (middle photograph); and mice treated with 10 mg/kg/week PEG-ARLDDL (right photograph).

FIG. 19 is a bar chart that shows that PEG-ARLDDL significantly inhibited tumor growth in the mice treated with PEG-ARLDDL in a dose-dependent manner as measured by tumor weight.

In another experiment, everything was done in the same manner as described above, except that one week after PC-3 cells injection, mice were injected intravenously with saline (control, n=4); PEG-ARLDDL (10 mg/kg/week, n=2) (once every two weeks) and PEG-ARLDDL (10 mg/kg/week, n=4) (once a week). Tumor volume was measured weekly.

FIG. 20 is a graph that shows that PEG-ARLDDL significantly inhibited growth of tumors in the mice treated with this protein as measured by tumor volume. 10 mg/kg/week PEG-ARLDDL administered once a week had a stronger inhibitory effect than 10 mg/kg/week PEG-ARLDDL administered once every two weeks.

FIG. 21 depicts photographs of tumors excised from the control mice (left photograph); mice treated with 10 mg/kg/week PEG-ARLDDL once every two weeks (middle photograph); and mice treated with 10 mg/kg/week PEG-ARLDDL once a week (right photograph). The results confirm that tumor volume was the smallest in the mice treated with 10 mg/kg/week PEG-ARLDDL once a week.

Figure 22:
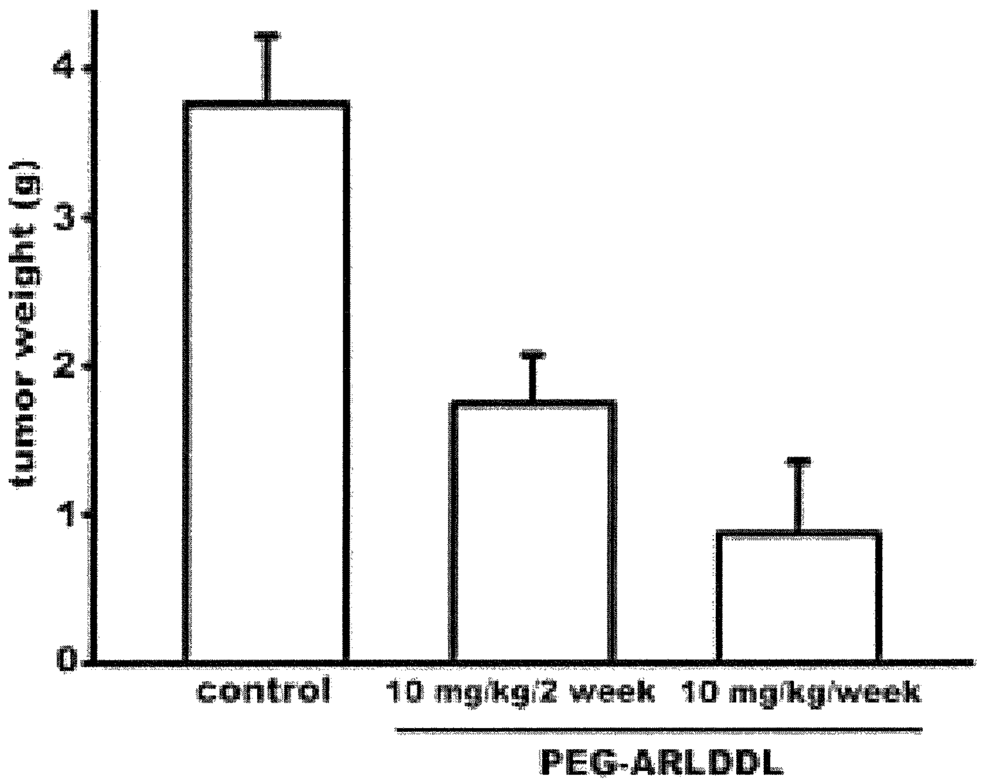
FIG. 22 a bar chart that shows that PEG-ARLDDL administered once a week had a stronger inhibitory effect on tumor growth as compared to PEG-ARLDDL administered once every two weeks.

FIG. 22 is a bar chart that shows that PEG-ARLDDL significantly inhibited growth of tumors in the mice treated with this protein as measured by tumor weight. After mice were sacrificed on day 39, tumors were isolated and weighted. 10 mg/kg/week PEG-ARLDDL administered once a week had a stronger inhibitory effect than 10 mg/kg/week PEG-ARLDDL administered once every two weeks.

EXAMPLE 29

Enhancement of the Cytotoxic Activity of Daunomycin by PEG-ARLDDL

Human PC-3 (prostate cancer) cells were implanted in NOD-SCID mice as follows.

PC-3 tumor cells at $10^7$ were injected subcutaneously in the flank of the mice in serum-free medium.

One week after PC-3 cells injection, mice were injected intravenously with saline (control, n=4); daunomycin (0.05 mg/kg/week, once a week; n=3); PEG-ARLDDL alone (2 mg/kg/week, n=2) and a combination of daunomycin (0.05 mg/kg/week) and PEG-ARLDDL (2 mg/kg/week, n=2). Tumor volume was measured weekly. After the mice were sacrificed on Day 39, tumors were isolated and weighted.

FIG. 23 is graph that shows that daunomycin significantly enhanced the cytotoxic activity of PEG-ARLDDL. The tumors were smallest in the mice treated with the combinatorial treatment.

FIG. 24 depicts photographs of tumors excised from the control mice (left photograph); mice treated with daunomycin alone (second from the left photograph); mice treated with PEG-ARLDDL alone (second from the right photograph); and mice treated with a combination of daunomycin and PEG-ARLDDL (right photograph). The photographs demonstrate that the tumor was the smallest in mice treated with a combination of daunomycin and PEG-ARLDDL.

FIG. 25 a bar chart that further shows that a combination of daunomycin and PEG-ARLDDL significantly inhibited growth of tumors in the mice, as compared with mice treated with only daunomycin or only PEG-ARLDDL, as measured by tumor weight. There is a synergistic effect from combining the two treatments.

EXAMPLE 30

Inhibition of Osteopontin-Induced Glioma Invasion in Hypoxia by PEG-ARLDDL

The invasion assay was performed using Transwell (Costar, N.Y., USA; pore size 8 μm) in 24-well dishes. Filters were precoated with 30 μl MATRIGEL™ containing 100 μg/ml hyaluronic acid.

Approximately $5\times10^4$ U87 human glioma cells in MEM containing 0.5% FBS were placed in the upper chamber of the Transwell and 600 μl of the same medium containing 10% FBS was placed in the lower chamber.

PEG-ARLDDL at 10 nM, at 100 nM and at 1 μM was added to the cells in the upper chamber. The plates were incubated for 15 hours at 37 degrees C. in hypoxic condition (94% $N_2$, 5% $CO_2$ and 1% $O_2$). Non-migratory cells on the upper surface of the filters were removed by wiping with a cotton swab. Migrated cells that penetrated through pores and migrated to the underside of the filters were stained with 0.05% crystal violet solution containing 20% methanol. The cell number per well was counted under microscope at 100× magnification.

FIG. 26 depicts photographs of the cells that show that osteopontin-induced glioma invasion in hypoxic conditions was markedly inhibited by PEG-ARLDDL. It is clear from the picture in the bottom right hand corner that there are significantly fewer glioma cells after treatment with PEG-ARLDDL at 100 nM than there are glioma cells after treatment with PEG-ARLDDL at 10 nM. The number of glioma cells is the highest when no PEG-ARLDDL was added.

Figure 27:
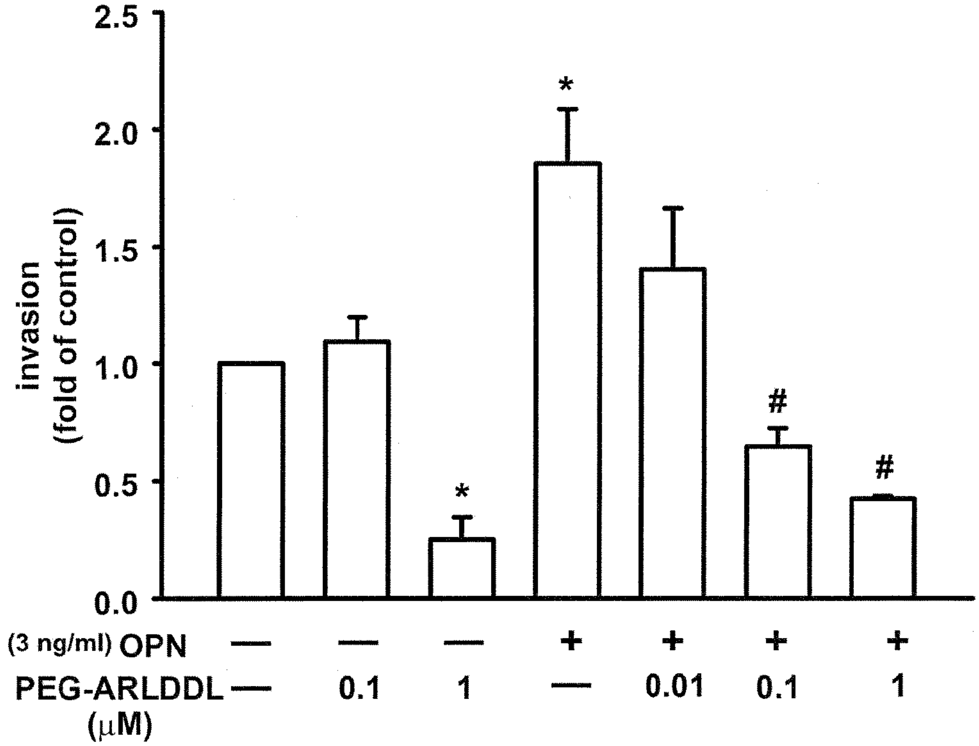
FIG. 27 is a bar chart that demonstrates that PEG-ARLDDL significantly inhibited osteopontin-induced glioma invasion in hypoxia.

FIG. 27 is a bar chart that further confirms that PEG-ARLDDL significantly inhibits glioma invasion in hypoxic condition. When additional 3 ng/ml of OPN were added, the cells which were not treated with PEG-ARLDDL had almost 2-fold increase in invasion glioma cells compared to control. The cells treated with 10 nM PEG-ARLDDL had about 1.2-fold increase in invasion glioma cells compared to control; and the cells treated with 100 nM PEG-ARLDDL had about 0.75-fold increase in invasion glioma cells compared to control. The expression of OPN can be increased in hypoxic condition (94% $N_2$, 5% $CO_2$ and 1% $O_2$). When no additional OPN was added, the cells treated with 100 nM PEG-ARLDDL had virtually no increase in invasion glioma cells compared to control. The cells treated with 1 μM PEG-ARLDDL combined with or without 3 ng/ml of OPN had over 2-fold decrease in invasion glioma cells compared to control.

EXAMPLE 31

Inhibition of U87 Human Glioma Tumor Growth by PEG-ARLDDL

Approximately $5\times10^4$ U87 human glioma cells in MEM containing 0.5% FBS were injected subcutaneously in the flank of 4 to 5 week-old male NOD-SCID mice. One week after U87 cells injection, mice were injected intravenously with saline (control; n=1) or PEG-ARLDDL (10 mg/kg, twice per week; n=2). Tumor volume was measured weekly.

Figure 28:
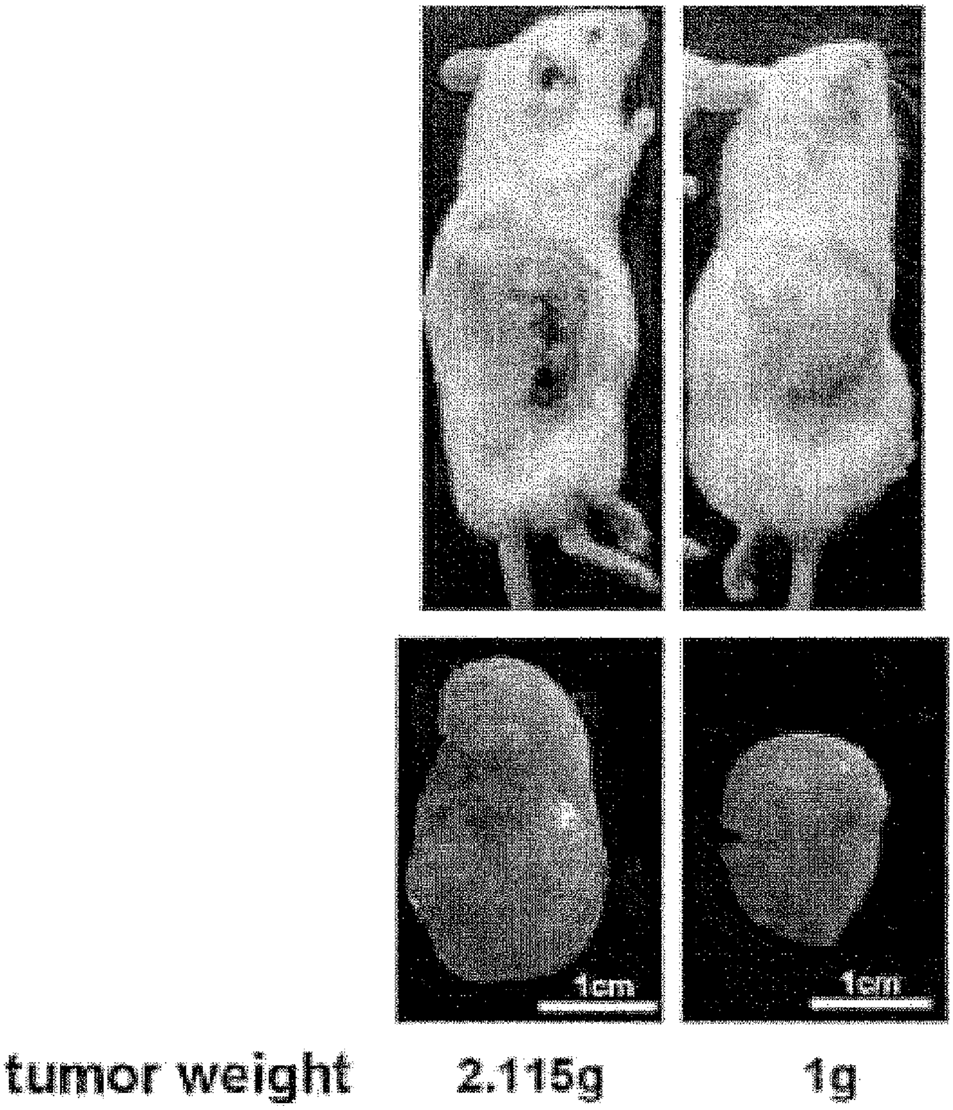
FIG. 28 shows photographs of a control mouse and its excised tumor and a mouse treated with PEG-ARLDDL and its excised tumor.
Figure 29:
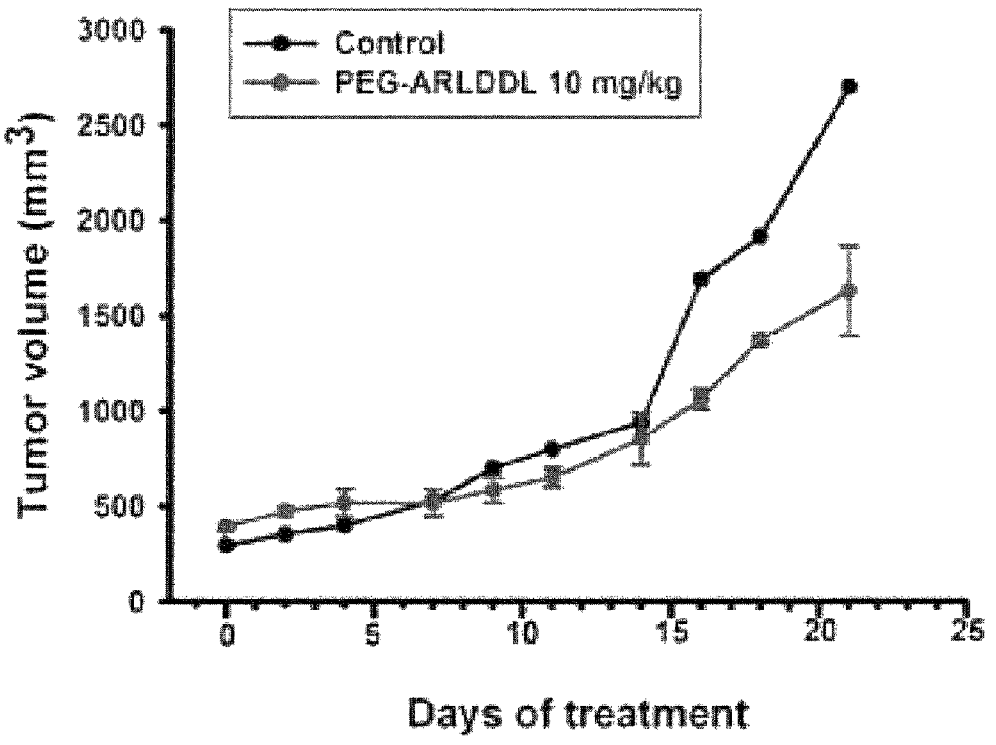
FIG. 29 is a chart that shows that PEG-ARLDDL significantly inhibited U87 human glioma tumor growth in mice.

FIG. 28 contains pictures of a control mouse and its excised tumor (pictures on the left) and pictures of the mouse injected with PEG-ARLDDL and its excised tumor (pictures on the right). The pictures clearly show that PEG-ARLDDL significantly inhibited growth of U87 human glioma tumors in the mice treated with this protein. FIG. 29 is a graph that shows that PEG-ARLDDL significantly inhibited growth of U87 human glioma tumors in the mice treated with this protein.

The foregoing description of the exemplary embodiments of the invention has been presented only for the purposes of illustration and description and is not intended to be exhaustive or to limit the invention to the precise forms disclosed. Many modifications and variations are possible in light of the above teaching.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treatment of an αvβ3 integrin-associated disease comprising:

administering to a mammal in need thereof a therapeutically effective amount of an isolated polypeptide, or a pharmaceutically acceptable salt thereof, wherein the isolated polypeptide is a variant of a disintegrin which comprises a variant of SEQ ID NO: 29 that contains an amino acid substitution at position 3 and an optional substitution at one or more positions 1, 5 and 6 of SEQ ID NO: 29.

2. The method of claim 1, wherein the disintegrin is a variant of a disintegrin chosen from rhodostomin, albolabrin, applagin, basilicin, batroxostatin, bitistatin, cereberin, cerastin, crotatroxin, durissin, elegantin, flavoridin, flavostatin, halysin, halystatin, jararacin, jarastatin, kistrin, lachesin, lutosin, molossin, salmosin, saxatilin, tergeminin, trimestatin, trimucrin, trimutase, ussuristatin, and viridin.

3. The method of claim 2, wherein the disintegrin variant comprises a rhodostomin variant.

4. The method of claim 1, wherein said isolated polypeptide comprises a variant of an amino acid sequence chosen from SEQ ID NOs: 36-40.

5. The method of claim 1, wherein said isolated polypeptide comprises an amino acid sequence chosen from SEQ ID NOs: 63-67.

6. The method of claim 1, wherein said isolated polypeptide comprises SEQ ID NO: 38.

7. The method of claim 1, wherein said isolated polypeptide comprises SEQ ID NO: 65.

8. The method of claim 1, wherein said isolated polypeptide is encoded by a polynucleotide comprising SEQ ID NO: 52.

9. The method of claim 1, wherein said polypeptide is pegylated or conjugated with albumin.

10. The method of claim 1, wherein the αvβ3 integrin-associated disease is chosen from osteoporosis, cancer, bone tumor or cancer growth and symptoms related thereto, tumor cell growth in bone, tumor metastasis in bone, malignancy-induced hypercalcemia, Paget's disease, rheumatic arthritis, osteoarthritis, and an ovariectomy-induced physiological change.

11. The method of claim 10, wherein said symptoms comprise a pathological symptom chosen from an increased osteoclast activity, increased bone resorption, bone lesion, hypercalcemia, a body weight loss, and any combinations thereof.

12. The method of claim 10, wherein the tumor cell growth in bone includes bone cancer cells, and metastasized cancer cells originating from one or more of prostate cancer, breast cancer, lung cancer, thyroid cancer, renal cancer, ovarian cancer, pancreatic cancer, myeloma cancer, hepatoma, and melanoma.

13. The method of claim 10, wherein said cancer comprises glioma.

14. The method of claim 10, wherein said method further comprises administering to said mammal a therapeutically effective amount of one or more other pharmaceutical agents.

15. The method of claim 14, wherein said other pharmaceutical agents are selected from the group consisting of an anti-cancer agent, an anti-inflammatory agent, an immune-modulating agent and an anti-osteoporosis agent.

16. The method of claim 15, wherein said anti-cancer agent is selected from the group consisting of an antiangiogenic agent, a cytotoxic agent and an anti-neoplastic agent.

17. The method of claim 16, wherein said method enhances the therapeutic efficacy of said anti-cancer agent.

18. The method of claim 16, wherein said method allows administering to said mammal a lower dose of said anti-cancer agent as compared to administering said anti-cancer agent without administering said isolated polypeptide, thereby decreasing side effects of said anti-cancer agent and/or decreasing resistance to said anti-cancer agent.

19. The method of claim 16, wherein said method results in lowering the rate of cancer recurrence in said mammal.

20. The method of claim 10, wherein said cancer is associated with a highly expressed osteopontin.

21. The method of claim 20, wherein said isolated polypeptide inhibits osteopontin-induced tumor invasion.

* * * * *